United States Patent
Azali et al.

(10) Patent No.: US 12,187,700 B2
(45) Date of Patent: Jan. 7, 2025

(54) POLYMORPHS AND COCRYSTALS OF A CARDIAC TROPONIN ACTIVATOR

(71) Applicants: Amgen Inc., Thousand Oaks, CA (US); Cytokinetics, Inc., South San Francisco, CA (US)

(72) Inventors: Stephanie Azali, Thousand Oaks, CA (US); Mary Chaves, Thousand Oaks, CA (US); Ron C. Kelly, Thousand Oaks, CA (US); Steven M. Mennen, Thousand Oaks, CA (US); Darren L Reid, Thousand Oaks, CA (US); Osama Suleiman, Thousand Oaks, CA (US); Ashraf Wilsily, Thousand Oaks, CA (US); Mark Wright, Thousand Oaks, CA (US)

(73) Assignees: Amgen Inc., Thousand Oaks, CA (US); Cytokinetics, Inc., South San Francisco, CA (US)

( * ) Notice: Subject to any disclaimer, the term of this patent is extended or adjusted under 35 U.S.C. 154(b) by 629 days.

(21) Appl. No.: 17/593,110

(22) PCT Filed: Mar. 12, 2020

(86) PCT No.: PCT/US2020/022219
§ 371 (c)(1),
(2) Date: Sep. 9, 2021

(87) PCT Pub. No.: WO2020/185982
PCT Pub. Date: Sep. 17, 2020

(65) Prior Publication Data
US 2022/0185790 A1  Jun. 16, 2022

Related U.S. Application Data

(60) Provisional application No. 62/817,165, filed on Mar. 12, 2019.

(51) Int. Cl.
*C07D 401/06* (2006.01)

(52) U.S. Cl.
CPC ........ *C07D 401/06* (2013.01); *C07B 2200/13* (2013.01)

(58) Field of Classification Search
CPC .......................... C07D 401/06; C07B 2200/13
USPC ......................................................... 514/343
See application file for complete search history.

(56) References Cited

U.S. PATENT DOCUMENTS

| | | |
|---|---|---|
| 4,522,811 A | 6/1985 | Eppstein |
| 10,723,720 B2 | 7/2020 | Ashcraft et al. |
| 10,899,746 B2 | 1/2021 | Ashcraft et al. |
| 11,254,658 B2 | 2/2022 | Debenedetto et al. |
| 11,299,479 B1 | 4/2022 | Aschraft |
| 11,780,826 B2 | 10/2023 | Ashcraft et al. |
| 2007/0078126 A1 | 4/2007 | Morgan et al. |
| 2009/0192168 A1 | 7/2009 | Muci et al. |
| 2013/0267537 A1 | 10/2013 | Morgan et al. |
| 2019/0077793 A1 | 3/2019 | Ashcraft et al. |
| 2020/0223829 A1 | 7/2020 | Ashcraft et al. |
| 2020/0223830 A1 | 7/2020 | Ashcraft et al. |
| 2022/0185791 A1 | 6/2022 | Azali et al. |
| 2022/0281850 A1 | 9/2022 | Ashcraft et al. |
| 2024/0158372 A1 | 5/2024 | Ashcraft |

FOREIGN PATENT DOCUMENTS

| | | |
|---|---|---|
| JP | 2016513683 A | 5/2016 |
| JP | 2020533347 A | 11/2020 |
| WO | 2000055188 A1 | 9/2000 |
| WO | 2009004383 A2 | 1/2009 |
| WO | 2014152236 A1 | 9/2014 |
| WO | 2019055590 A1 | 3/2019 |
| WO | 2020185983 A1 | 9/2020 |

OTHER PUBLICATIONS

European Examination Report mailed on Jul. 27, 2023, for European Patent No. 20717440.0, filed Oct. 6, 2021, 4 pages.
U.S. Appl. No. 18/451,757, filed Aug. 17, 2023, for Ashcraft et al.
Bastin, R.J. et al. (Jan. 1, 2000). "Salt Selections and Optimisation for Pharmaceutical New Chemical Entities," Organic Process Research and Development 4(5):427-435.
Byrn, S. et al. (Jan. 1, 1995). "Pharmaceutical Solids: A Strategic Approach to Regulatory Considerations," Pharmaceutical Research 12(7):945-954.
International Preliminary Report on Patentability mailed Sep. 23, 2021, for International Patent Application No. PCT/US2020/022219, filed Mar. 12, 2020, 10 pages.
International Preliminary Report on Patentability mailed Sep. 23, 2021, for International Patent Application No. PCT/US2020/022221, filed Mar. 12, 2020, 10 pages.
International Search Report and Written Opinion mailed Jun. 3, 2020, for International Patent Application No. PCT/US2020/022221, filed Mar. 12, 2020, 17 pages.
International Search Report and Written Opinion of the International Searching Authority mailed Jun. 3, 2020, for International Patent Application No. PCT/US2020/022219, filed Mar. 12, 2020, 13 pages.
Karagianni, A. et al. (Jan. 25, 2018). "Pharmaceutical Cocrystals: New Solid Phase Modification Approaches for the Formulation of APIs," Pharmaceutics 10(18):1-30.
U.S. Appl. No. 17/627,594, filed Feb. 15, 2022, for Ashcraft et al.
European Examination Report mailed on Feb. 16, 2024, for European Patent No. 20717438.4, filed Oct. 6, 2021, 5 pages.

*Primary Examiner* — Kristin A Vajda
(74) *Attorney, Agent, or Firm* — MORRISON & FOERSTER LLP

(57) ABSTRACT

Provided herein are free base crystalline forms, crystalline salts, solvates, amorphous free base, and cocrystals of Compound A.

39 Claims, 45 Drawing Sheets

POLYMORPHS AND COCRYSTALS OF A CARDIAC TROPONIN ACTIVATOR

CROSS REFERENCE TO RELATED APPLICATIONS

This application is a national stage application under 35 U.S.C. § 371 of International Application No. PCT/US2020/022219, filed internationally on Mar. 12, 2020, which claims benefit of U.S. Provisional Application No. 62/817,165, filed Mar. 12, 2019.

BACKGROUND

The compound (1R,3R,5R)—N-((R)-cyclopropyl(2,5-difluoro-4-(trifluoromethyl)phenyl)methyl)-2-(5-(methylsulfonyl)nicotinoyl)-2-azabicyclo[3.1.0]hexane-3-carboxamide, is useful as a cardiac troponin activator:

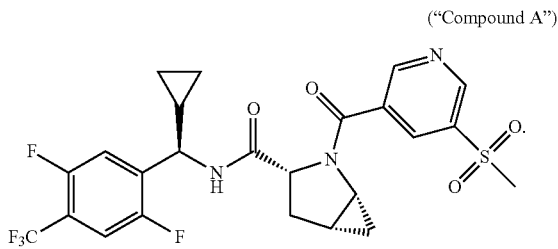 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]

("Compound A")

There is a need for various new salt and crystalline forms of Compound A with different chemical and physical stabilities, and formulations and uses of the same.

SUMMARY

Provided herein are crystalline forms of Compound A or a salt thereof, including free base crystalline forms, crystalline salts, and crystalline solvates. In some embodiments, provided herein is the free base anhydrous crystalline Form I of Compound A. In some embodiments, provided herein is the free base anhydrous crystalline Form II of Compound A. In some embodiments, provided herein is the free base monohydrate crystalline Form III of Compound A. In some embodiments, provided herein is the free base anhydrous crystalline Form IV of Compound A. In some embodiments, provided herein is the crystalline form of Compound A hydrochloride salt. In some embodiments, provided herein is the crystalline form of Compound A and dichloromethane. In some embodiments, provided herein is the crystalline form of Compound A and nitromethane. In some embodiments, provided herein is the crystalline form of Compound A and hexafluoro-2-propanol.

Also provided herein are cocrystals comprising Compound A and a coformer. In some embodiments, the coformer comprises propyl gallate. In some embodiments, the coformer comprises glycerol. In some embodiments, the coformer comprises propylene glycol. In some embodiments, the coformer comprises maltol. In some embodiments, the coformer comprises urea.

Further provided are pharmaceutical compositions comprising a crystalline form or cocrystal of Compound A or salt thereof as disclosed herein and a pharmaceutical acceptable carrier.

Further provided are methods of treating heart failure in a subject in need thereof comprising administering to the subject the crystalline form or cocrystal of Compound A or salt thereof disclosed herein in an amount effective to treat heart failure.

DETAILED DESCRIPTION

The present disclosure provides polymorphs and cocrystals of (1R,3R,5R)-N-((R)-cyclopropyl(2,5-difluoro-4-(trifluoromethyl)phenyl)methyl)-2-(5-(methylsulfonyl)nicotinoyl)-2-azabicyclo[3.1.0]hexane-3-carboxamide, termed "Compound A" herein, and having a structure of:

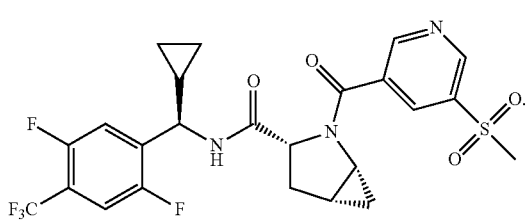 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]

Embodiments of the free base forms, salt forms, solvates, cocrystals and amorphous form of Compound A can be characterized by one or more of the parameters described in further detail below.

Free Base Crystalline Forms of Compound A

Provided herein are free base crystalline forms of Compound A. In embodiments, the free base crystalline forms of Compound A can be nonionic forms of Compound A. In embodiments, the free base crystalline forms of Compound A can be anhydrous. In embodiments, the free base crystalline forms of Compound A can be a monohydrate.

Free Base Anhydrous Crystalline Form I

Figure 1:
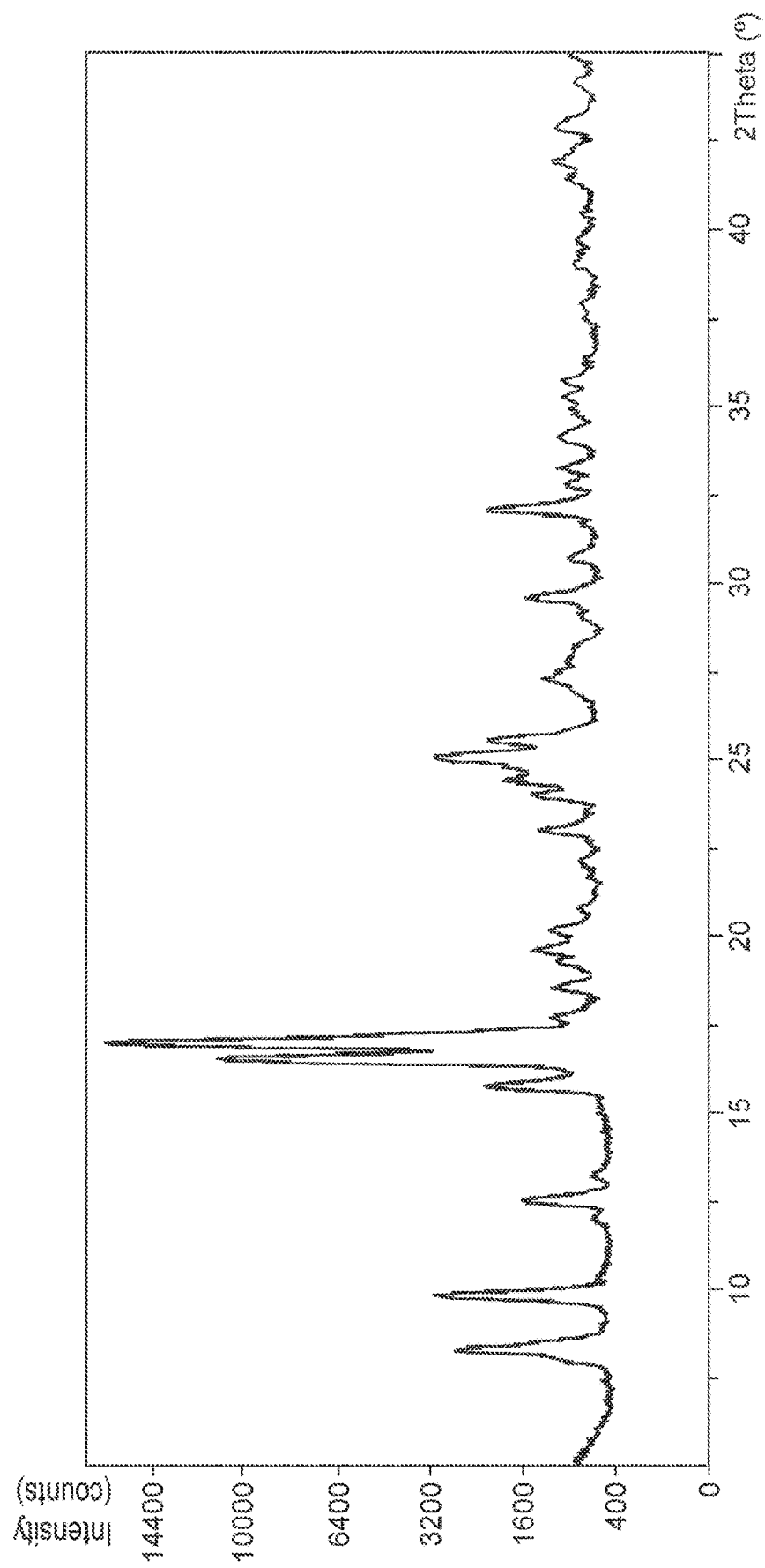
FIG. 1 depicts an X-ray powder diffraction ("XRPD") pattern of the free base anhydrous crystalline Form I.

Free base anhydrous crystalline form I of Compound A ("Form I") can be characterized by an X-ray powder diffraction pattern, obtained as set forth in the Examples, having peaks at about 9.78, 12.45, 15.70, 16.46, and 16.94±0.2° 2θ using Cu Kα radiation. Form I optionally can be further characterized by an X-ray powder diffraction pattern having additional peaks at about 8.23, 24.40, 25.03, 25.49, and 32.03±0.2° 2θ using Cu Kα radiation. Form I optionally can be further characterized by an X-ray powder diffraction pattern having additional peaks at about 19.56, 20.11, 22.99, 23.97, 29.53, 41.91, and 42.83±0.2° 2θ using Cu Kα radiation. Form I optionally can be characterized by an X-ray powder diffraction pattern having peaks shown in Table 1 set forth in the Examples. In some embodiments, Form I has an X-ray powder diffraction pattern substantially as shown in FIG. 1, wherein by "substantially" is meant that the reported peaks can vary by about ±0.2°. It is well known in the field of XRPD that while relative peak heights in spectra are dependent on a number of factors, such as sample preparation and instrument geometry, peak positions are relatively insensitive to experimental details.

Figure 2:
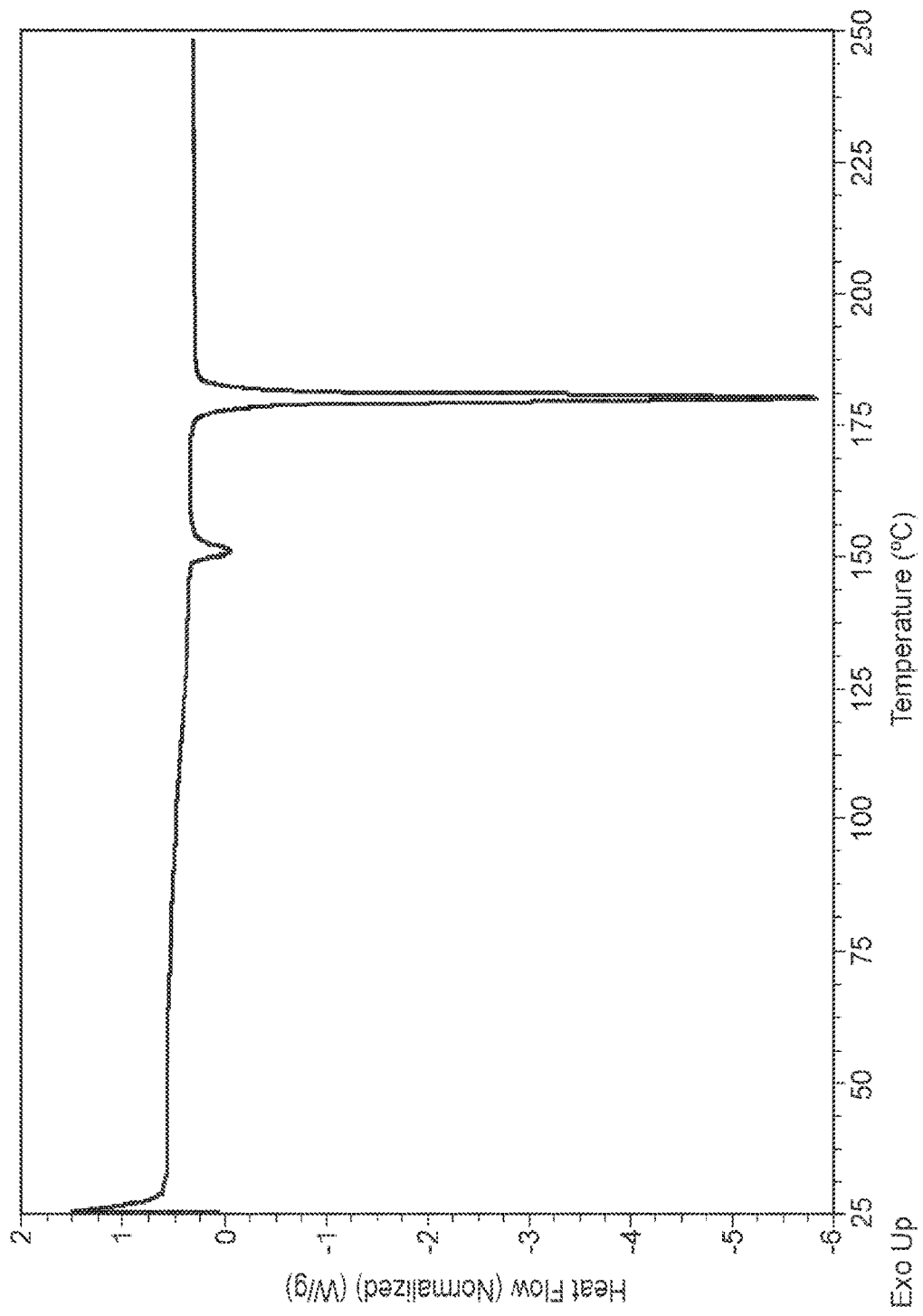
FIG. 2 depicts a differential scanning calorimetry ("DSC") thermograph of the free base anhydrous crystalline Form I and Form II.

Differential scanning calorimetry (DSC) thermographs were obtained, as set forth in the Examples, for Form I. The DSC curve indicates an endothermic transition at about 152° C.±3° C. Thus, in some embodiments, Form I can be characterized by a DSC thermograph having a solid-solid transition endotherm with an onset in a range of about 147° C. to about 157° C. For example, in some embodiments Form I is characterized by DSC, as shown in FIG. 2.

Figure 3:
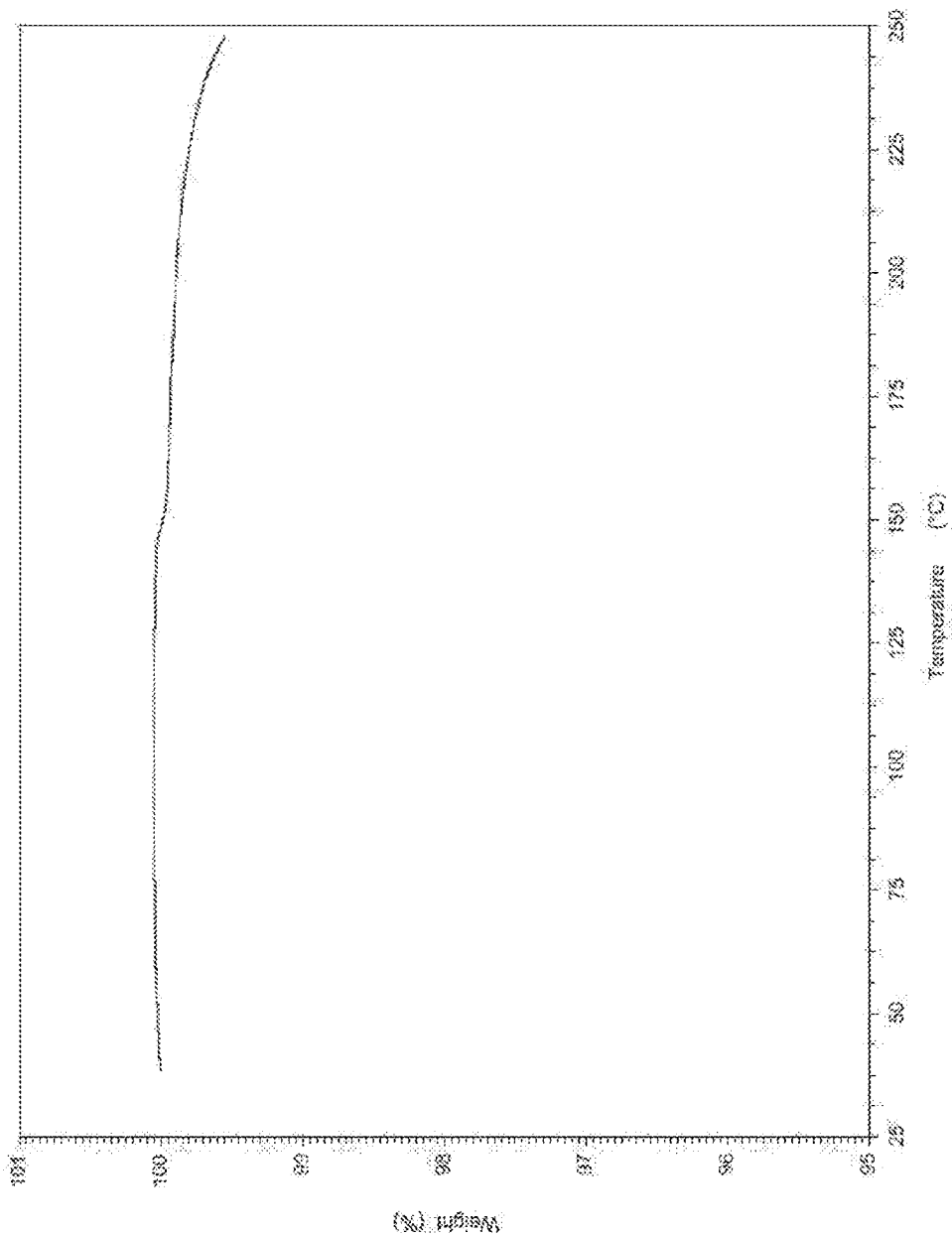
FIG. 3 depicts a thermogravimetric analysis ("TGA") trace of the free base anhydrous crystalline Form I.
Figure 4:
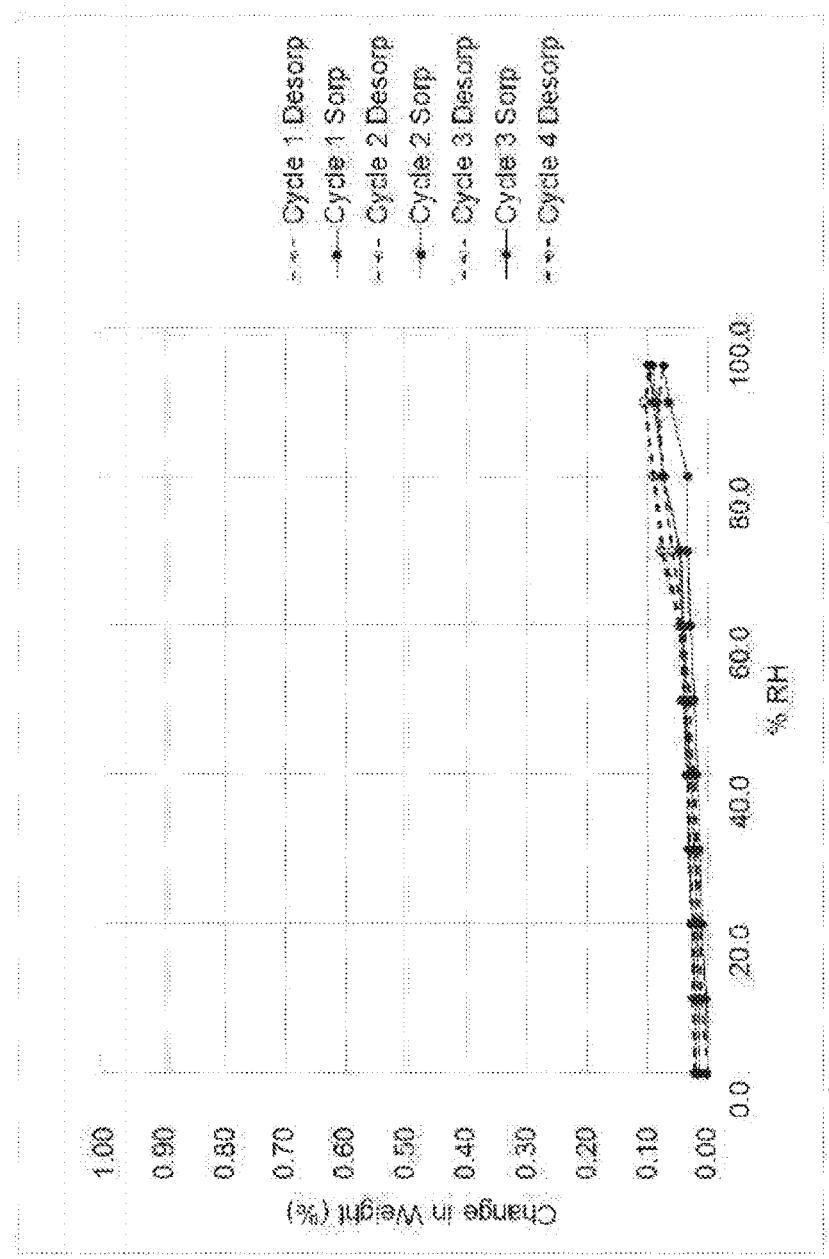
FIG. 4 depicts a dynamic vapor sorption ("DVS") graph of the free base anhydrous crystalline Form I.

Form I also can be characterized by thermogravimetric analysis (TGA). Thus, Form I can be characterized by a weight loss in a range of about 0% to about 1% with an onset temperature in a range of about 145° C. to about 150° C. For example, Form I can be characterized by a weight loss of about 0.6%, up to about 200° C. In some embodiments, Form I has a thermogravimetric analysis substantially as depicted in FIG. 3, wherein by "substantially" is meant that the reported TGA features can vary by about ±5° C. In embodiments, Form I has a dynamic vapor sorption ("DVS") substantially as shown in FIG. 4.

Free Base Anhydrous Crystalline Form II

Figure 5:
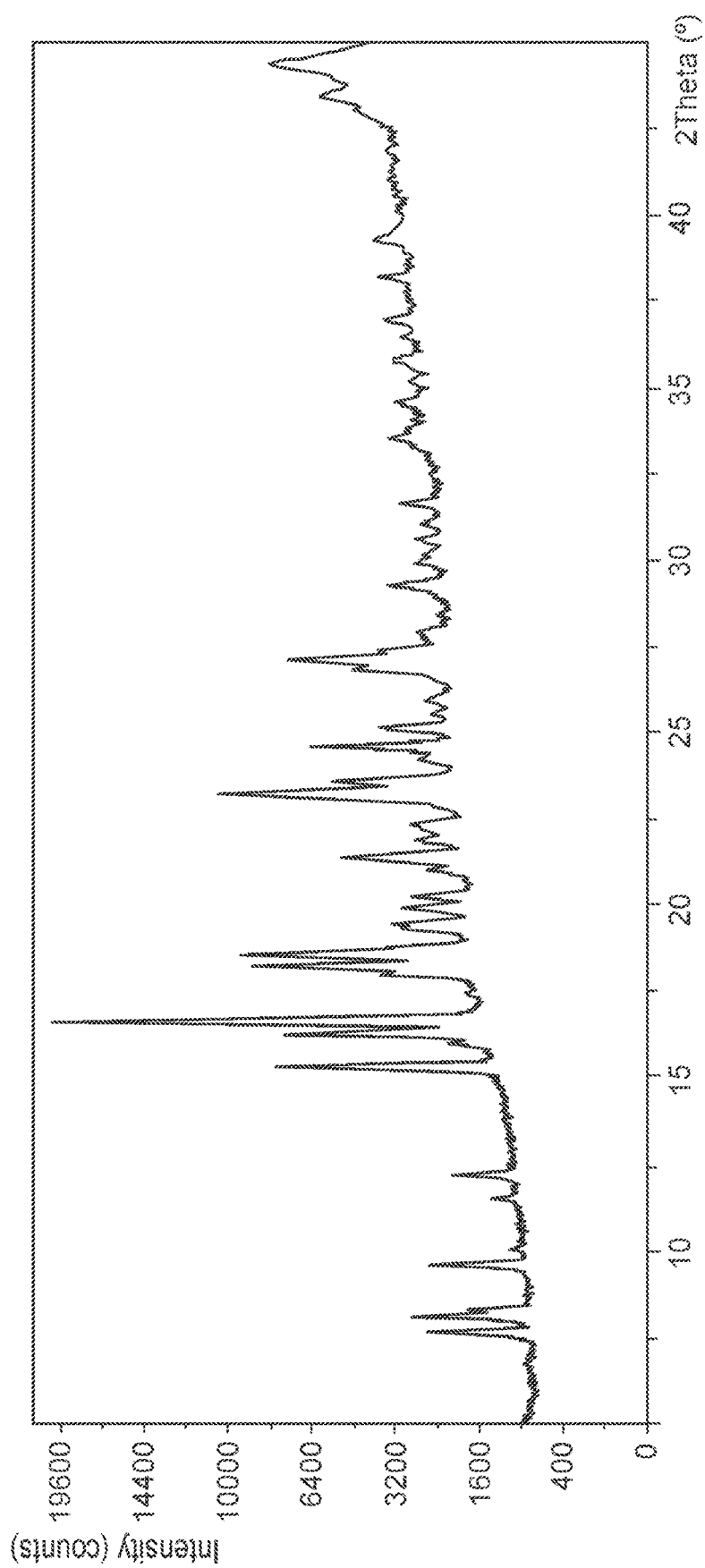
FIG. 5 depicts an XRPD pattern of the free base anhydrous crystalline Form II.

Free base anhydrous crystalline form II of Compound A ("Form II") can be characterized by an X-ray powder diffraction pattern, obtained as set forth in the Examples, having peaks at about 7.67, 11.54, 18.27, and 23.28±0.2° 2θ using Cu Kα radiation. Form II optionally can be further characterized by an X-ray powder diffraction pattern having additional peaks at about 15.36, 16.33, 18.58, 21.38, 23.59, 24.61, 27.09, 43.40, and 44.26±0.2° 2θ using Cu Kα radiation. Form II optionally can be further characterized by an X-ray powder diffraction pattern having additional peaks at about 18.01, 25.17, 38.15, and 39.26±0.2° 2θ using Cu Kα radiation. Form II optionally can be characterized by an X-ray powder diffraction pattern having peaks shown in Table 2 set forth in the Examples. In some embodiments, Form II has an X-ray powder diffraction pattern substantially as shown in FIG. 5, wherein by "substantially" is meant that the reported peaks can vary by about ±0.2°. It is well known in the field of XRPD that while relative peak heights in spectra are dependent on a number of factors, such as sample preparation and instrument geometry, peak positions are relatively insensitive to experimental details.

Differential scanning calorimetry (DSC) thermographs were obtained, as set forth in the Examples, for Form II. The DSC curve indicates an endothermic transition at about 181° C.±3° C. Thus, in some embodiments, Form II can be characterized by a DSC thermograph having a melting endotherm with an onset in a range of about 175° C. to about 185° C. For example, in some embodiments Form II is characterized by DSC, as shown in FIG. 2. There is a mixture of Form I and Form II in the DSC shown in FIG. 2.

Free Base Monohydrate Crystalline Form III

Figure 6:
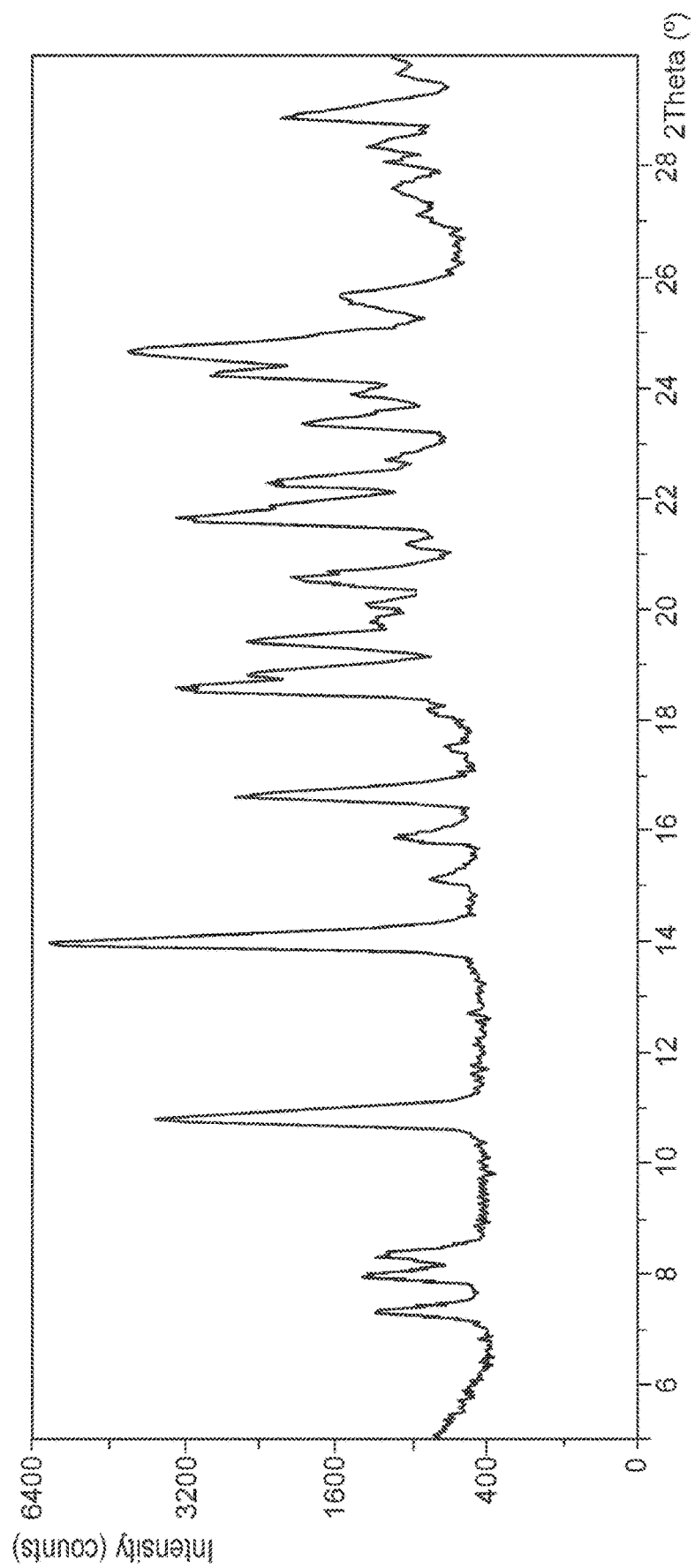
FIG. 6 depicts an XRPD pattern of the free base monohydrate crystalline Form III.

Free base monohydrate crystalline form III of Compound A ("Form III") can be characterized by an X-ray powder diffraction pattern, obtained as set forth in the Examples, having peaks at about 7.31, 10.77, and 13.96±0.2° 2θ using Cu Kα radiation. Form III optionally can be further characterized by an X-ray powder diffraction pattern having additional peaks at about 16.60, 18.56, 18.84, 19.41, 20.57, 21.61, 21.92, 22.28, 23.34, 24.23, 24.70, 25.69, and 28.87±0.2° 2θ using Cu Kα radiation. Form III optionally can be further characterized by an X-ray powder diffraction pattern having additional peaks at about 7.94, 20.10, 23.88, and 28.38±0.2° 2θ using Cu Kα radiation. Form III optionally can be characterized by an X-ray powder diffraction pattern having peaks shown in Table 3 set forth in the Examples. In some embodiments, Form III has an X-ray powder diffraction pattern substantially as shown in FIG. 6, wherein by "substantially" is meant that the reported peaks can vary by about ±0.2°.

Figure 7:
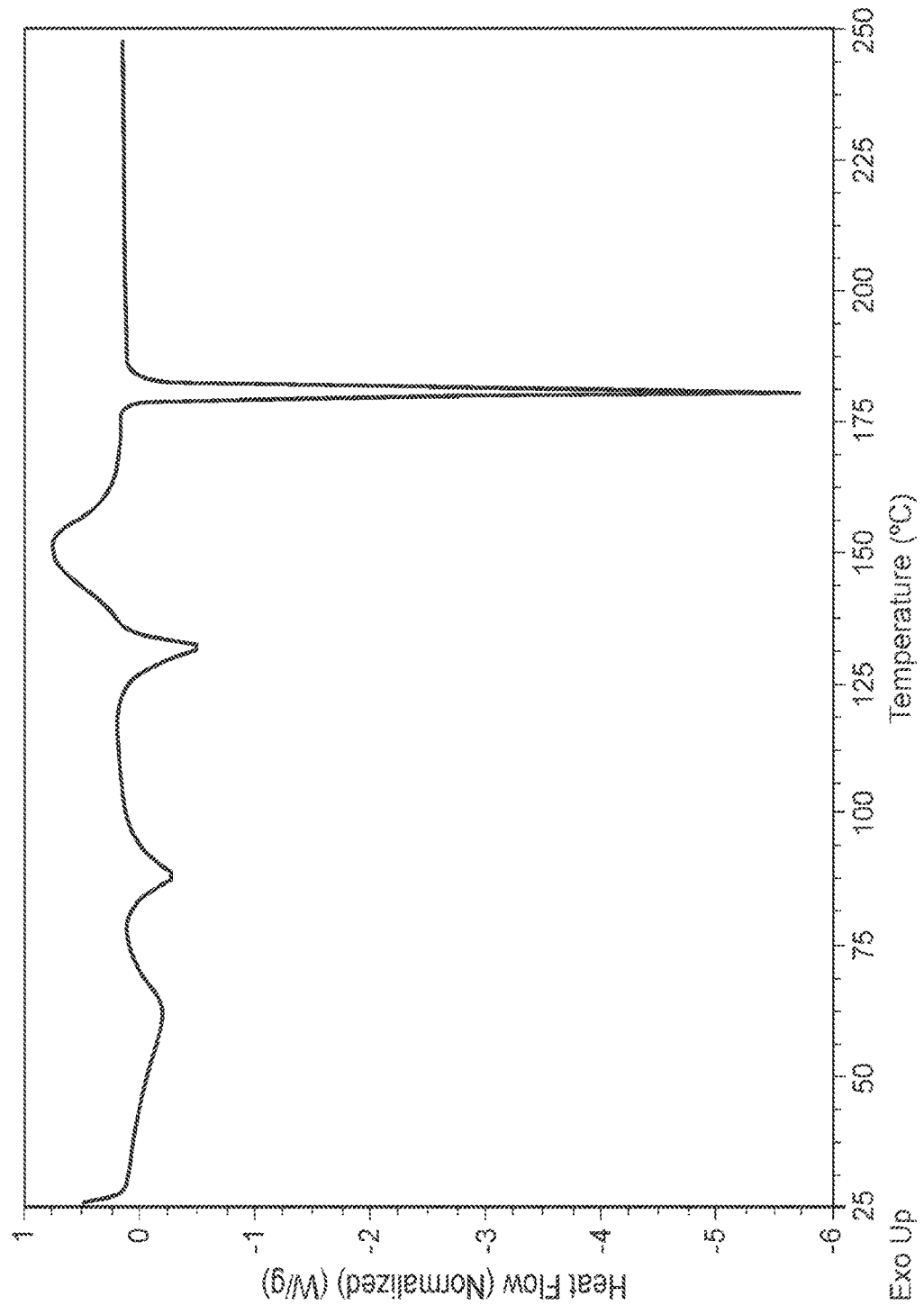
FIG. 7 depicts a DSC thermograph of the free base monohydrate crystalline Form III.

Differential scanning calorimetry (DSC) thermographs were obtained, as set forth in the Examples, for Form III. The DSC curve indicates an endothermic transition at about 132° C.±3° C. Thus, in some embodiments, Form III can be characterized by a DSC thermograph having a melting endotherm with an onset in a range of about 127° C. to about 137° C. For example, in some embodiments Form III is characterized by DSC, as shown in FIG. 7.

Figure 8:
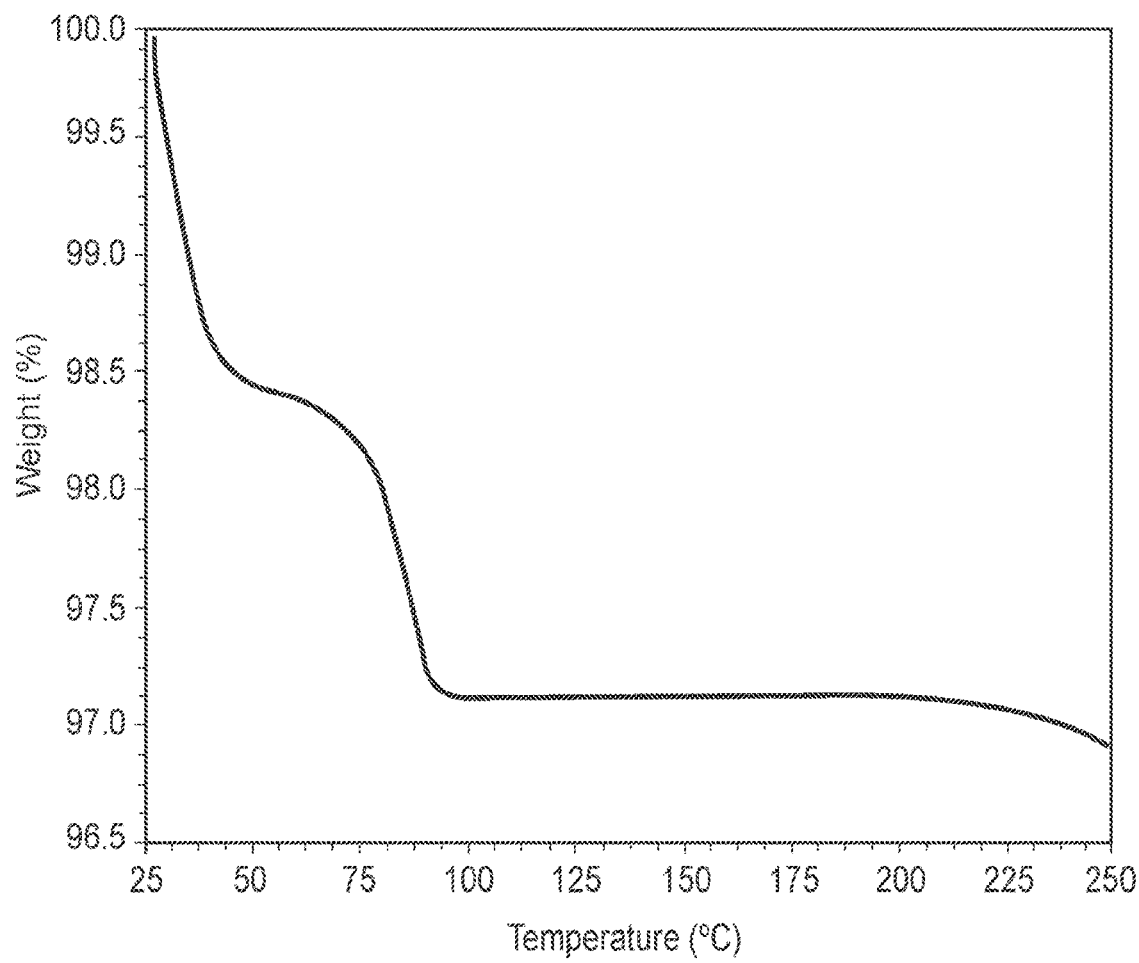
FIG. 8 depicts a TGA trace of the free base monohydrate crystalline Form III.
Figure 9:
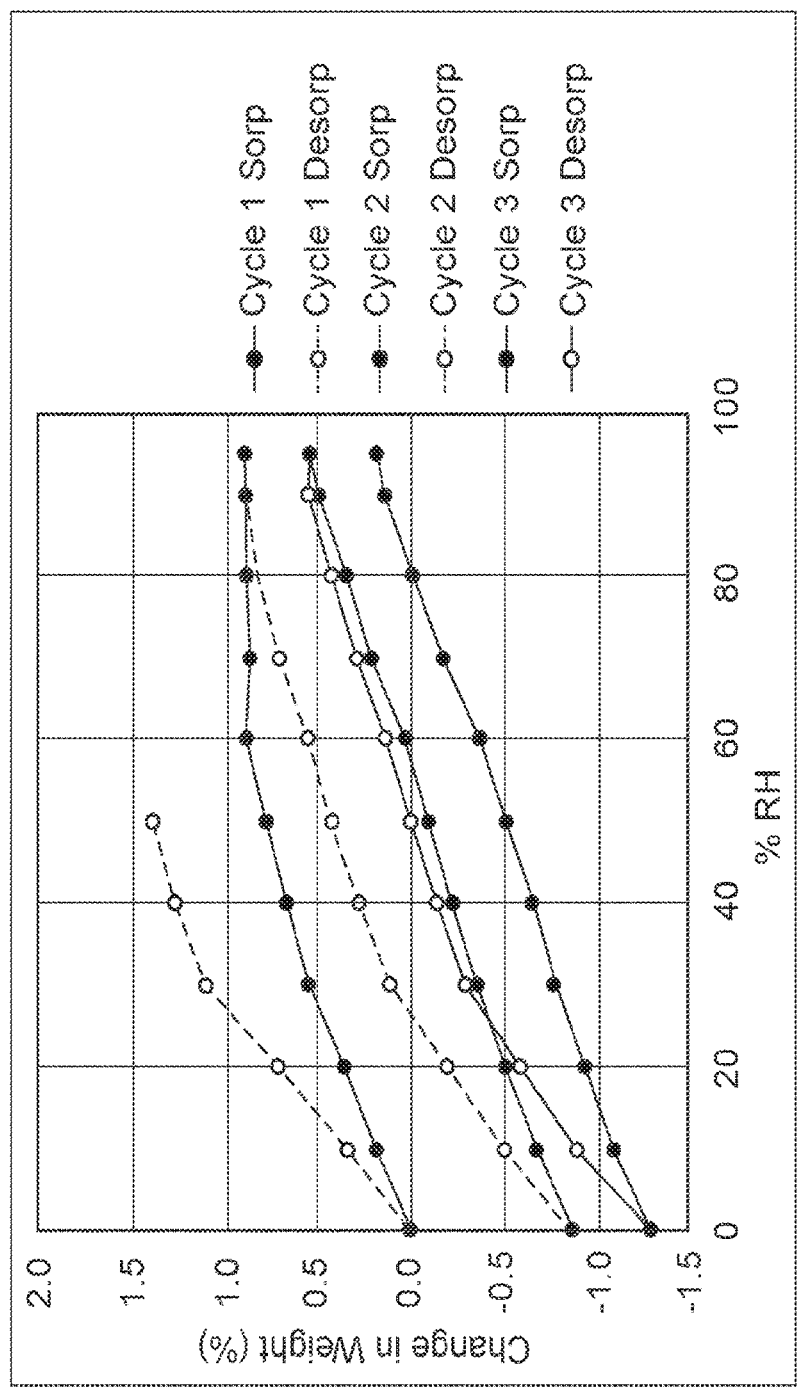
FIG. 9 depicts a DVS graph of the free base monohydrate crystalline Form III.

Form III also can be characterized by thermogravimetric analysis (TGA). Thus, Form III can be characterized by a weight loss in a range of about 2.5% to about 3.2% with an onset temperature in a range of about 25° C. to about 35° C. For example, Form III can be characterized by a weight loss of about 2.8%, up to about 200° C. In some embodiments, Form III has a thermogravimetric analysis substantially as depicted in FIG. 8, wherein by "substantially" is meant that the reported TGA features can vary by about ±5° C. In embodiments, Form III has a dynamic vapor sorption ("DVS") substantially as shown in FIG. 9.

Free Base Anhydrous Crystalline Form IV

Figure 10:
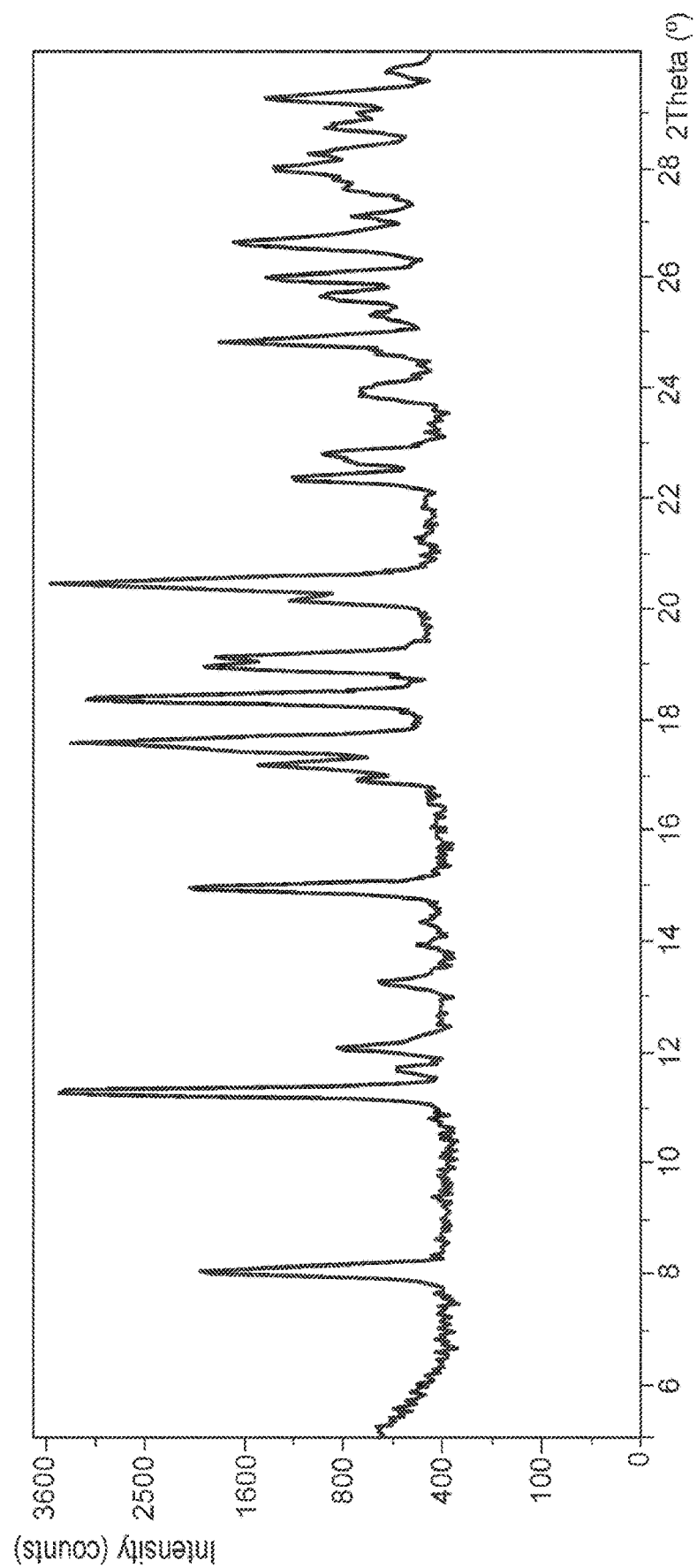
FIG. 10 depicts an XRPD pattern of the free base anhydrous crystalline Form IV.

Free base anhydrous crystalline form IV of Compound A ("Form IV") can be characterized by an X-ray powder diffraction pattern, obtained as set forth in the Examples, having peaks at about 8.06, 11.29, and 14.97±0.2° 2θ using Cu Kα radiation. Form IV optionally can be further characterized by an X-ray powder diffraction pattern having additional peaks at about 17.19, 17.63, 18.39, 18.95, 19.17, 20.50, 24.87, 26.03, 26.62, 27.99, and 29.25±0.2° 2θ using Cu Kα radiation. Form IV optionally can be further characterized by an X-ray powder diffraction pattern having additional peaks at about 12.08, 20.17, 22.37, 22.86, 25.69, 28.26, and 28.73±0.2° 2θ using Cu Kα radiation. Form IV optionally can be characterized by an X-ray powder diffraction pattern having peaks shown in Table 4 set forth in the Examples. In some embodiments, Form IV has an X-ray powder diffraction pattern substantially as shown in FIG. 10, wherein by "substantially" is meant that the reported peaks can vary by about ±0.2°.

Figure 11:
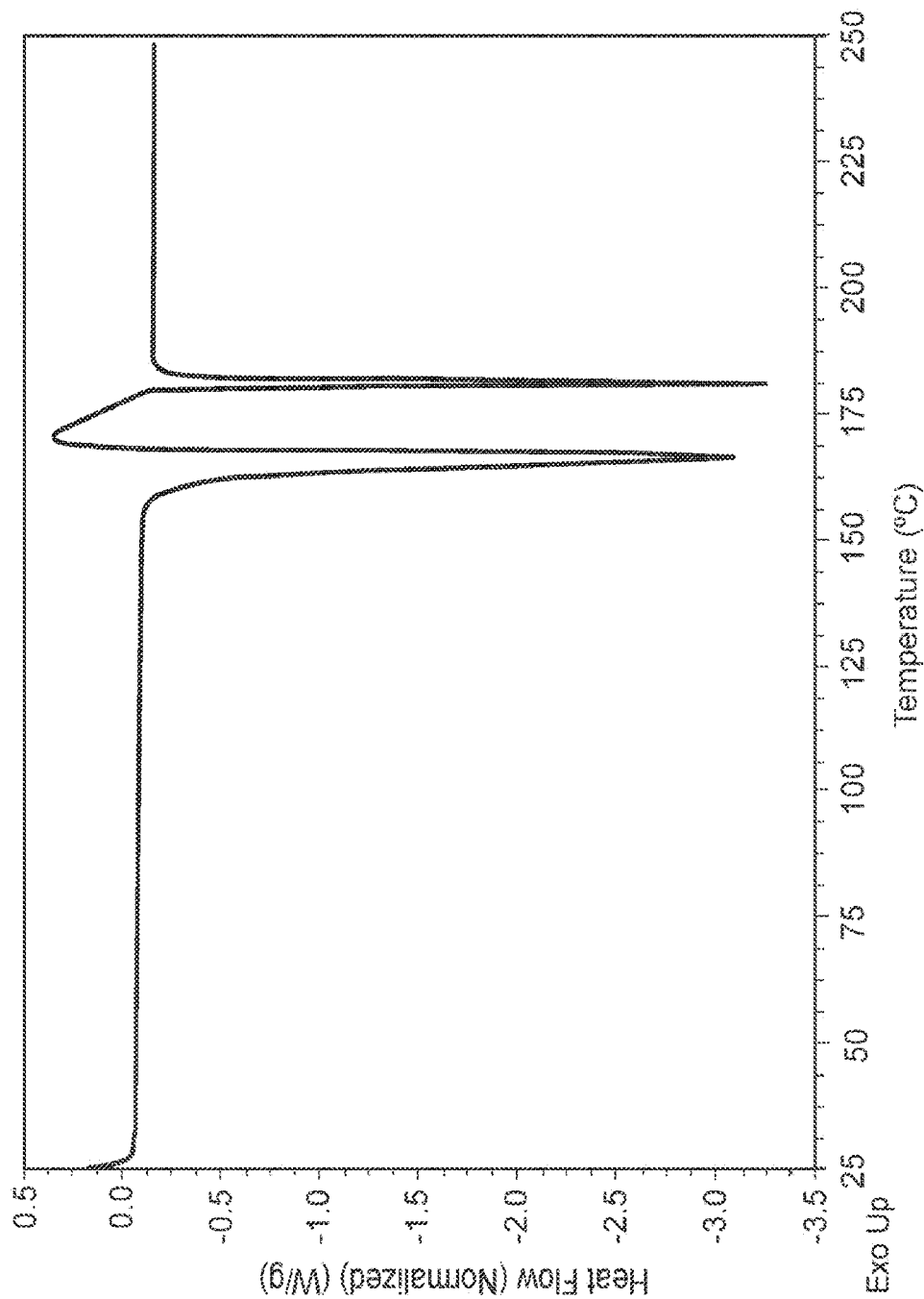
FIG. 11 depicts a DSC thermograph of the free base anhydrous crystalline Form IV.

Differential scanning calorimetry (DSC) thermographs were obtained, as set forth in the Examples, for Form IV. The DSC curve indicates an endothermic transition at about 167° C.±3° C. Thus, in some embodiments, Form IV can be characterized by a DSC thermograph having a melting endotherm with an onset in a range of about 160° C. to about 175° C. For example, in some embodiments Form IV is characterized by DSC, as shown in FIG. 11.

Figure 12:
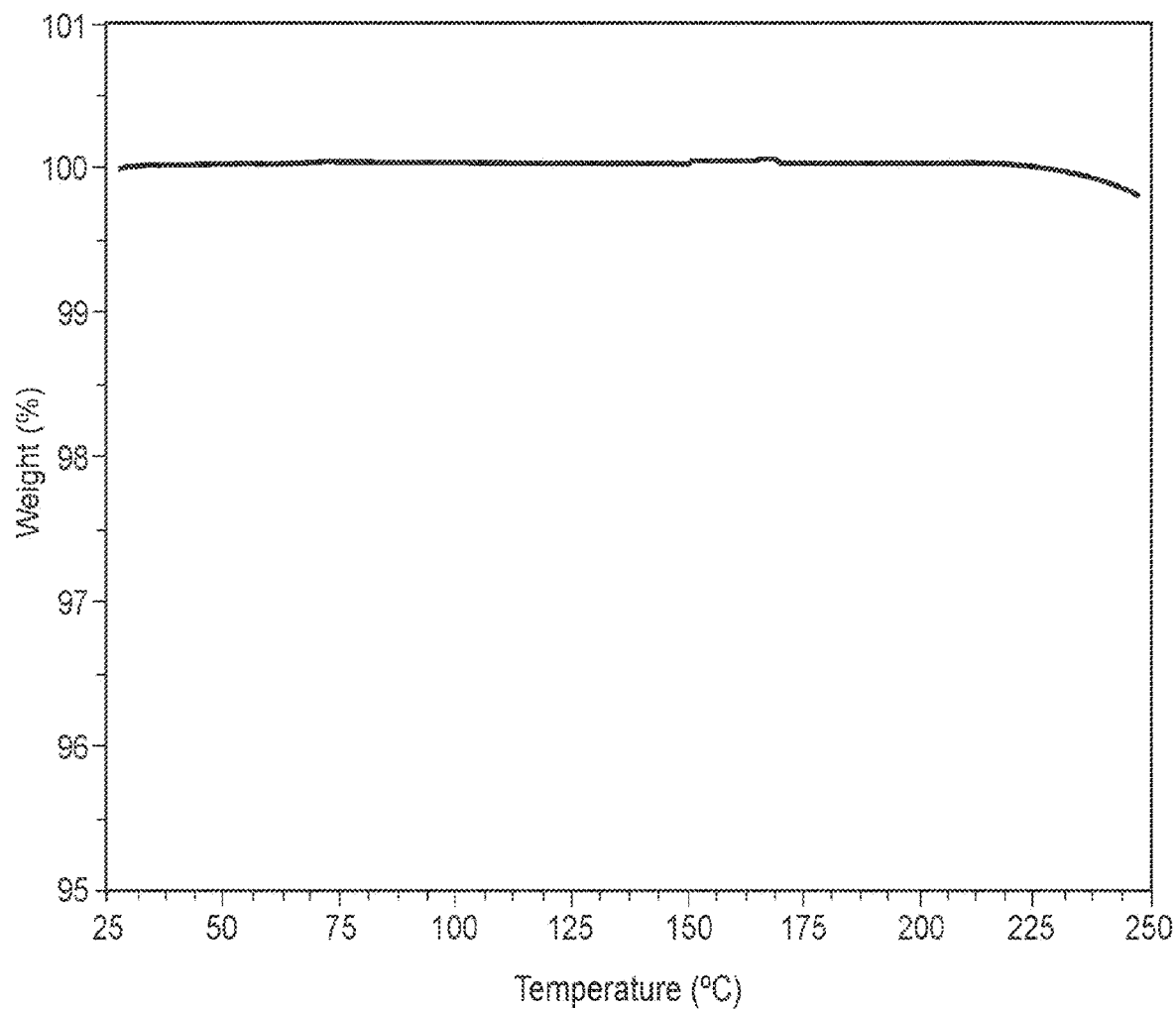
FIG. 12 depicts a TGA trace of the free base anhydrous crystalline Form IV.
Figure 13:
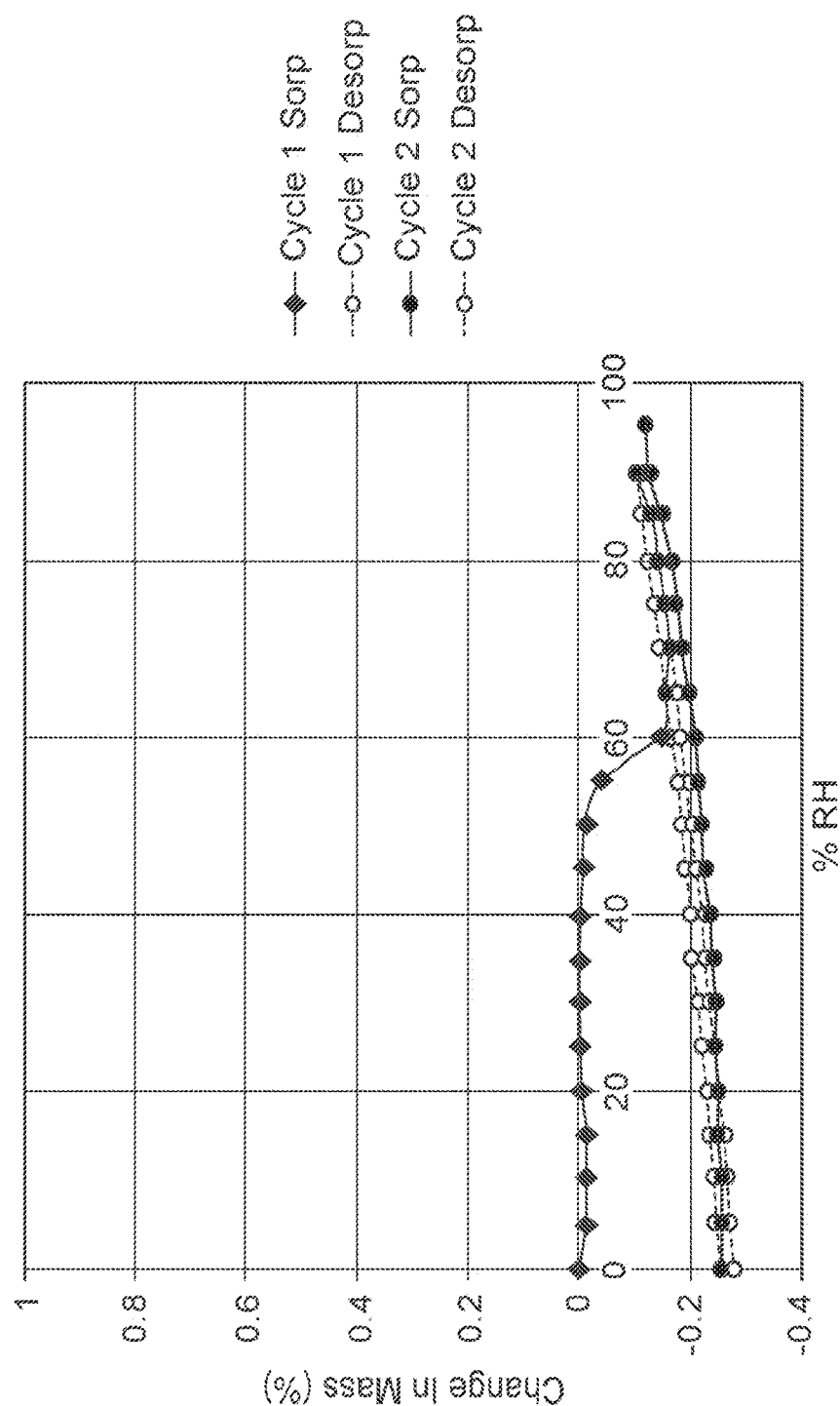
FIG. 13 depicts a DVS graph of the free base anhydrous crystalline Form IV.

Form IV also can be characterized by thermogravimetric analysis (TGA). Thus, Form IV can be characterized by a weight loss in a range of about 0% to about 0.5% with an onset temperature in a range of about 25° C. to about 35° C. For example, Form IV can be characterized by a weight loss of about 0%, up to about 200° C. In some embodiments, Form IV has a thermogravimetric analysis substantially as depicted in FIG. 12, wherein by "substantially" is meant that the reported TGA features can vary by about ±5° C. In embodiments, Form IV has a dynamic vapor sorption ("DVS") substantially as shown in FIG. 13.

Figure 14:
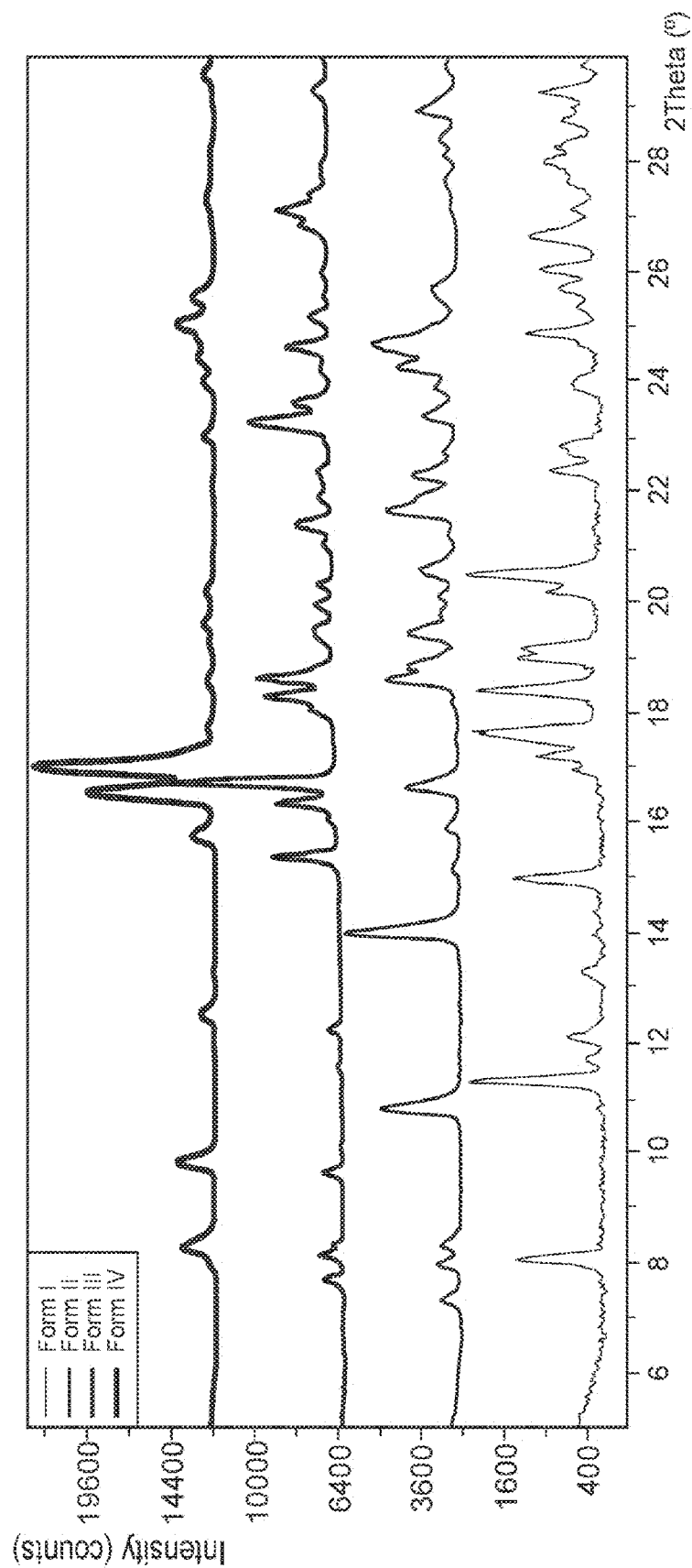
FIG. 14 depicts an XRPD pattern overlay of free base forms I (top), II (upper middle), III (lower middle), and IV (bottom).
Figure 15:
FIG. 15 depicts a summary of the thermodynamic relationship between the free base forms I, II, III, and IV.

A summary of the distinct XRPD peaks in free base crystalline forms I to IV can be seen in Table 5 and an overlay of the four different crystalline forms is shown in FIG. 14. A depiction of the thermodynamic relationship between free base crystalline forms I to IV is depicted in FIG. 15.

Compound A Salts

Crystalline Hydrochloride Salt

Figure 16:
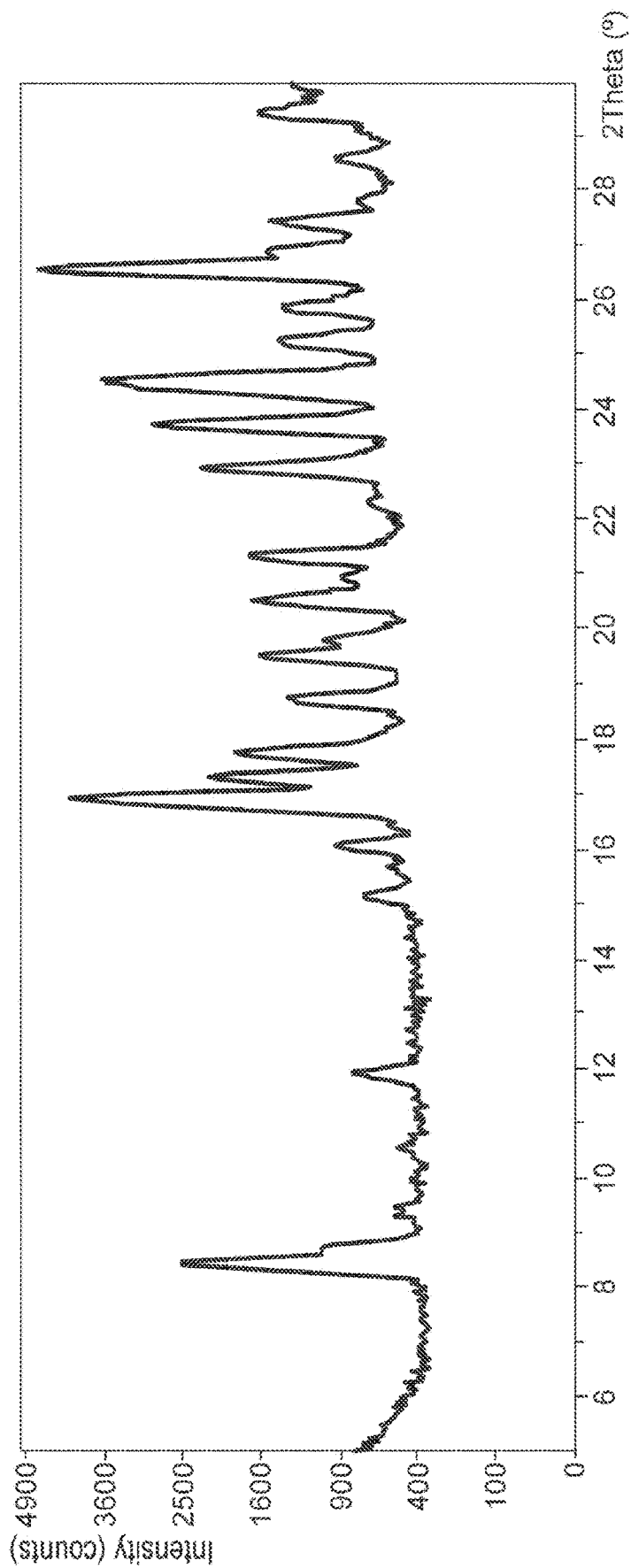
FIG. 16 depicts an XRPD pattern of the hydrochloride salt crystalline form.

Crystalline form of Compound A hydrochloride salt ("hydrochloride salt") can be characterized by an X-ray powder diffraction pattern, obtained as set forth in the Examples, having peaks at about 8.45, 16.93, 23.74, 24.59, and 26.57±0.2° 2θ using Cu Kα radiation. The hydrochloride salt optionally can be further characterized by an X-ray powder diffraction pattern having additional peaks at about 17.33, 17.76, 18.75, 19.51, 19.81, 20.53, 21.36, 22.95, 25.28, 25.89, 26.94, 27.44, and 29.41±0.2° 2θ using Cu Kα radiation. The hydrochloride salt optionally can be further characterized by an X-ray powder diffraction pattern having additional peaks at about 8.74, 16.08, 19.81, and 28.58±0.2° 2θ using Cu Kα radiation. The hydrochloride salt optionally can be characterized by an X-ray powder diffraction pattern having peaks shown in Table 6 set forth in the Examples. In some embodiments, the hydrochloride salt has an X-ray powder diffraction pattern substantially as shown in FIG. 16, wherein by "substantially" is meant that the reported peaks can vary by about ±0.2°.

Figure 17:
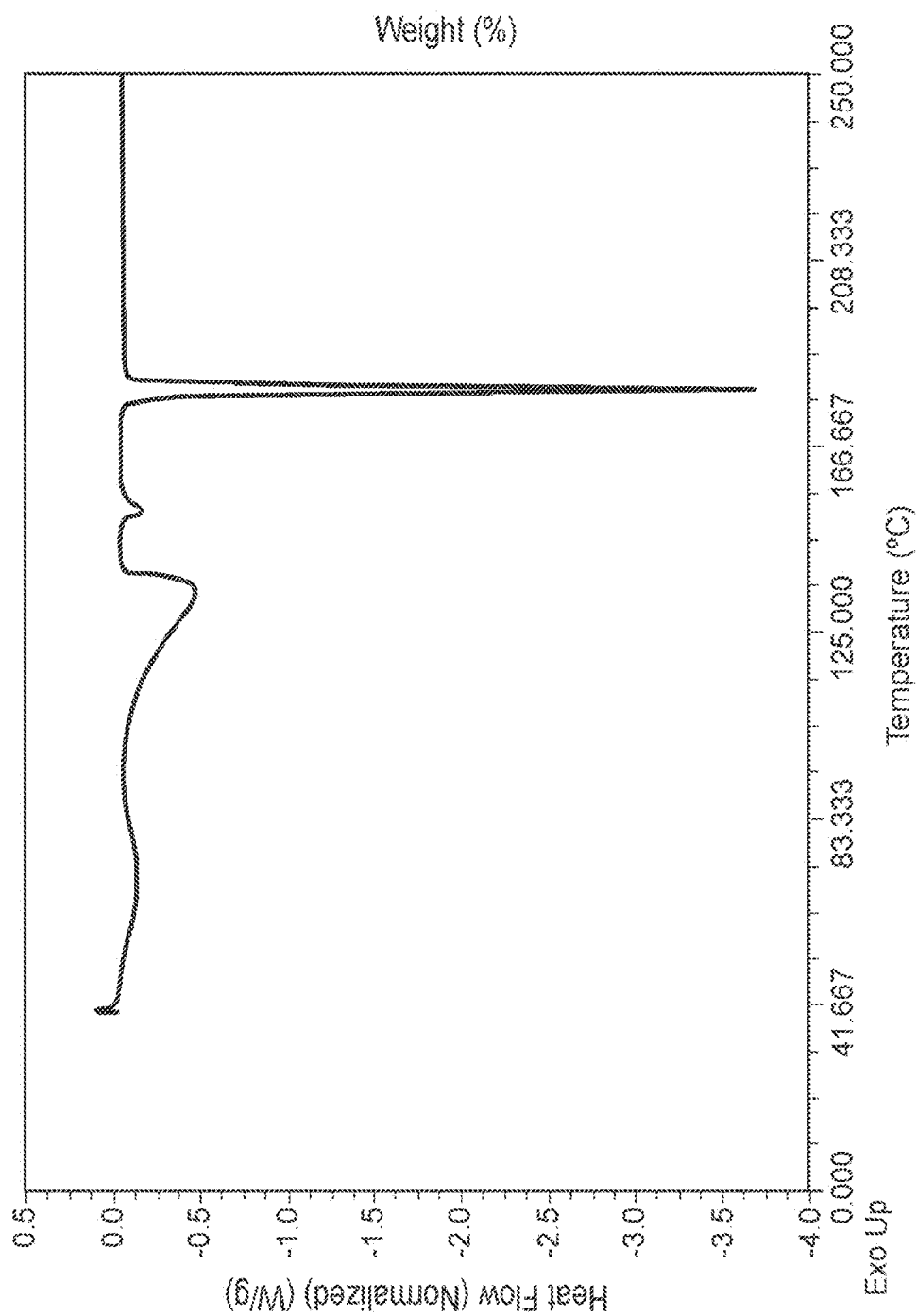
FIG. 17 depicts a DSC thermograph of the hydrochloride salt crystalline form.

Differential scanning calorimetry (DSC) thermographs were obtained, as set forth in the Examples, for the hydrochloride salt. The DSC curve indicates an endothermic transition at about 134° C.±3° C. Thus, in some embodiments, the hydrochloride salt can be characterized by a DSC thermograph having a decomposition endotherm with an onset in a range of about 125° C. to about 140° C. For example, in some embodiments the hydrochloride salt is characterized by DSC, as shown in FIG. 17.

Figure 18:
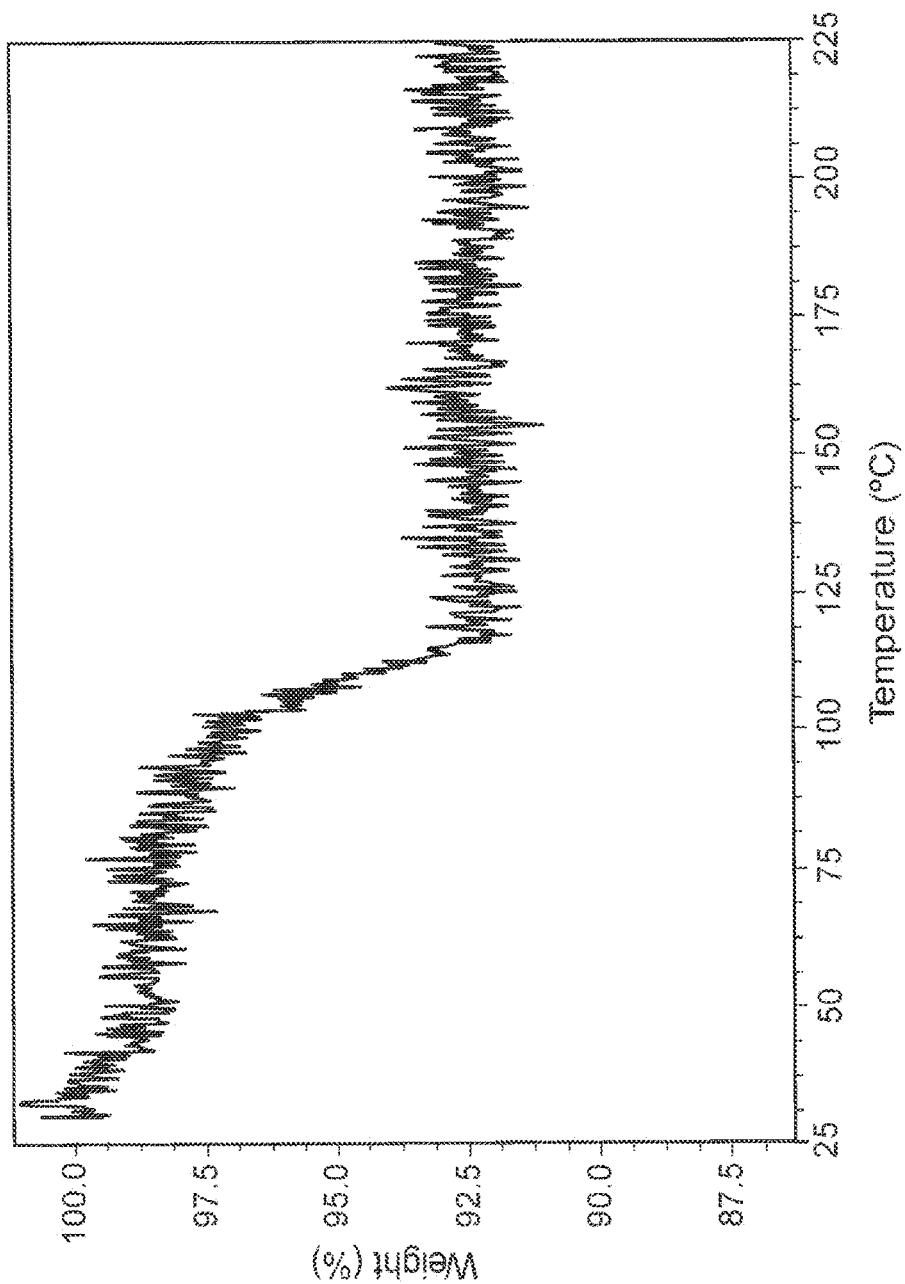
FIG. 18 depicts a TGA trace of the hydrochloride salt crystalline form.
Figure 19:
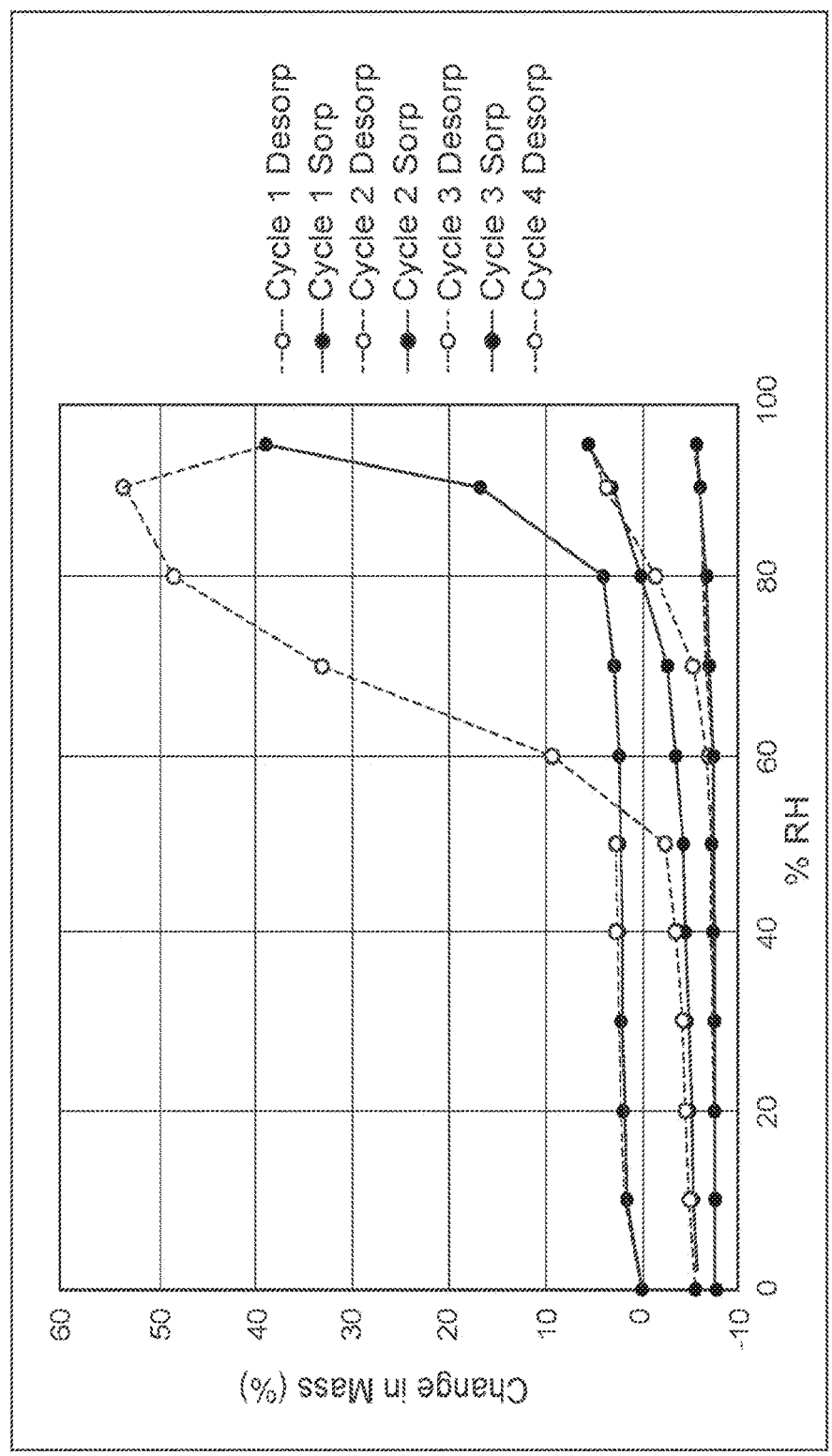
FIG. 19 depicts a DVS graph of the hydrochloride salt crystalline form.

The hydrochloride salt also can be characterized by thermogravimetric analysis (TGA). Thus, the hydrochloride salt can be characterized by a weight loss in a range of about 6.5% to about 8.5% with an onset temperature in a range of about 25° C. to about 35° C. For example, the hydrochloride salt can be characterized by a weight loss of about 7.5%, up to about 200° C. In some embodiments, the hydrochloride salt has a thermogravimetric analysis substantially as depicted in FIG. 18, wherein by "substantially" is meant that the reported TGA features can vary by about ±5° C. In embodiments, the hydrochloride salt has a dynamic vapor sorption ("DVS") substantially as shown in FIG. 19.

Compound A Solvates

Dichloromethane Solvate

Figure 20:
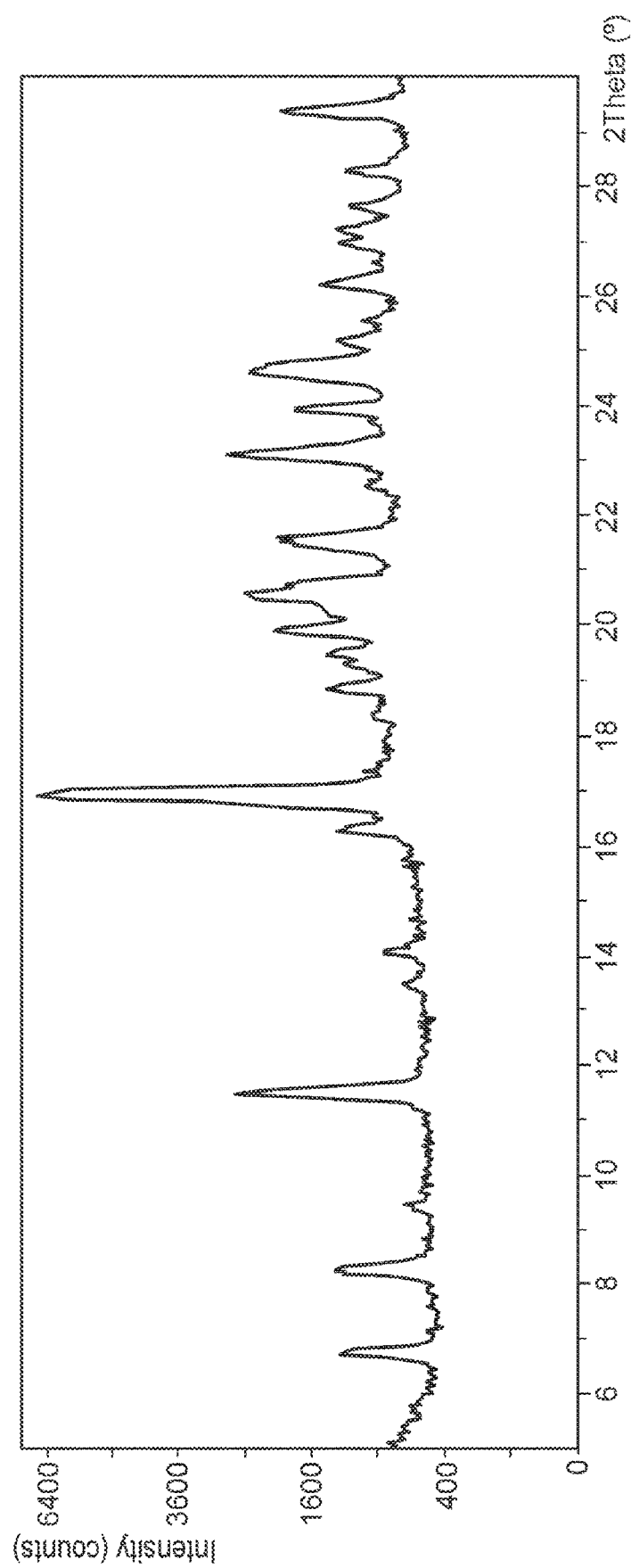
FIG. 20 depicts an XRPD pattern of the crystalline form of Compound A and dichloromethane.

A crystalline form of Compound A and dichloromethane ("dichloromethane solvate") can be characterized by an X-ray powder diffraction pattern, obtained as set forth in the Examples, having peaks at about 11.46, 16.91, 23.10, and 24.58±0.2° 2θ using Cu Kα radiation. The dichloromethane solvate optionally can be further characterized by an X-ray powder diffraction pattern having additional peaks at about 8.25, 16.26, 18.82, 19.50, 19.90, 20.52, 20.79, 21.58, 23.92, and 29.35±0.2° 2θ using Cu Kα radiation. The dichloromethane solvate optionally can be further characterized by an X-ray powder diffraction pattern having additional peaks at about 6.76, 25.18, 26.20, 26.95, 27.18, 27.62, and 28.26±0.2° 2θ using Cu Kα radiation. The dichloromethane solvate optionally can be characterized by an X-ray powder diffraction pattern having peaks shown in Table 7 set forth in the Examples. In some embodiments, the dichloromethane solvate has an X-ray powder diffraction pattern substantially as shown in FIG. 20, wherein by "substantially" is meant that the reported peaks can vary by about ±0.2°.

Figure 21:
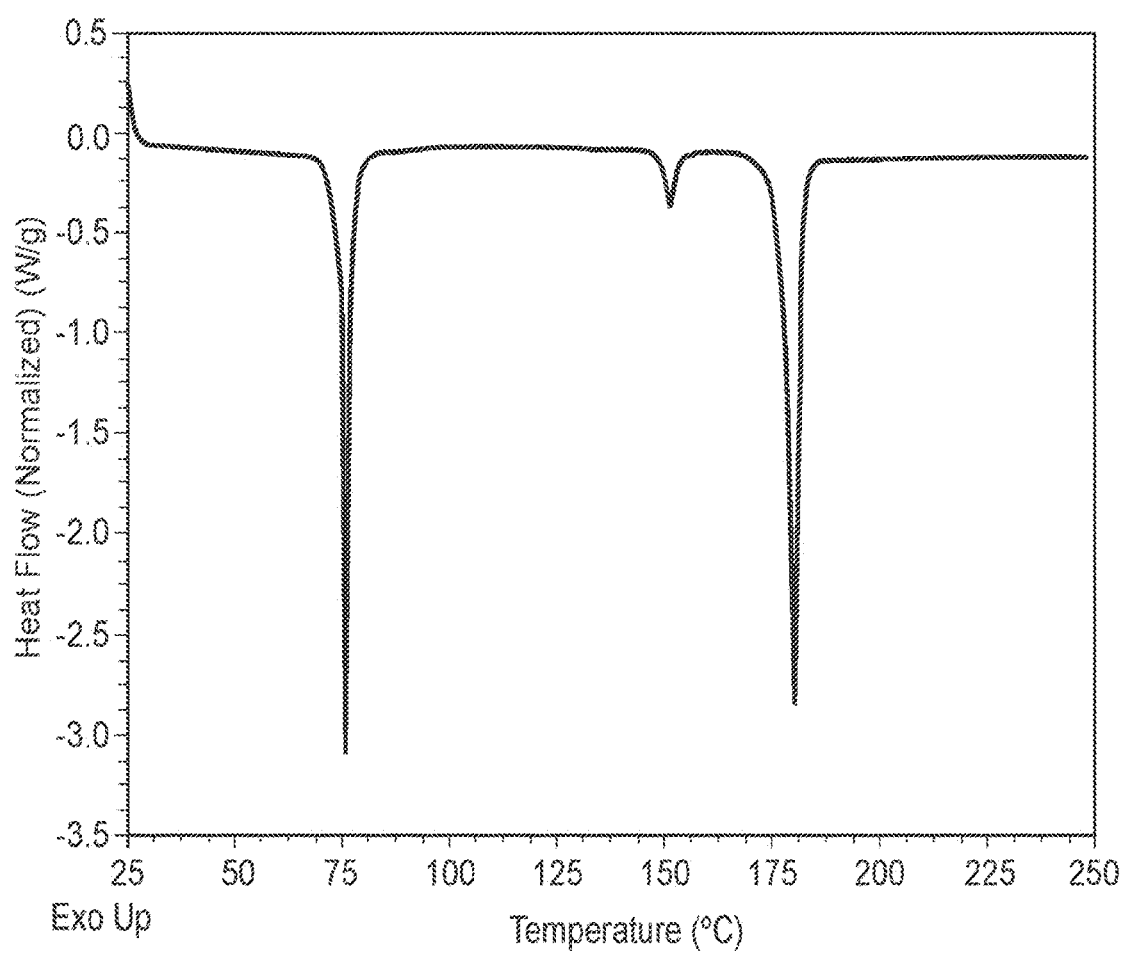
FIG. 21 depicts a DSC thermograph of the crystalline form of Compound A and dichloromethane.

Differential scanning calorimetry (DSC) thermographs were obtained, as set forth in the Examples, for the dichloromethane solvate. The DSC curve indicates an endothermic transition at about 76° C.±3° C. Thus, in some embodiments, the dichloromethane solvate can be characterized by a DSC thermograph having a desolvation endotherm with an onset in a range of about 70° C. to about 80° C. For example, in some embodiments the dichloromethane solvate is characterized by DSC, as shown in FIG. 21.

Figure 22:
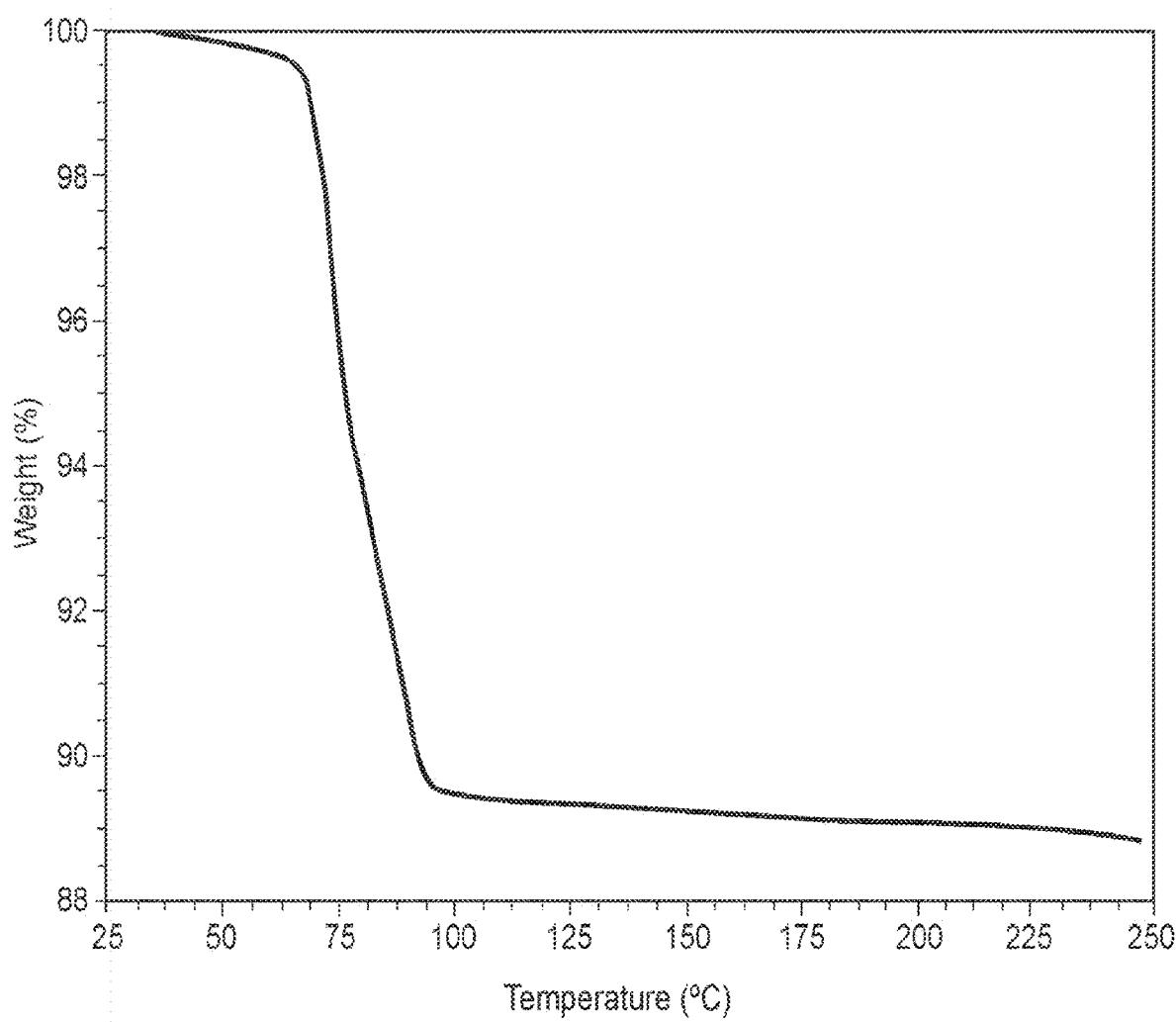
FIG. 22 depicts a TGA trace of the crystalline form of Compound A and dichloromethane.

The dichloromethane solvate also can be characterized by thermogravimetric analysis (TGA). Thus, the dichloromethane solvate can be characterized by a weight loss in a range of about 10% to about 12% with an onset temperature in a range of about 65° C. to about 85° C. For example, the dichloromethane solvate can be characterized by a weight loss of about 10.9%, up to about 200° C. In some embodiments, the dichloromethane solvate has a thermogravimetric analysis substantially as depicted in FIG. 22, wherein by "substantially" is meant that the reported TGA features can vary by about ±5° C.

Nitromethane Solvate

Figure 23:
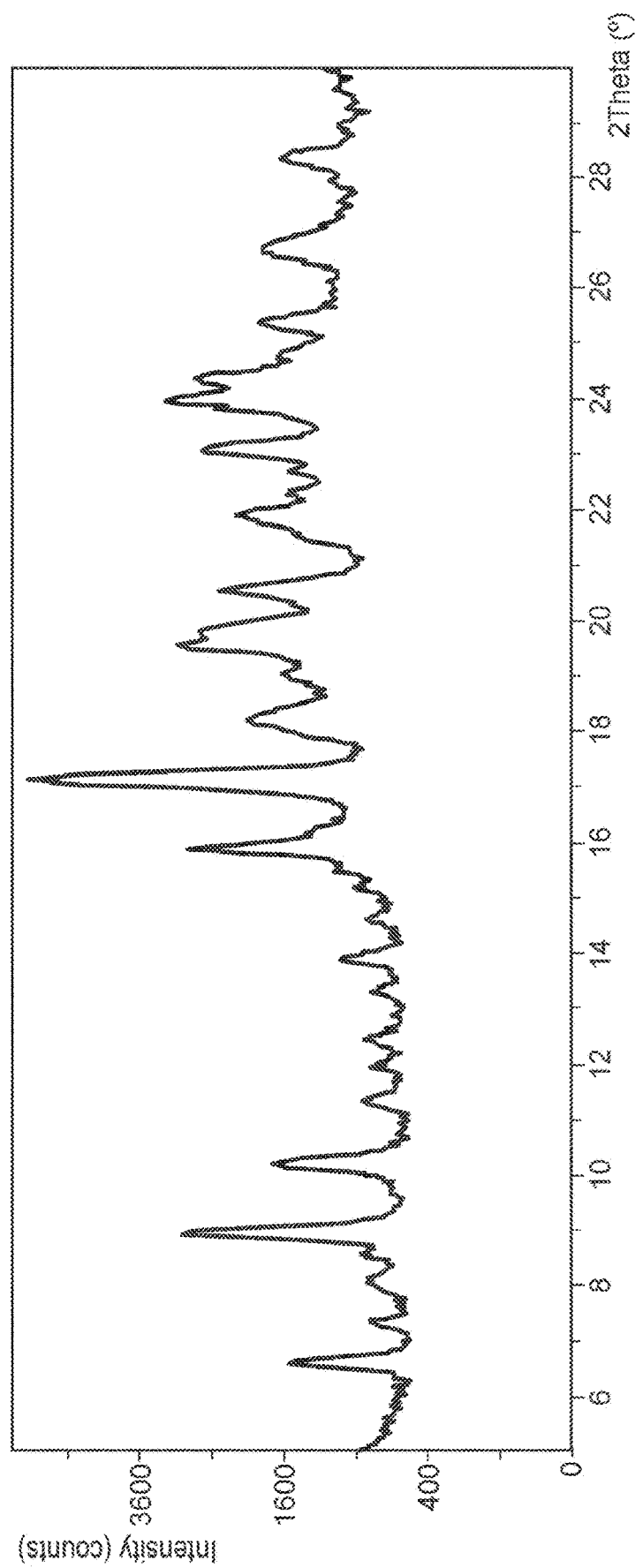
FIG. 23 depicts an XRPD pattern of the crystalline form of Compound A and nitromethane.

A crystalline form of Compound A and nitromethane ("nitromethane solvate") can be characterized by an X-ray powder diffraction pattern, obtained as set forth in the Examples, having peaks at about 8.94, 15.86, 17.12, 19.51, 19.83, and 24.4±0.2° 2θ using Cu Kα radiation. The nitromethane solvate optionally can be further characterized by an X-ray powder diffraction pattern having additional peaks at about 10.18, 18.16, 20.54, 21.93, 23.06, 23.92, and 25.37±0.2° 2θ using Cu Kα radiation. The nitromethane solvate optionally can be further characterized by an X-ray powder diffraction pattern having additional peaks at about 19.01, 22.68, 26.61, and 28.32±0.2° 2θ using Cu Kα radiation. The nitromethane solvate optionally can be characterized by an X-ray powder diffraction pattern having peaks shown in Table 8 set forth in the Examples. In some embodiments, the nitromethane solvate has an X-ray powder diffraction pattern substantially as shown in FIG. 23, wherein by "substantially" is meant that the reported peaks can vary by about ±0.2°.

Figure 24:
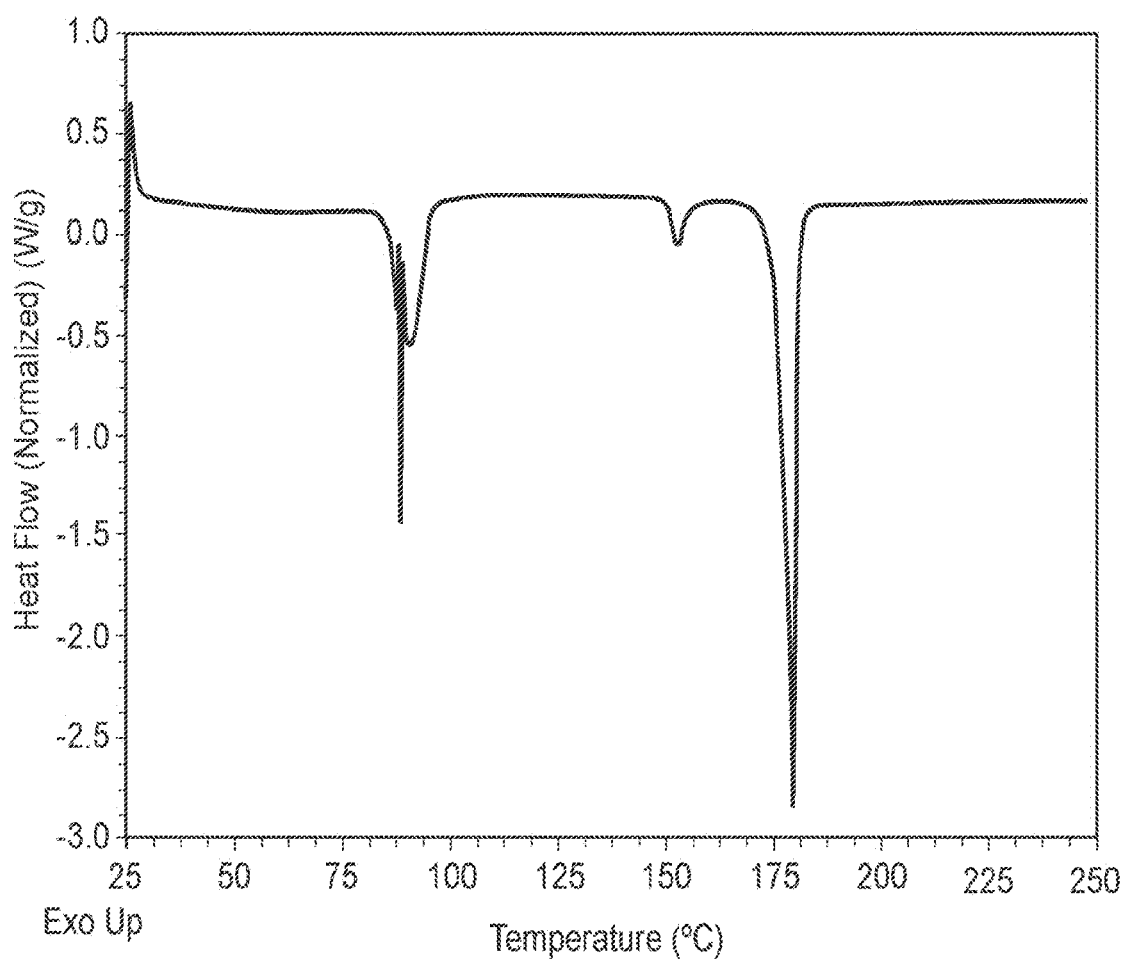
FIG. 24 depicts a DSC thermograph of the crystalline form of Compound A and nitromethane.

Differential scanning calorimetry (DSC) thermographs were obtained, as set forth in the Examples, for the nitromethane solvate. The DSC curve indicates an endothermic transition at about 89° C.±3° C. Thus, in some embodiments, the nitromethane solvate can be characterized by a DSC thermograph having a desolvation endotherm with an onset in a range of about 81° C. to about 97° C. For example, in some embodiments the nitromethane solvate is characterized by DSC, as shown in FIG. 24.

Figure 25:
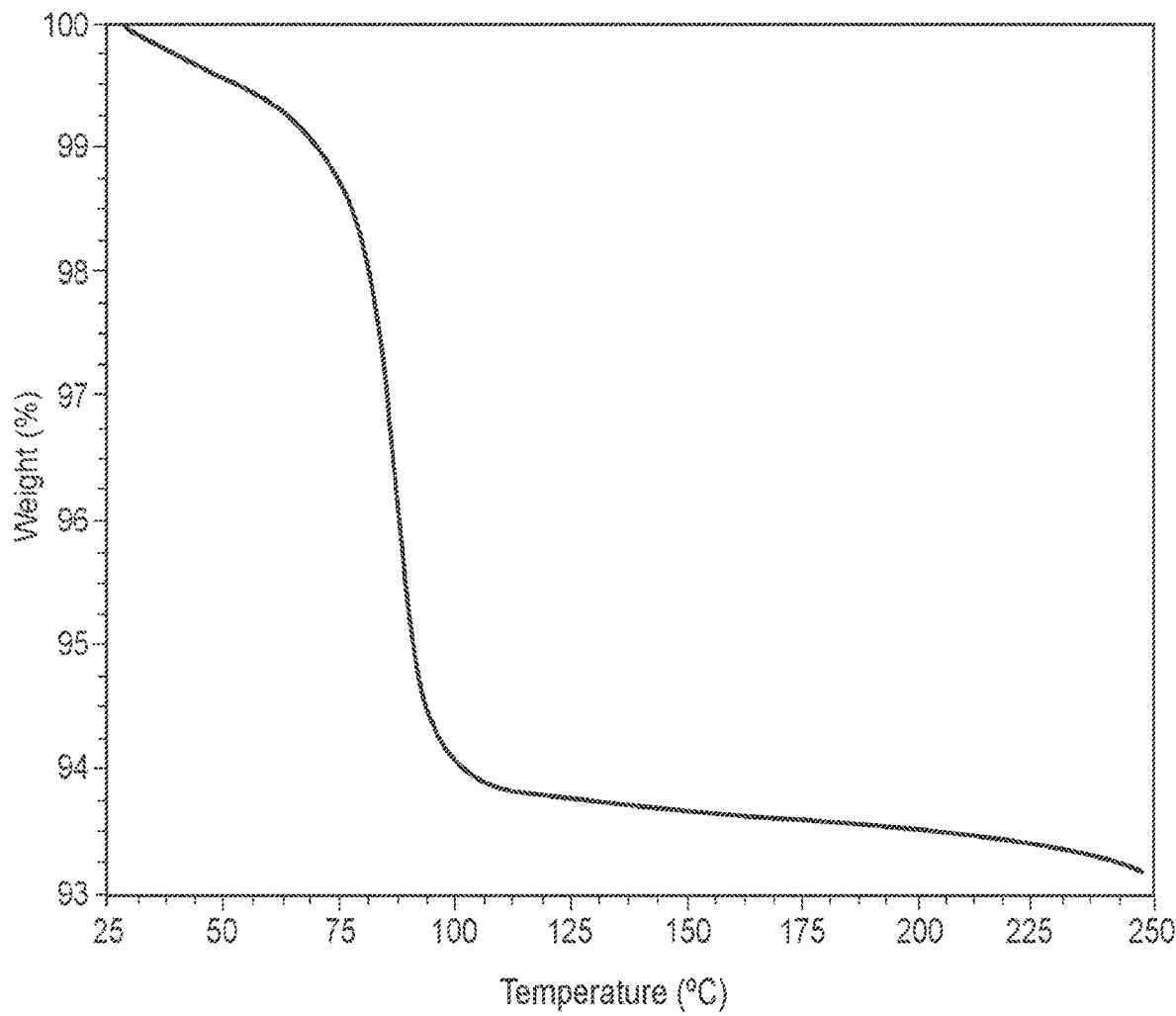
FIG. 25 depicts a TGA trace of the crystalline form of Compound A and nitromethane.

The nitromethane solvate also can be characterized by thermogravimetric analysis (TGA). Thus, the nitromethane solvate can be characterized by a weight loss in a range of about 6% to about 7% with an onset temperature in a range of about 60° C. to about 80° C. For example, the nitromethane solvate can be characterized by a weight loss of about 6.5%, up to about 200° C. In some embodiments, the nitromethane solvate has a thermogravimetric analysis substantially as depicted in FIG. 25, wherein by "substantially" is meant that the reported TGA features can vary by about ±5° C.

Hexafluoro-2-Propanol Solvate

Figure 26:
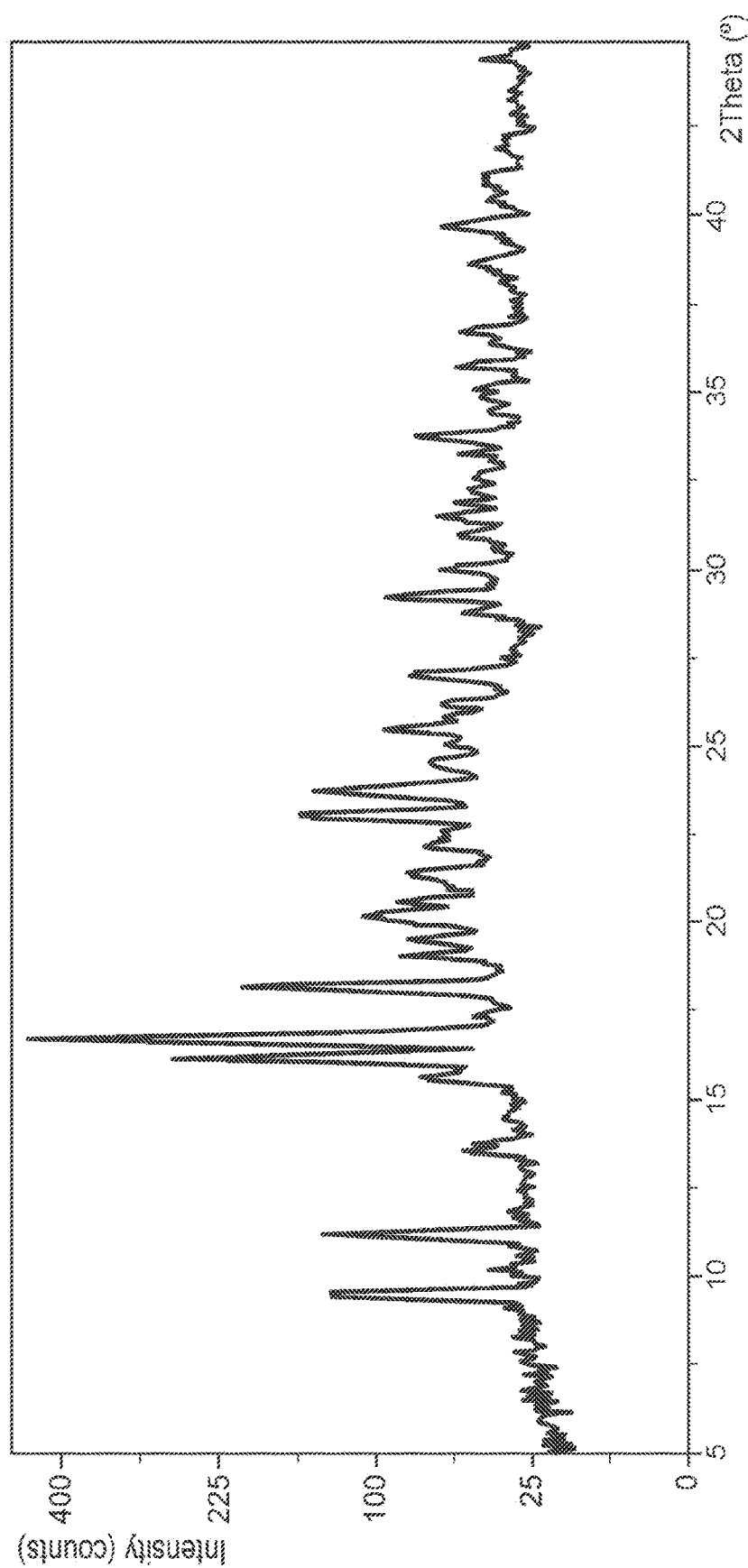
FIG. 26 depicts an XRPD pattern of the crystalline form of Compound A and hexafluoro-2-propanol.

A crystalline form of Compound A and hexafluoro-2-propanol ("hexafluoro-2-propanol solvate") can be characterized by an X-ray powder diffraction pattern, obtained as set forth in the Examples, having peaks at about 16.17, 16.70, 18.20, and 23.03±0.2° 2θ using Cu Kα radiation. The hexafluoro-2-propanol solvate optionally can be further characterized by an X-ray powder diffraction pattern having additional peaks at about 9.49, 11.20, 20.18, 21.39 23.74, 25.46, 27.00, 29.24, and 33.76±0.2° 2θ using Cu Kα radiation. The hexafluoro-2-propanol solvate optionally can be characterized by an X-ray powder diffraction pattern having peaks shown in Table 9 set forth in the Examples. In some embodiments, the hexafluoro-2-propanol solvate has an X-ray powder diffraction pattern substantially as shown in FIG. 26, wherein by "substantially" is meant that the reported peaks can vary by about ±0.2°.

Figure 27:
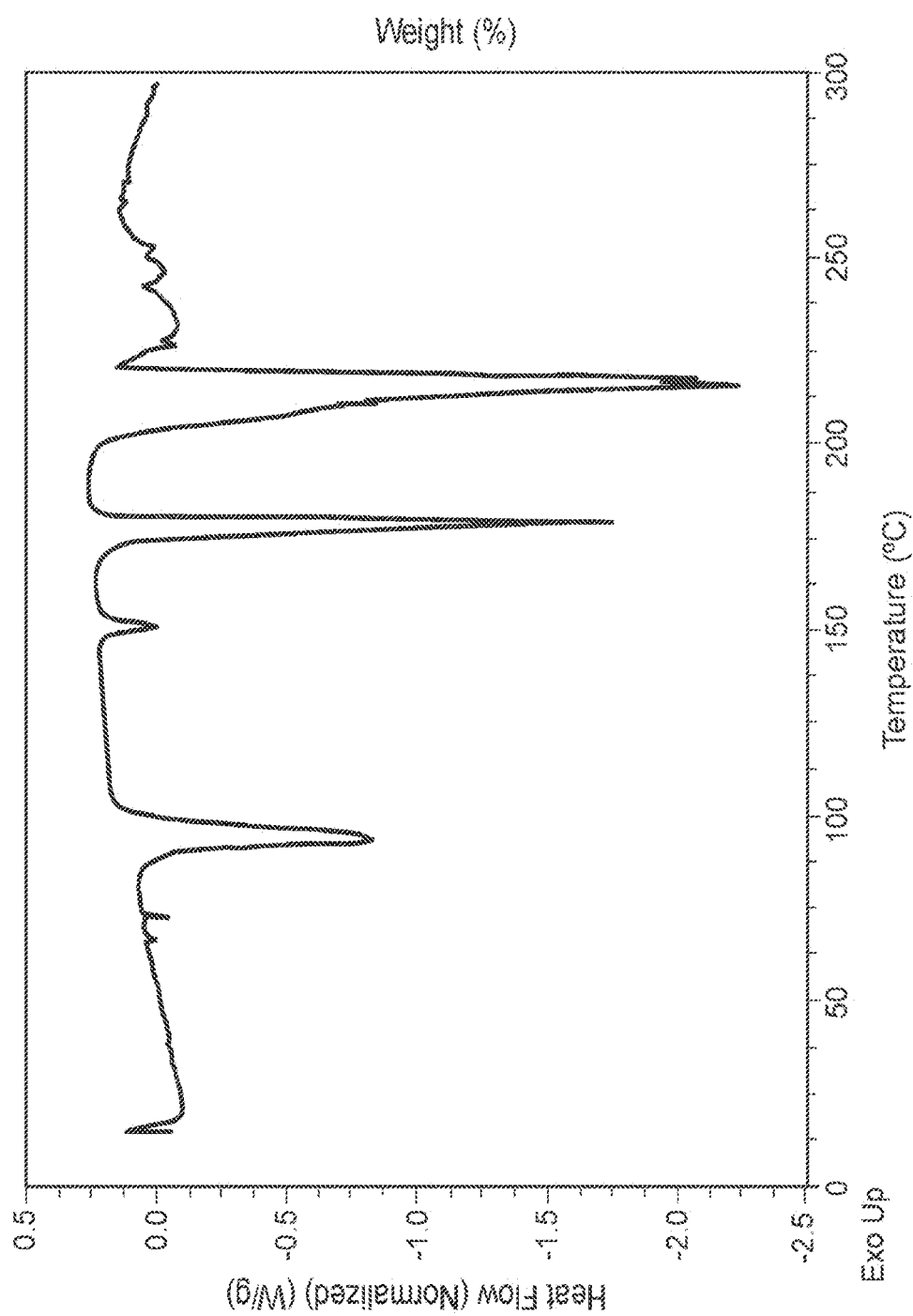
FIG. 27 depicts a DSC thermograph of the crystalline form of Compound A and hexafluoro-2-propanol.

Differential scanning calorimetry (DSC) thermographs were obtained, as set forth in the Examples, for the hexafluoro-2-propanol solvate. The DSC curve indicates an endothermic transition at about 90° C.±3° C. Thus, in some embodiments, the hexafluoro-2-propanol solvate can be characterized by a DSC thermograph having a decomposition endotherm with an onset in a range of about 85° C. to about 95° C. For example, in some embodiments the hexafluoro-2-propanol solvate is characterized by DSC, as shown in FIG. 27.

Figure 28:
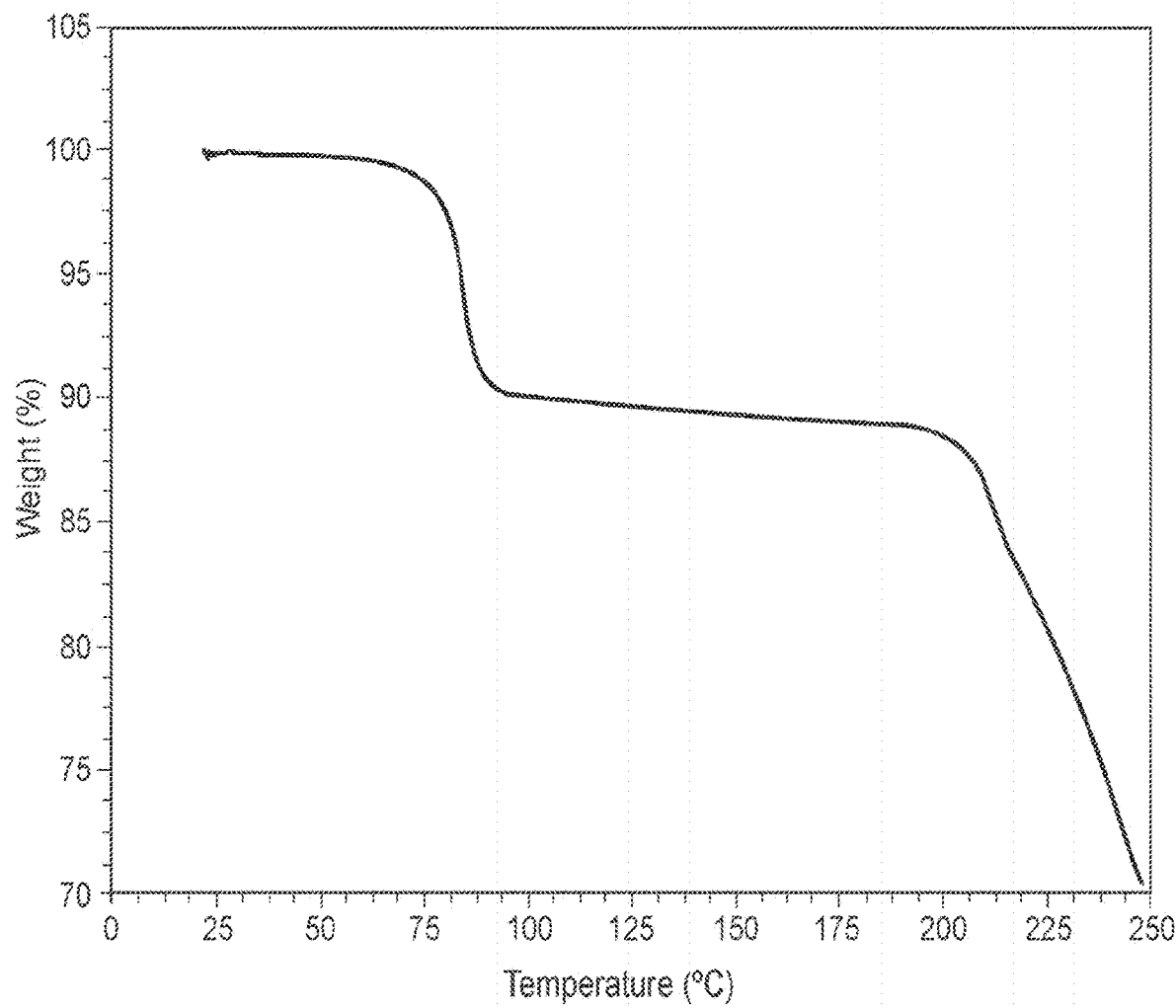
FIG. 28 depicts a TGA trace of the crystalline form of Compound A and hexafluoro-2-propanol.

The hexafluoro-2-propanol solvate also can be characterized by thermogravimetric analysis (TGA). Thus, the hexafluoro-2-propanol solvate can be characterized by a weight loss in a range of about 9.4% to about 10.4% with an onset temperature in a range of about 75° C. to about 85° C. For example, the hexafluoro-2-propanol solvate can be characterized by a weight loss of about 9.9%, up to about 200° C. In some embodiments, the hexafluoro-2-propanol solvate has a thermogravimetric analysis substantially as depicted in FIG. 28, wherein by "substantially" is meant that the reported TGA features can vary by about ±5° C.

Compound A Cocrystals

Provided herein are cocrystals of Compound A with various coformers. The cocrystals comprise Compound A hydrogen bonded with a coformer. In embodiments, the cocrystal can comprise Compound A and the coformer in a molar ratio of 10:1 to 1:10, or 5:1 to 1:5. For example, the cocrystal can comprise Compound A and the coformer in a molar ratio of about 2:1, about 1:1, about 1:1.5, about 1:2, about 1:2.5 about 1:3, about 1:3.5, about 1:4, or about 1:5.

In embodiments, the coformer can comprise benzoic acid, oxalic acid, malonic acid, succinic acid, maleic acid, fumaric acid, glutaric acid, adipic acid, pimelic acid, 3,5-dihydroxybenzoic acid, triflouroacetic acid, 2,5-dihydroxybenzoic acid, 2,4-dihydroxybenzoic acid, m-nitrobenzoic acid, 5-chlorosalicylic acid, saccharin, citric acid, tartaric acid, 2,3-dihydroxybenzoic acid, 3,4-dihydroxybenzoic acid, barbital, 4-hydroxybenzoic acid, 1-hydroxy-2-naphthoic acid, malic acid, 3-hydroxybenzoic acid, 6-hydroxy-2-naphthoic acid, methylgallate, salicyclic acid, 2-hydroxybenzoic acid, formic acid, 3-hydroxy-2-naphthoic acid, sulfacetamide, acetic acid, sulfaproxyline, sulfuric acid, sulfamic acid, ethylenediamine, octadecylamine, glucono-delta lactone, allocitric acid, sucralose, indole, 1-hydroxyethyldene-1,1-diphosphonic acid, skatole, 5-chlorosalicyclic acid, urea, 5-nitroisophthalic acid, trimesic acid, gentisic acid, ketoglutaric acid, adamantine tricarboyxlic acid, t-butylhydroquinone, isocirtric acid, trifluoroethanol, camphoric acid, 4-aminobenzoic acid, 2,6-pyridinedicarboxylic acid, aspirin, butyric acid, formamide, nicotinamide, nitromethane, 1,4-benzoquinone, glycolic acid, terephtalaldehide, dioxane, N-methylpyrrolidone, dimethylsulfoxide, dimethylacetamide, acetone, dimethylformamide, furfural, 4,4'-bipyridine, or a mixture thereof. In embodiments, the coformer can comprise propyl gallate, glycerol, propylene glycol, maltol, urea, or a mixture thereof.

In embodiments, the cocrystals herein may further comprise cocrystallization solvent. The cocrystallization solvent is the solvent from which the cocrystallization of the cocrystal occurs. The cocrystallization solvent can comprise a organic solvent useful in crystallization. Such organic solvents are known to those of skill in the art. In embodiments, the cocrystallization solvent can be ethyl acetate or acetone.

Propyl Gallate Cocrystal

Figure 29:
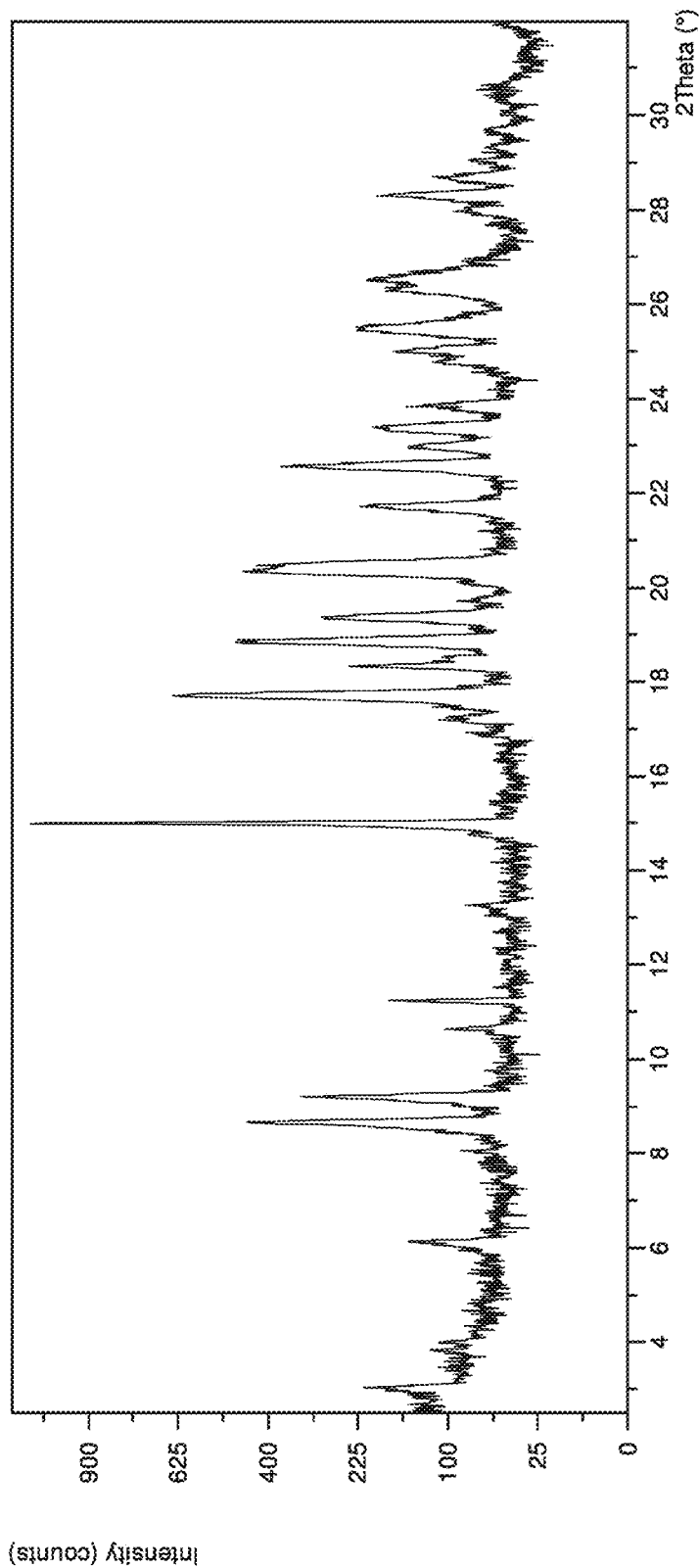
FIG. 29 depicts an XRPD pattern of the cocrystal of Compound A and propyl gallate.

Provided herein is a cocrystal of Compound A and propyl gallate. The cocrystal of Compound A and propyl gallate ("propyl gallate cocrystal") can be characterized by an X-ray powder diffraction pattern, obtained as set forth in the Examples, having peaks at about 8.66, 15.00, 17.72, 18.82, and 20.32±0.2° 2θ using Cu Kα radiation. The propyl gallate cocrystal optionally can be further characterized by an X-ray powder diffraction pattern having additional peaks at about 9.21, 19.36, 20.49, and 22.57±0.2° 2θ using Cu Kα radiation. The propyl gallate cocrystal optionally can be further characterized by an X-ray powder diffraction pattern having additional peaks at about 3.05, 11.24, 18.32, 21.73, 22.98, 23.39, 25.01, 25.51, 26.30, 26.52, and 28.31±0.2° 2θ using Cu Kα radiation. The propyl gallate cocrystal optionally can be characterized by an X-ray powder diffraction pattern having peaks shown in Table 10 set forth in the Examples. In some embodiments, the propyl gallate cocrystal has an X-ray powder diffraction pattern substantially as shown in FIG. 29, wherein by "substantially" is meant that the reported peaks can vary by about ±0.2°.

Figure 30:
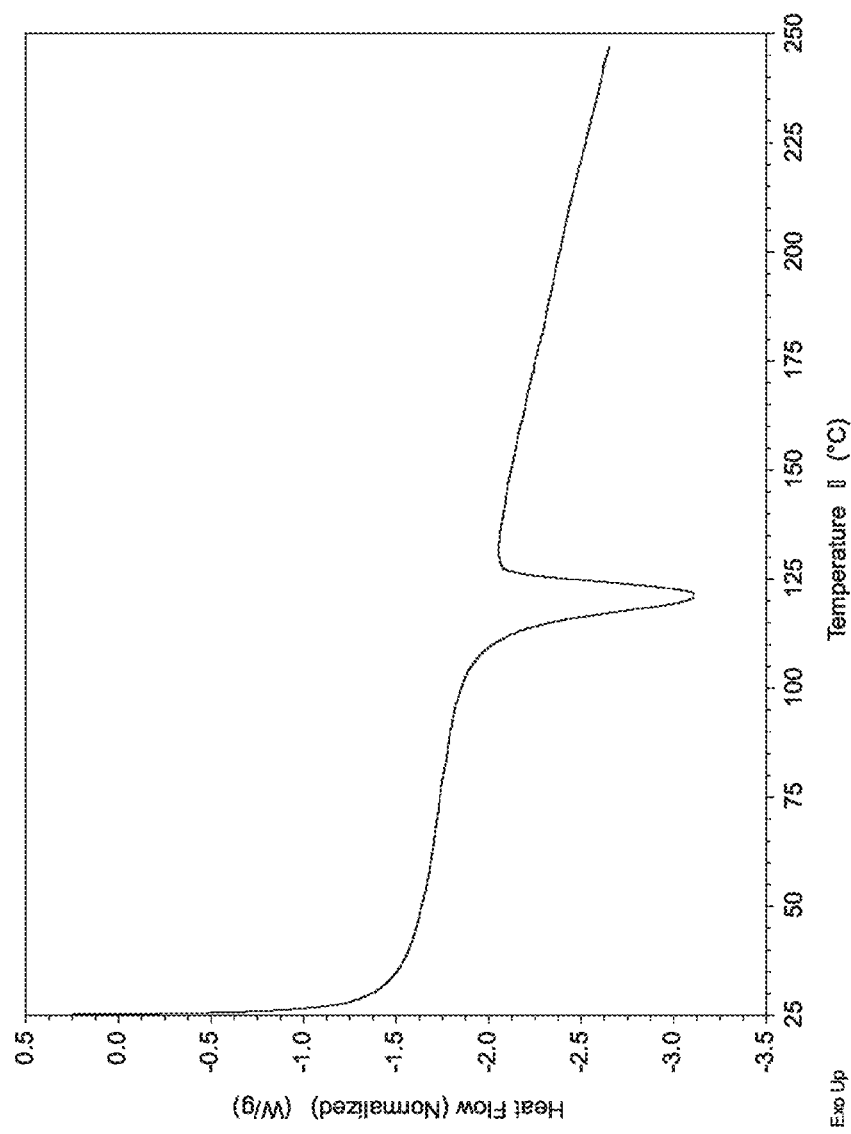
FIG. 30 depicts a DSC thermograph of the cocrystal of Compound A and propyl gallate.

Differential scanning calorimetry (DSC) thermographs were obtained, as set forth in the Examples, for the propyl gallate cocrystal. The DSC curve indicates an endothermic transition at about 121° C.±3° C. Thus, in some embodiments, the propyl gallate cocrystal can be characterized by a DSC thermograph having a melting endotherm with an onset in a range of about 116° C. to about 126° C. For example, in some embodiments the propyl gallate cocrystal is characterized by DSC, as shown in FIG. 30.

Figure 31:
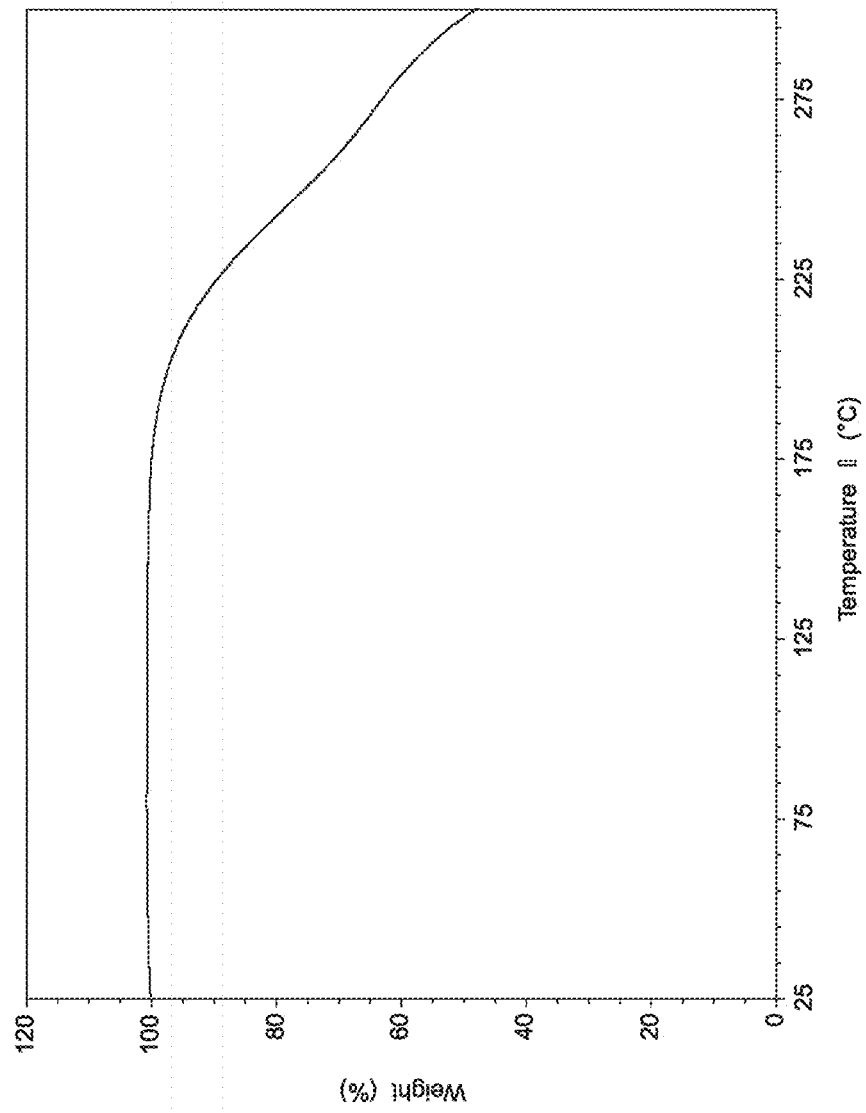
FIG. 31 depicts a TGA trace of the cocrystal of Compound A and propyl gallate.

The propyl gallate cocrystal also can be characterized by thermogravimetric analysis (TGA). Thus, the propyl gallate cocrystal can be characterized by a weight loss in a range of about 25% to about 35% with an onset temperature in a range of about 190° C. to about 210° C. For example, the propyl gallate cocrystal can be characterized by a weight loss of about 29.9%, up to about 260° C. In some embodiments, the propyl gallate cocrystal has a thermogravimetric analysis substantially as depicted in FIG. 31, wherein by "substantially" is meant that the reported TGA features can vary by about ±5° C.

Glycerol Cocrystal

Figure 32:
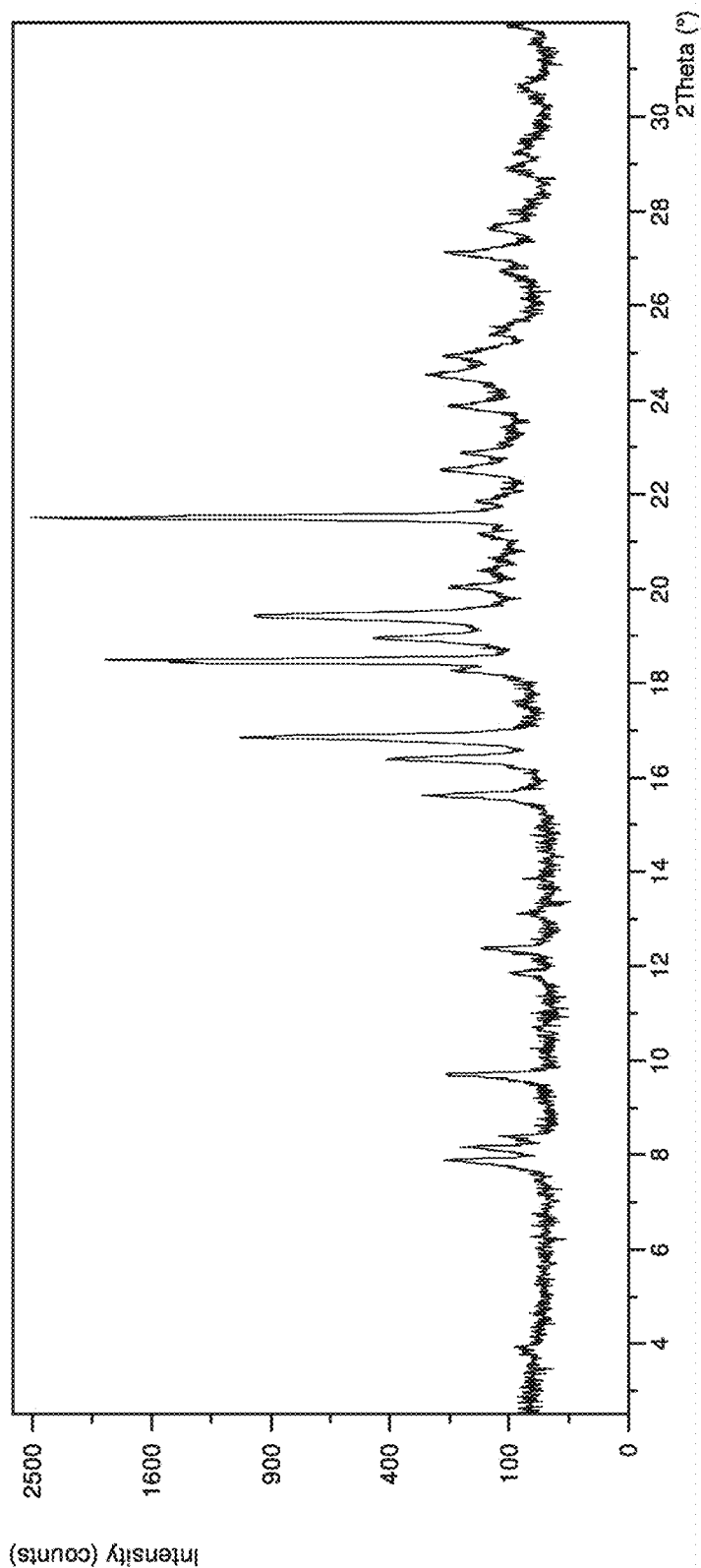
FIG. 32 depicts an XRPD pattern of the cocrystal of Compound A and glycerol.

Provided herein is a cocrystal of Compound A and glycerol. The cocrystal of Compound A and glycerol ("glycerol cocrystal") can be characterized by an X-ray powder diffraction pattern, obtained as set forth in the Examples, having peaks at about 16.84, 18.48, 19.40, and 21.49±0.2° 2θ using Cu Kα radiation. The glycerol cocrystal optionally can be further characterized by an X-ray powder diffraction pattern having additional peaks at about 9.70, 15.60, 16.39, 18.95, 22.51, 24.53, and 24.92±0.2° 2θ using Cu Kα radiation. The glycerol cocrystal optionally can be further characterized by an X-ray powder diffraction pattern having additional peaks at about 8.17, 12.38, 22.87, and 27.61±0.2° 2θ using Cu Kα radiation. The glycerol cocrystal optionally can be characterized by an X-ray powder diffraction pattern having peaks shown in Table 11 set forth in the Examples. In some embodiments, the glycerol cocrystal has an X-ray powder diffraction pattern substantially as shown in FIG. 32, wherein by "substantially" is meant that the reported peaks can vary by about ±0.2°.

Figure 33:
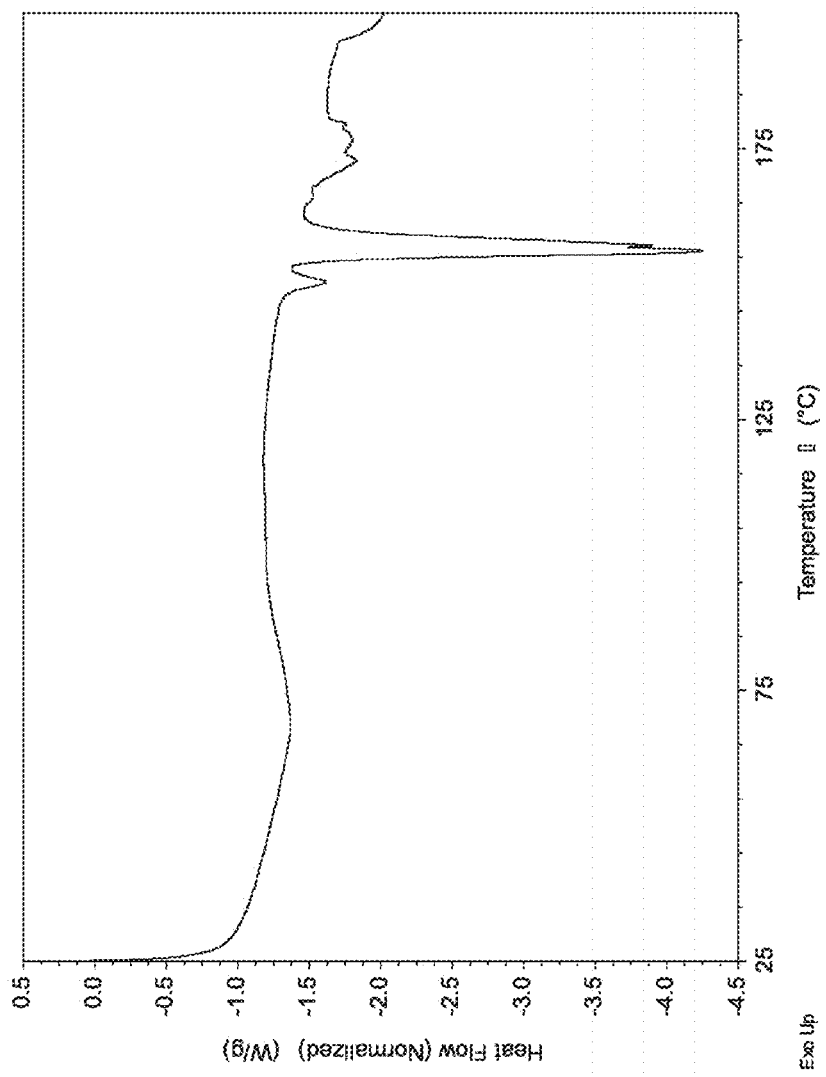
FIG. 33 depicts a DSC thermograph of the cocrystal of Compound A and glycerol.

Differential scanning calorimetry (DSC) thermographs were obtained, as set forth in the Examples, for the glycerol cocrystal. The DSC curve indicates an endothermic transition at about 148° C.±3° C. and 156° C.±3° C. Thus, in some embodiments, the glycerol cocrystal can be characterized by a DSC thermograph having a decomposition endotherm with an onset in a range of about 140° C. to about 151° C. and about 152° C. to 165° C. For example, in some embodiments the glycerol cocrystal is characterized by DSC, as shown in FIG. 33.

Figure 34:
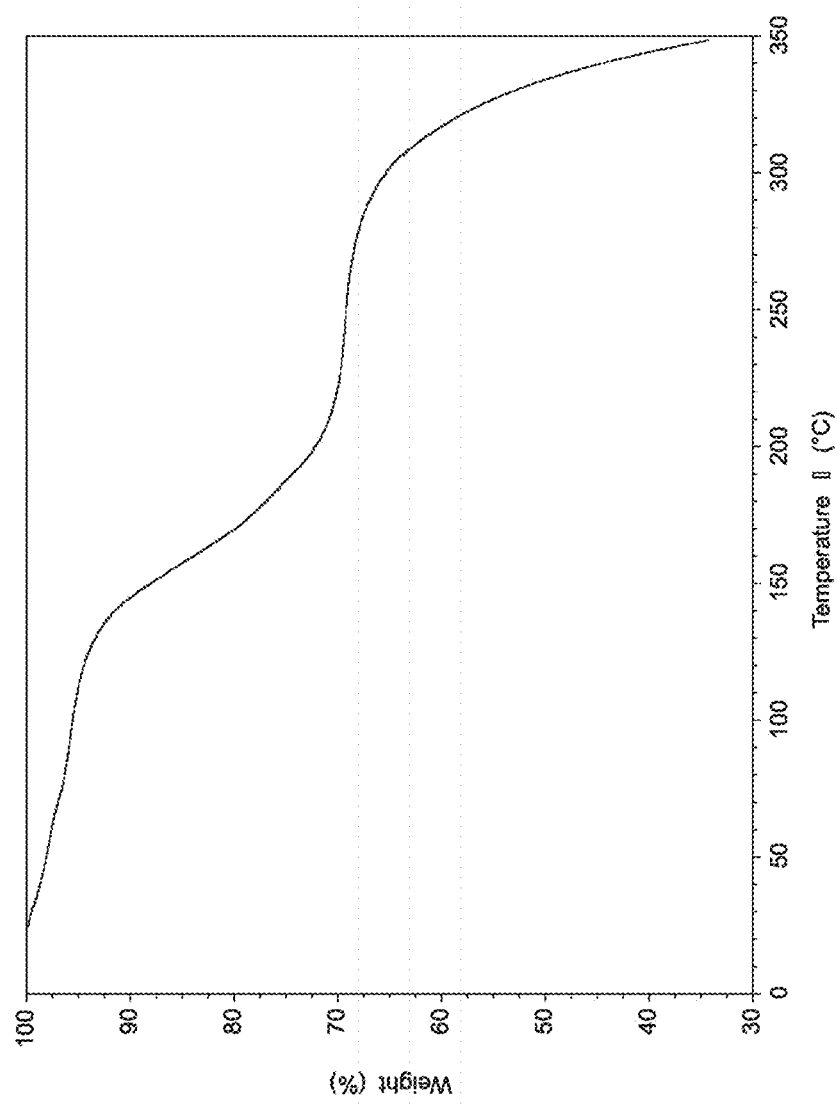
FIG. 34 depicts a TGA trace of the cocrystal of Compound A and glycerol.

The glycerol cocrystal also can be characterized by thermogravimetric analysis (TGA). Thus, the glycerol cocrystal can be characterized by a weight loss in a range of about 20% to about 35% with an onset temperature in a range of about 25° C. to about 35° C. For example, the glycerol cocrystal can be characterized by a weight loss of about 30.5%, up to about 250° C. In some embodiments, the glycerol cocrystal has a thermogravimetric analysis substantially as depicted in FIG. 34, wherein by "substantially" is meant that the reported TGA features can vary by about ±5° C.

Propylene Glycol Cocrystal

Figure 35:
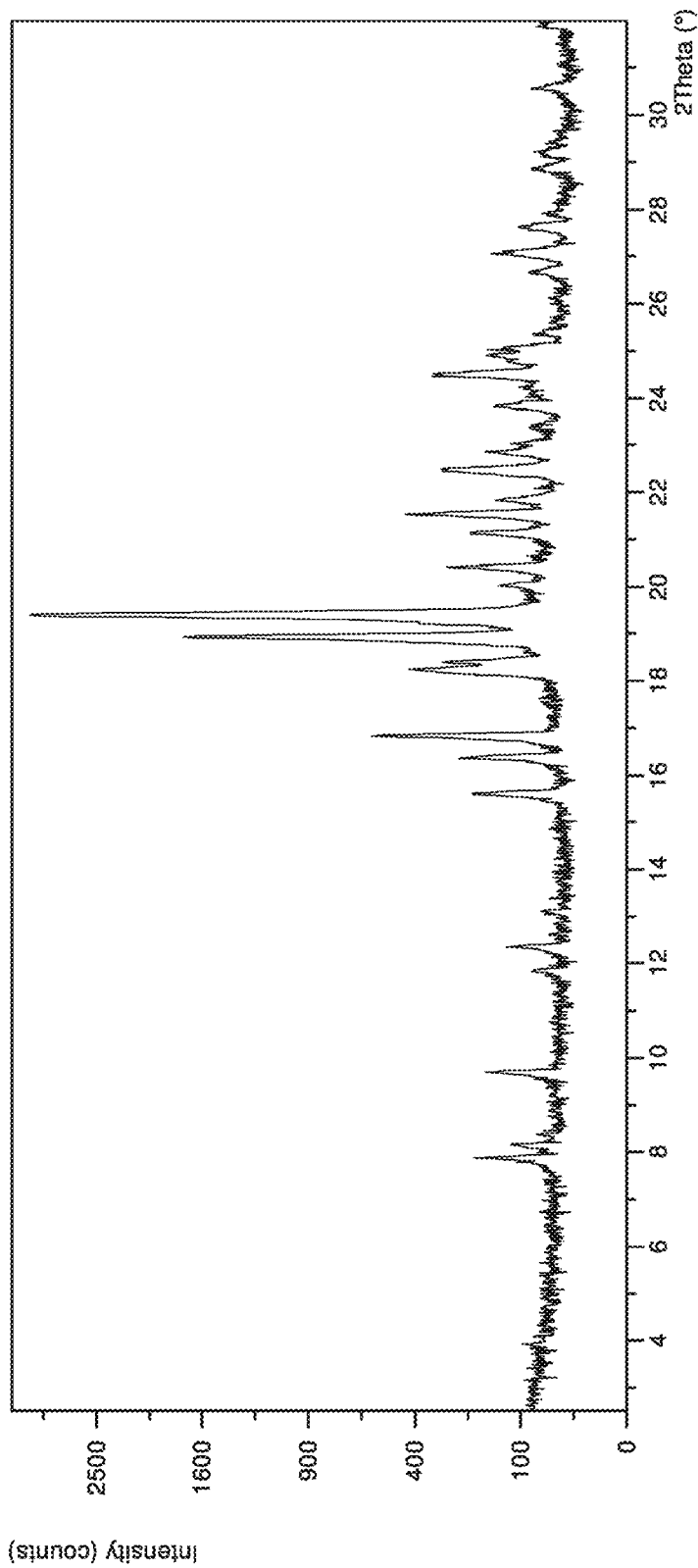
FIG. 35 depicts an XRPD pattern of the cocrystal of Compound A and propylene glycol.

Provided herein is a cocrystal of Compound A and propylene glycol. The cocrystal of Compound A and propylene glycol ("propylene glycol cocrystal") can be characterized by an X-ray powder diffraction pattern, obtained as set forth in the Examples, having peaks at about 16.82, 18.26, 18.93, 19.37, and 21.52±0.2° 2θ using Cu Kα radiation. The propylene glycol cocrystal optionally can be further characterized by an X-ray powder diffraction pattern having additional peaks at about 7.87, 15.61, 16.36, 18.39, 20.39, 21.12, 22.47, and 24.46±0.2° 2θ using Cu Kα radiation. The propylene glycol cocrystal optionally can be further characterized by an X-ray powder diffraction pattern having additional peaks at about 9.69, 20.02, 21.83, 22.85, 23.84, 25.05, and 27.07±0.2° 2θ using Cu Kα radiation. The propylene glycol cocrystal optionally can be characterized by an X-ray powder diffraction pattern having peaks shown in Table 12 set forth in the Examples. In some embodiments, the propylene glycol cocrystal has an X-ray powder diffraction pattern substantially as shown in FIG. 35, wherein by "substantially" is meant that the reported peaks can vary by about ±0.2°.

Figure 36:
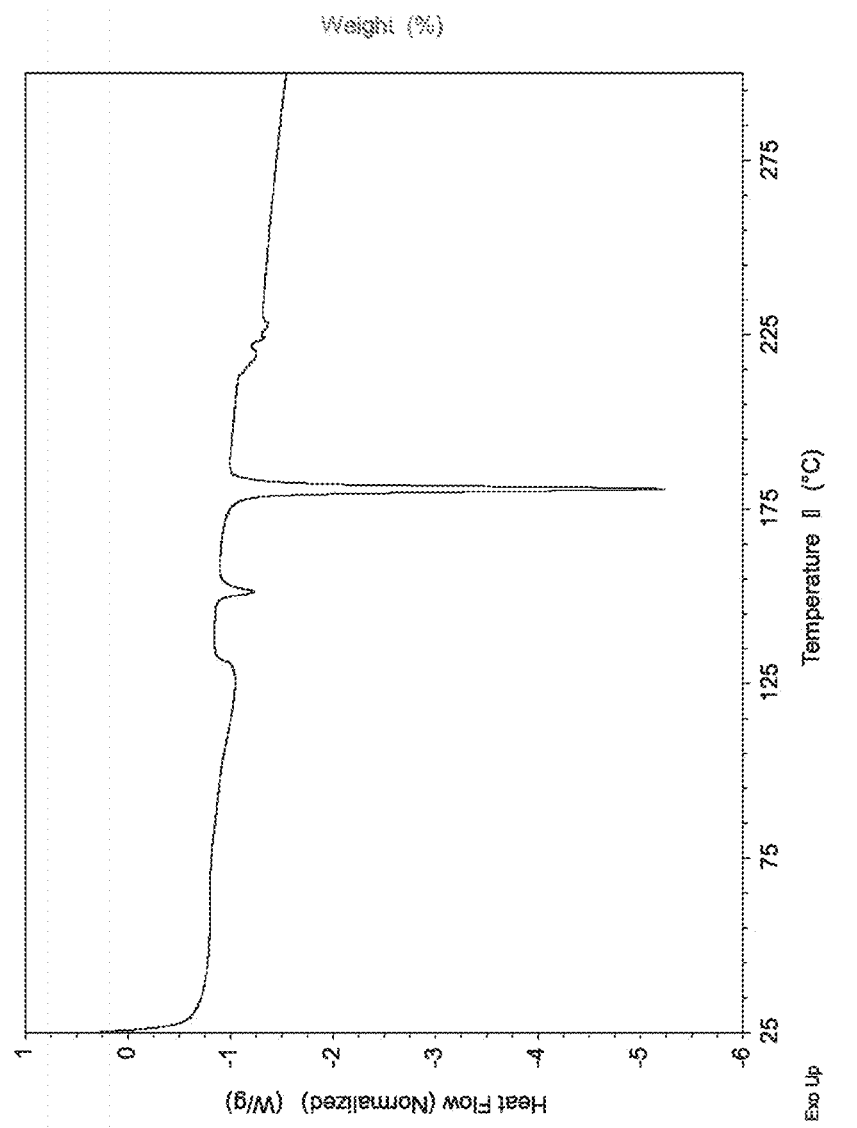
FIG. 36 depicts a DSC thermograph of the cocrystal of Compound A and propylene glycol.

Differential scanning calorimetry (DSC) thermographs were obtained, as set forth in the Examples, for the propylene glycol cocrystal. The DSC curve indicates a broad endothermic transition at about 89° C.±3° C. to 124° C.±3° C. Thus, in some embodiments, the propylene glycol cocrystal can be characterized by a DSC thermograph having a decomposition endotherm with an onset in a range of about 80° C. to about 135° C. For example, in some embodiments the propylene glycol cocrystal is characterized by DSC, as shown in FIG. 36.

Figure 37:
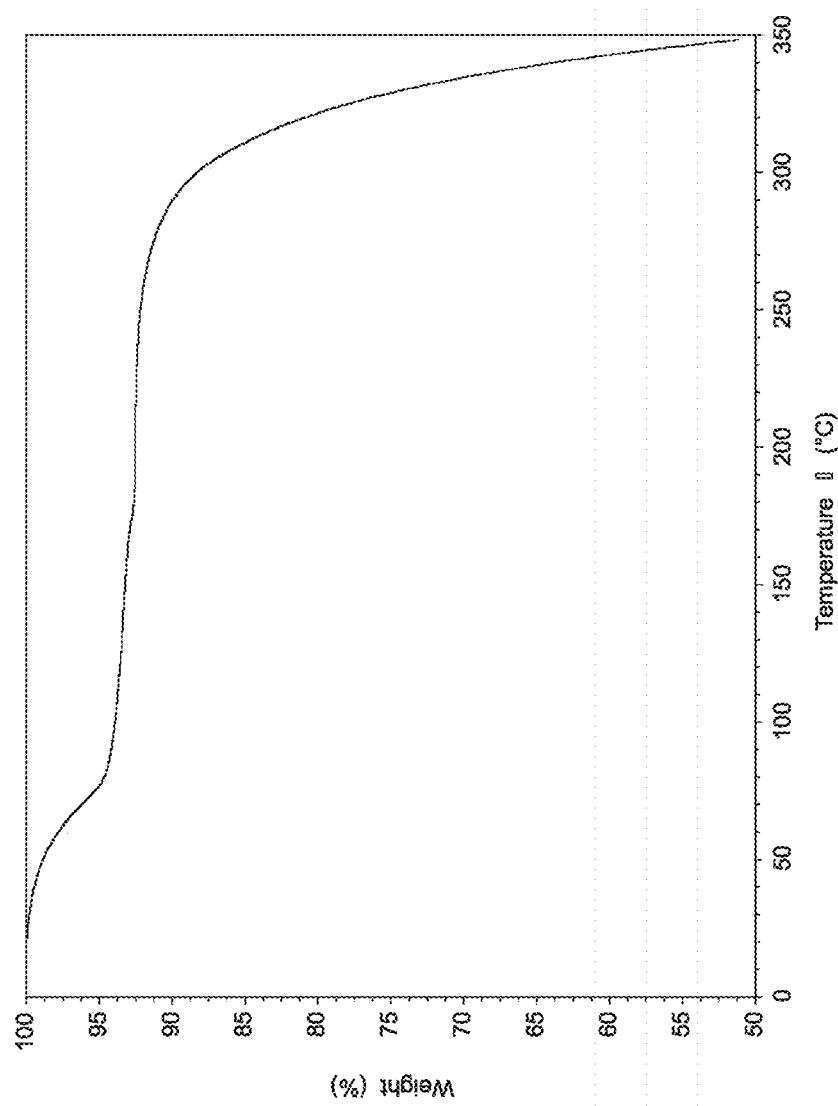
FIG. 37 depicts a TGA trace of the cocrystal of Compound A and propylene glycol.

The propylene glycol cocrystal also can be characterized by thermogravimetric analysis (TGA). Thus, the propylene glycol cocrystal can be characterized by a weight loss in a range of about 5.5% to about 8% with an onset temperature in a range of about 30° C. to about 50° C. For example, the propylene glycol cocrystal can be characterized by a weight loss of about 7.3%, up to about 200° C. In some embodiments, the propylene glycol cocrystal has a thermogravimetric analysis substantially as depicted in FIG. 37, wherein by "substantially" is meant that the reported TGA features can vary by about ±5° C.

Maltol Cocrystal

Figure 38:
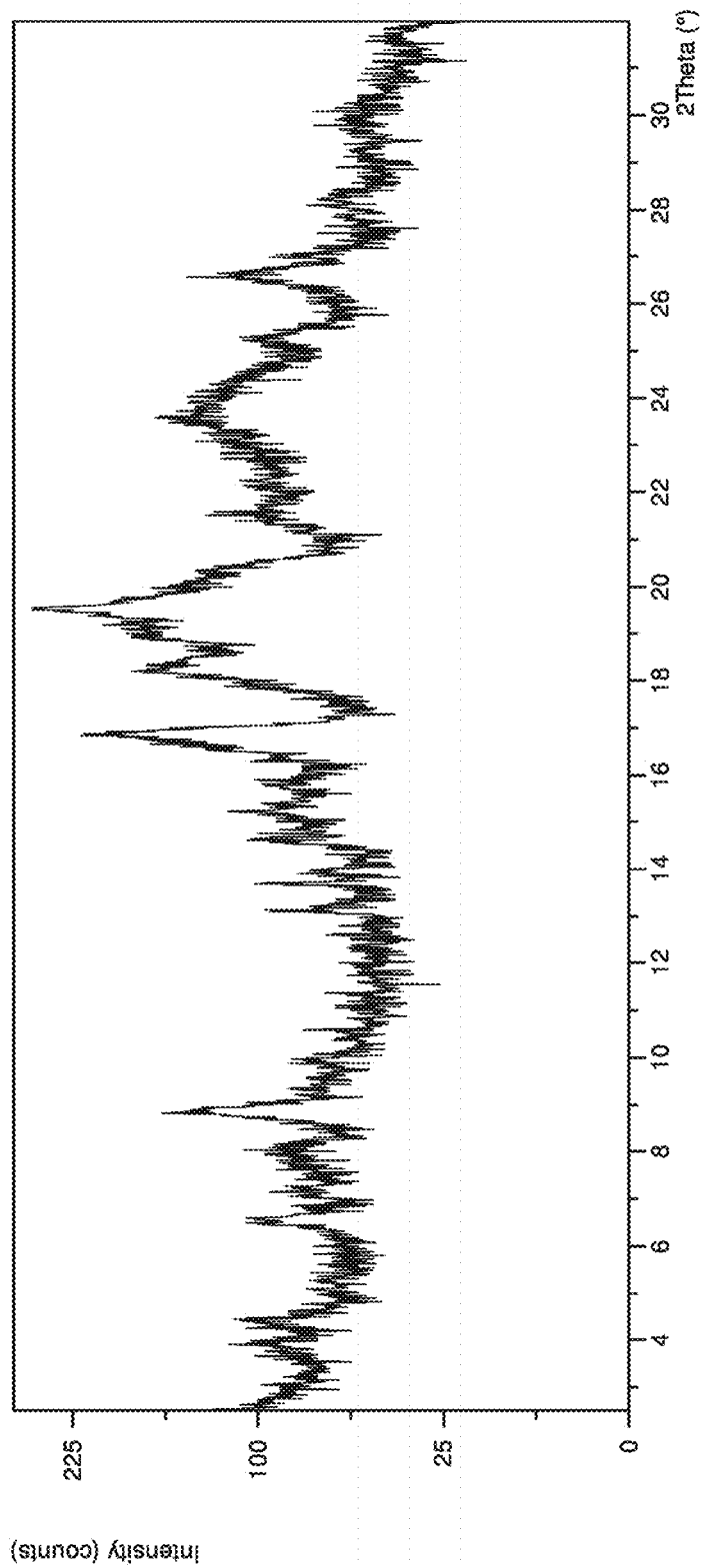
FIG. 38 depicts an XRPD pattern of the cocrystal of Compound A and maltol.

Provided herein is a cocrystal of Compound A and maltol. The cocrystal of Compound A and maltol ("maltol cocrystal") can be characterized by an X-ray powder diffraction pattern, obtained as set forth in the Examples, having peaks at about 16.85, 18.18, 19.53, and 23.54±0.2° 2θ using Cu Kα radiation. The maltol cocrystal optionally can be further characterized by an X-ray powder diffraction pattern having additional peaks at about 6.58, 8.86, 13.68, 14.60, 15.25, 21.52, 25.26, and 26.63±0.2° 2θ using Cu Kα radiation. The maltol cocrystal optionally can be further characterized by an X-ray powder diffraction pattern having additional peaks at about 4.44, 7.98, and 13.13±0.2° 2θ using Cu Kα radiation. The maltol cocrystal optionally can be characterized by an X-ray powder diffraction pattern having peaks shown in Table 13 set forth in the Examples. In some embodiments, the maltol cocrystal has an X-ray powder diffraction pattern substantially as shown in FIG. 38, wherein by "substantially" is meant that the reported peaks can vary by about ±0.2°.

Figure 39:
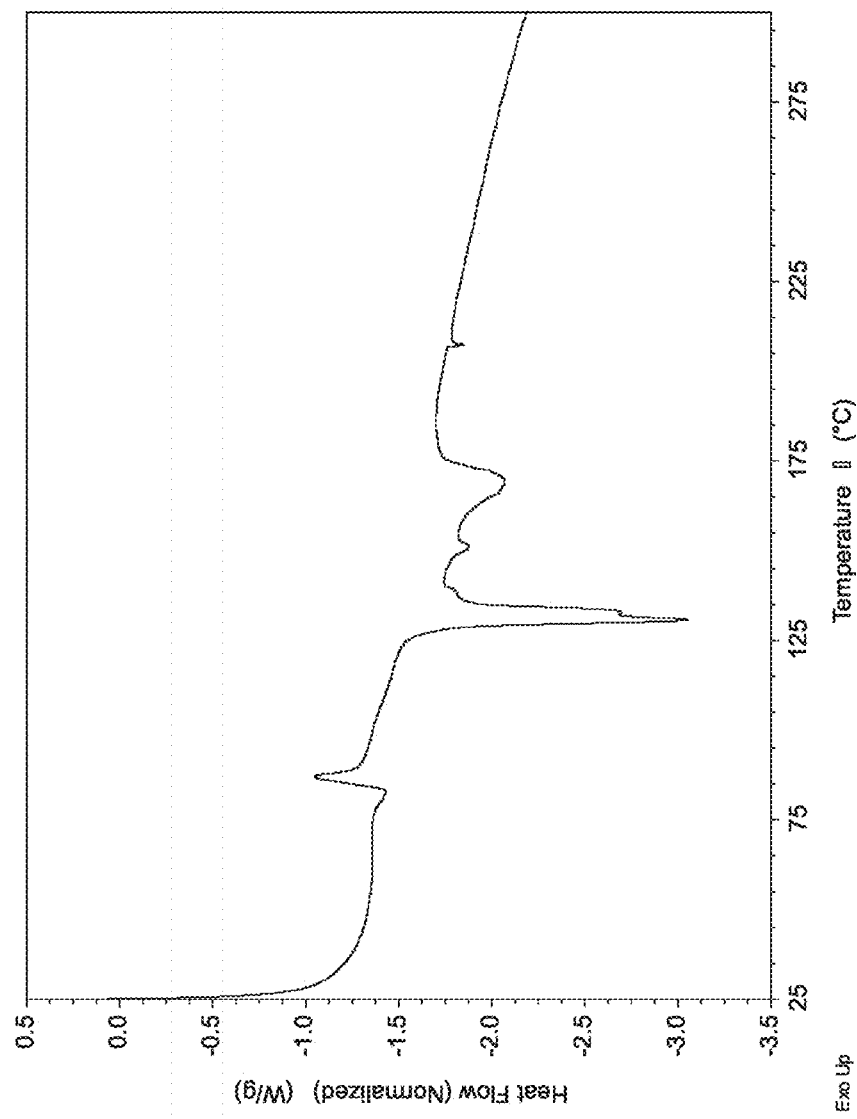
FIG. 39 depicts a DSC thermograph of the cocrystal of Compound A and maltol.

Differential scanning calorimetry (DSC) thermographs were obtained, as set forth in the Examples, for the maltol cocrystal. The DSC curve indicates a broad endothermic transition at about 130° C.±3° C. Thus, in some embodiments, the maltol cocrystal can be characterized by a DSC thermograph having a decomposition endotherm with an onset in a range of about 125° C. to about 135° C. For example, in some embodiments the maltol cocrystal is characterized by DSC, as shown in FIG. 39.

Figure 40:
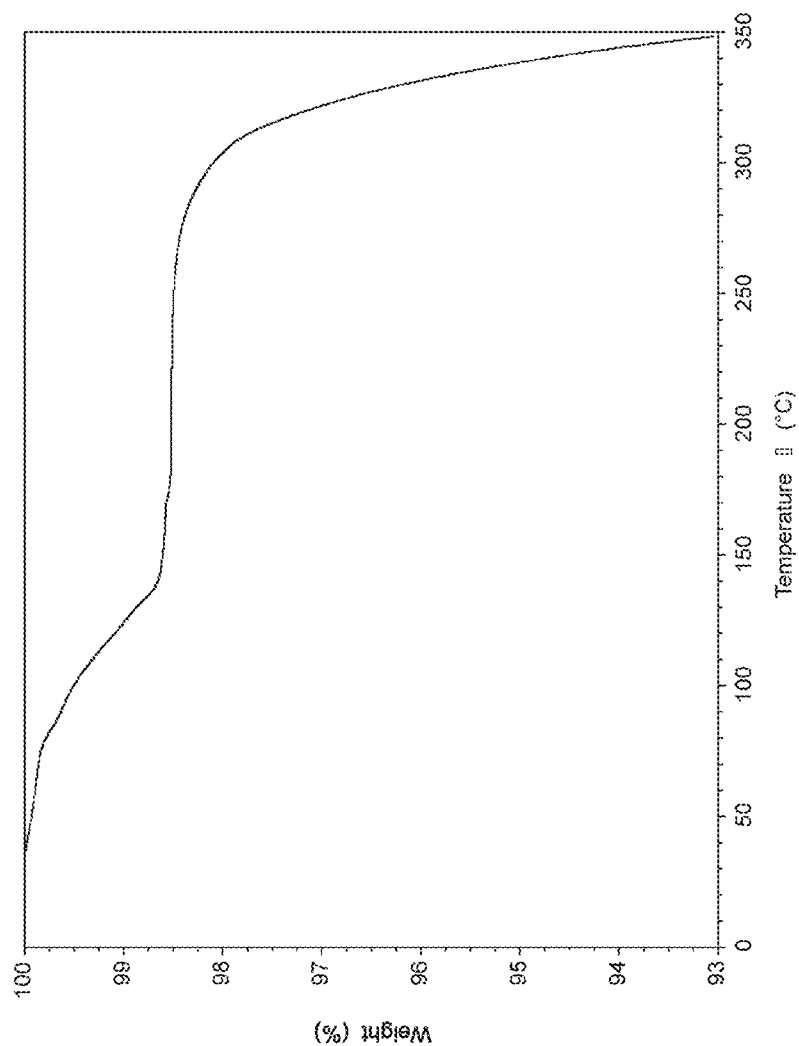
FIG. 40 depicts a TGA trace of the cocrystal of Compound A and maltol.

The maltol cocrystal also can be characterized by thermogravimetric analysis (TGA). Thus, the maltol cocrystal can be characterized by a weight loss in a range of about 1% to about 2.5% with an onset temperature in a range of about 60° C. to about 80° C. For example, the maltol cocrystal can be characterized by a weight loss of about 1.5%, up to about 200° C. In some embodiments, the maltol cocrystal has a thermogravimetric analysis substantially as depicted in FIG. 40, wherein by "substantially" is meant that the reported TGA features can vary by about ±5° C.

Urea Cocrystal

Figure 41:
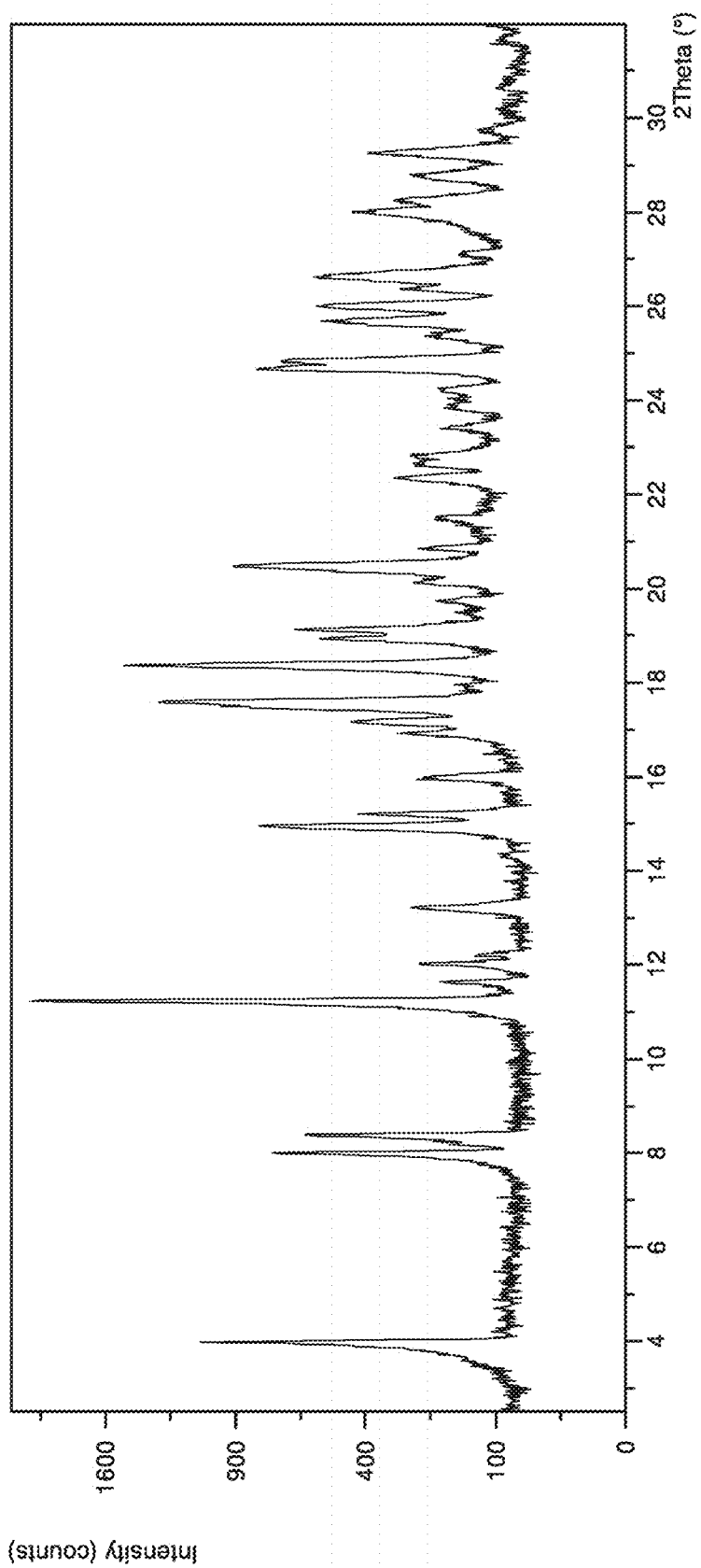
FIG. 41 depicts an XRPD pattern of the cocrystal of Compound A and urea.

Provided herein is a cocrystal of Compound A and urea. The cocrystal of Compound A and urea ("urea cocrystal") can be characterized by an X-ray powder diffraction pattern, obtained as set forth in the Examples, having peaks at about 3.99, 11.24, 17.62, and 18.37±0.2° 2θ using Cu Kα radiation. The urea cocrystal optionally can be further characterized by an X-ray powder diffraction pattern having additional peaks at about 8.01, 8.39, 14.96, 17.47, 18.94, 19.13, 20.51, 24.65, 24.86, 25.70, 25.97, and 26.62±0.2° 2θ using Cu Kα radiation. The urea cocrystal optionally can be further characterized by an X-ray powder diffraction pattern having additional peaks at about 15.21, 16.93, 17.16, 22.37, 26.35, 28.01, 28.26, 28.77, and 29.25±0.2° 2θ using Cu Kα radiation. The urea cocrystal optionally can be characterized by an X-ray powder diffraction pattern having peaks shown in Table 14 set forth in the Examples. In some embodiments, the urea cocrystal has an X-ray powder diffraction pattern substantially as shown in FIG. 41, wherein by "substantially" is meant that the reported peaks can vary by about ±0.2°.

Figure 42:
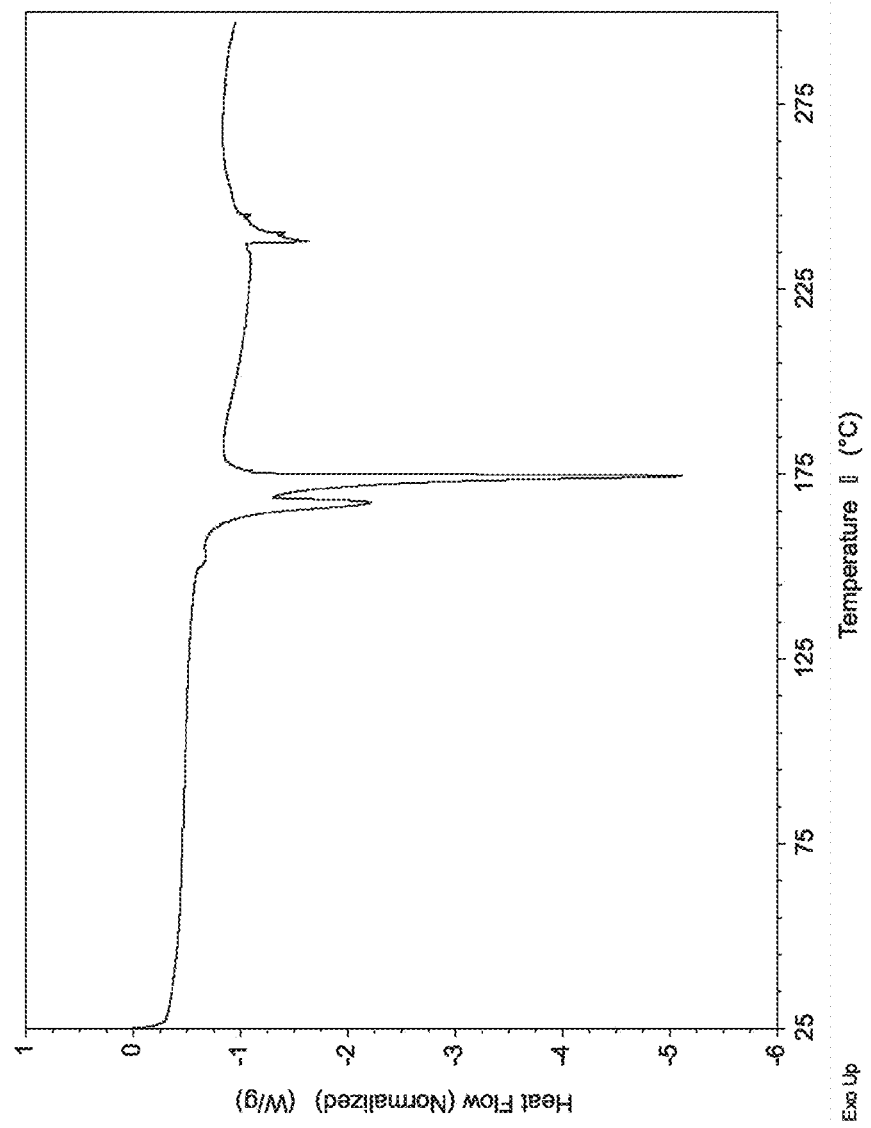
FIG. 42 depicts a DSC thermograph of the cocrystal of Compound A and urea.

Differential scanning calorimetry (DSC) thermographs were obtained, as set forth in the Examples, for the urea cocrystal. The DSC curve indicates a broad endothermic transition at about 167° C.±3° C. and 174° C.±3° C. Thus, in some embodiments, the urea cocrystal can be characterized by a DSC thermograph having a decomposition endotherm with an onset in a range of about 160° C. to about 170° C. and about 171° C. to about 180° C. For example, in some embodiments the urea cocrystal is characterized by DSC, as shown in FIG. 42.

Figure 43:
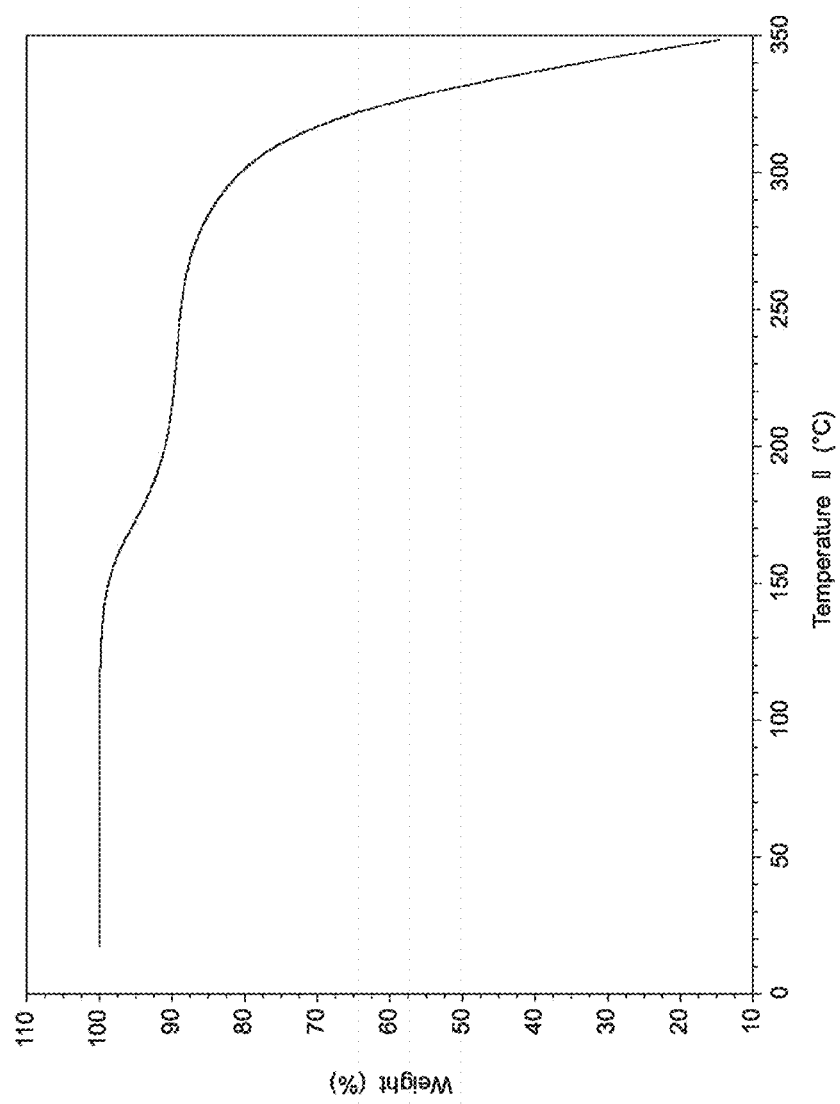
FIG. 43 depicts a TGA trace of the cocrystal of Compound A and urea.

The urea cocrystal also can be characterized by thermogravimetric analysis (TGA). Thus, the urea cocrystal can be characterized by a weight loss in a range of about 9.6% to about 11.6% with an onset temperature in a range of about 145° C. to about 165° C. For example, the urea cocrystal can be characterized by a weight loss of about 10.6%, up to about 225° C. In some embodiments, the urea cocrystal has a thermogravimetric analysis substantially as depicted in FIG. 43, wherein by "substantially" is meant that the reported TGA features can vary by about ±5° C.

Amorphous Form

Figure 44:
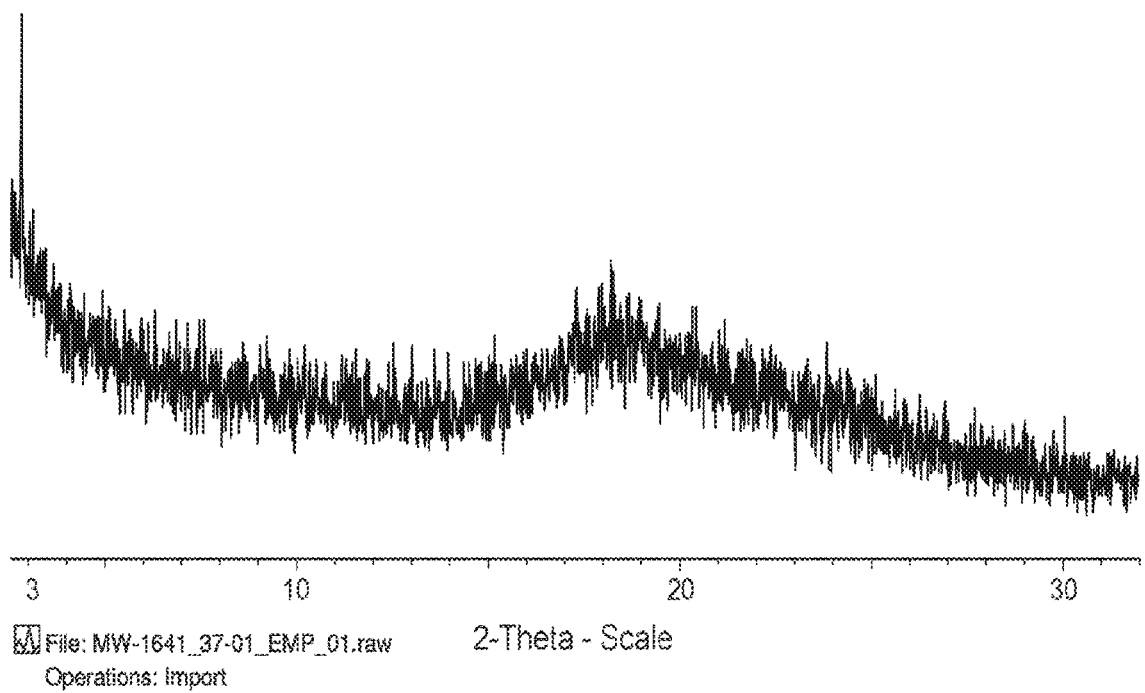
FIG. 44 depicts an XRPD pattern of the amorphous form of Compound A.

Provided herein is an amorphous form of Compound A. In some embodiments, the amorphous form of Compound A has an X-ray powder diffraction pattern substantially as shown in FIG. 44, wherein by "substantially" is meant that the reported peaks can vary by about ±0.2°.

Figure 45:
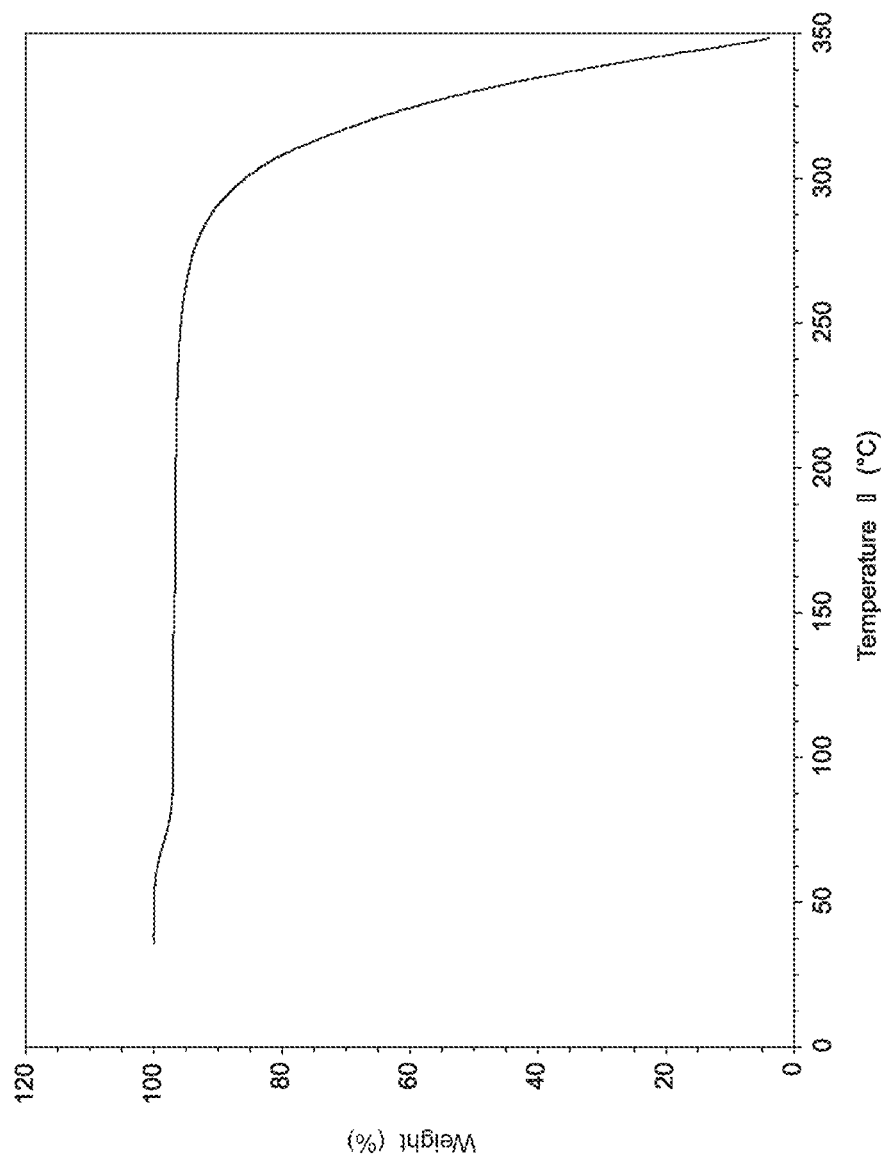
FIG. 45 depicts a TGA trace of the amorphous form of Compound A.

The amorphous form of Compound A also can be characterized by thermogravimetric analysis (TGA). Thus, the amorphous form of Compound A can be characterized by a weight loss in a range of about 2% to about 4% with an onset temperature in a range of about 25° C. to about 55° C. For example, the urea cocrystal can be characterized by a weight loss of about 2.9%, up to about 150° C. In some embodiments, the amorphous form has a thermogravimetric analysis substantially as depicted in FIG. 45, wherein by "substantially" is meant that the reported TGA features can vary by about ±5° C.

Pharmaceutical Compositions

Also provided herein are pharmaceutical compositions comprising a crystalline form and/or cocrystal of Compound A or a salt thereof described herein; and a pharmaceutically acceptable carrier. In embodiments, the carrier can comprise an excipient.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The compositions described herein can be formulated for any form of administration. In various cases, the composition is for oral administration. In various cases, the composition is in tablet form.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffers, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions as excipients.

Examples of pharmaceutically acceptable antioxidants as excipient include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of an injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

In some embodiments, the polymorphs and salts disclosed herein are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety.

The pharmaceutical compositions can be included in a container, pack, or dispenser together with instructions for administration.

Methods of Use

The forms or cocrystals of Compound A or a salt thereof disclosed herein, or the pharmaceutical compositions described herein, may be used in the treatment or prevention of heart failure, including but not limited to: acute (or decompensated) congestive heart failure, and chronic congestive heart failure; particularly diseases associated with systolic heart dysfunction.

Also provided herein are methods of treating or preventing heart failure in a subject in need thereof comprising administering to the subject one or more of the forms or cocrystals of Compound A or a salt thereof disclosed herein, or one or more of the pharmaceutical compositions described herein in an amount effective to treat or prevent heart failure. Further provided are methods for the use of the disclosed forms or cocrystals of Compound A or a salt thereof, or compositions thereof, for the treatment or prevention of heart failure, including but not limited to: acute (or decompensated) congestive heart failure, and chronic congestive heart failure.

Also provided herein is the use of the forms or cocrystals of Compound A or a salt thereof disclosed herein, or the pharmaceutical compositions described herein, in the manufacture of a medicament for the treatment or prevention of heart failure. In some embodiments, the present disclosure provides use of the forms or cocrystals of Compound A or a salt thereof disclosed herein, or the pharmaceutical compositions described herein, in the manufacture of a medicament for the treatment of acute (or decompensated) congestive heart failure, and chronic congestive heart failure.

In some embodiments, the forms or cocrystals of Compound A or a salt thereof disclosed herein are used in the treatment or prevention of heart failure with reduced ejection fraction (HFrEF) or systolic heart failure, dilated cardiomyopathy, postpartum cardiomyopathy, idiopathic cardiomyopathy, pediatric HFrEF, chemotherapy-induced heart failure, heart failure associated with muscular dystrophy, bi-ventricular HFrEF, HFrEF with pulmonary hypertension, heart failure with preserved ejection fraction (HFpEF) with right ventricular dysfunction, pulmonary hypertension with right ventricular dysfunction, scleroderma with pulmonary hypertension, right ventricular dysfunction, Chagas disease, or myocarditis. In some embodiments, provided herein are methods of treating or preventing heart failure with reduced ejection fraction or systolic heart failure, dilated cardiomyopathy, postpartum cardiomyopathy, idiopathic cardiomyopathy, pediatric HFrEF, chemotherapy-induced heart failure, heart failure associated with muscular dystrophy, bi-ventricular HFrEF, HFrEF with pulmonary hypertension, heart failure with preserved ejection fraction (HFpEF) with right ventricular dysfunction, pulmonary hypertension with right ventricular dysfunction, scleroderma with pulmonary hypertension, right ventricular dysfunction, Chagas disease, or myocarditis, which methods comprise administering to a subject in need thereof an effective amount of one or more forms or cocrystals of Compound A or a salt thereof disclosed herein. Also provided herein is the use of one or more forms or cocrystals of Compound A or a salt thereof disclosed herein in the manufacture of a medicament for the treatment or prevention of heart failure with reduced ejection fraction or systolic heart failure, dilated cardiomyopathy, postpartum cardiomyopathy, idiopathic cardiomyopathy, pediatric HFrEF, chemotherapy-induced heart failure, heart failure associated with muscular dystrophy, bi-ventricular HFrEF, HFrEF with pulmonary hypertension, heart failure with preserved ejection fraction (HFpEF) with right ventricular dysfunction, pulmonary hypertension with right ventricular dysfunction, scleroderma with pulmonary hypertension, right ventricular dysfunction, Chagas disease, or myocarditis.

In some embodiments, the dilated cardiomyopathy is selected from the group consisting of genetic dilated cardiomyopathy, peripartum cardiomyopathy (e.g., post-partum cardiomyopathy), idiopathic dilated cardiomyopathy, post-infectious dilated cardiomyopathy, toxin-induced dilated cardiomyopathy, and nutritional deficiency dilated cardiomyopathy. In some embodiments, the pediatric HFrEF occurs in pediatric patients with univentricular hearts or a single ventricle or patients post Fontan or Fontan-Kreutzer procedure. In some embodiments, the pediatric HFrEF is pediatric heart failure associated with congenital heart disease. In some embodiments, the chemotherapy-induced heart failure is selected from the group consisting of chemotherapy-induced left ventricular dysfunction, radiation-induced heart failure, heart failure resulting from anthracycline treatment (including but not limited to doxorubicin, epirubicin, and daunorubicin), heart failure resulting from antiERBB2 treatment (including but not limited to trastuzumab and lapatinib), heart failure resulting from VEGF inhibitor treatment (including but not limited to bevacizumab), and heart failure resulting from tyrosine-kinase inhibitor treatment (including but not limited to imatinib, dasatinib, nilotinim, sorafenib, and sunitinib). In some embodiments, the heart failure associated with muscular dystrophy is selected from the group consisting of heart failure associated with Duchenne muscular dystrophy, heart failure associated with Becker muscular dystrophy, heart failure associated with myotonic dystrophy (e.g., Steinert's disease), heart failure associated with laminopathies such as Emery-Dreifuss muscular dystrophy (EDMD), including both X-linked EDMD and autosomal dominant EDMD, heart failure associated with facioscapulohumeral muscular dystrophy (FSHMD), heart failure associated with Limb-girdle muscular dystrophy, including sarcoglycanopathies and the autosomal dominant form of the disease, and heart failure associated with congenital muscular dystrophy. In some embodiments, the pulmonary hypertension with right ventricular dysfunction is associated with high left ventricular (diastolic) pressure in HFrEF or high left ventricular (diastolic) pressure in HFpEF.

"Treatment" or "treating" includes one or more of: a) inhibiting a disease or disorder; b) slowing or arresting the development of clinical symptoms of a disease or disorder; and/or c) relieving a disease or disorder that is, causing the regression of clinical symptoms. The term covers both complete and partial reduction of the condition or disorder, and complete or partial reduction of clinical symptoms of a disease or disorder. Thus, the forms or cocrystals of Compound A or salt thereof described herein, or the pharmaceutical compositions described herein may prevent an existing disease or disorder from worsening, assist in the management of the disease or disorder, or reduce or eliminate the disease or disorder. "Prevention," that is, causing the clinical symptoms of the disease or disorder not to develop, includes the prophylactic administration of a pharmaceutical formulation described herein to a subject (i.e., an animal, preferably a mammal, most preferably a human) believed to be in need of preventative treatment, such as, for example, chronic heart failure.

EXAMPLES

Methods
X-ray Powder Diffraction (XRPD)
X-ray powder diffraction (XRPD) data were obtained using a PANalytical X'Pert PRO diffractometer. Samples were scanned at ambient temperature in continuous mode from 5-30 or 5-45 degrees (2θ) with step size of 0.0334 degrees at 45 kV and 40 mA with CuKα radiation (1.54 Å). The incident beam path was equipped with a 0.02 rad soller slit, 15 mm mask, 4 degrees fixed anti-scatter slit and a programmable divergence slit. The diffracted beam was equipped with a 0.02 rad soller slit, programmable anti-scatter slit and a 0.02 mm nickel filter. Samples were prepared on a low background sample holder and placed on a spinning stage with a rotation time of 2 s.

Optionally, X-ray powder diffraction (XRPD) data were obtained using a PANalytical Empyrean diffractometer. Samples were scanned at ambient temperature in continuous mode from 2.5-32 degrees (2θ) with step size of 0.0131 degrees at 35 kV and 30 mA with CuKα radiation (1.54 Å).

Differential Scanning Calorimetry (DSC)

Differential scanning calorimetry (DSC) analysis was conducted on a TA Instruments Discovery Series calorimeter at 10 degrees C./min from 30 to 250 degrees Celsius in a crimped, aluminum pan under dry nitrogen at 50 ml/min.

Thermal Gravimetric Analysis (TGA)

Thermal gravimetric analysis (TGA) was performed on a TA Instruments Discovery Series analyzer at 10 degrees C./min from ambient temperature to 250 degrees C. in a platinum pan under dry nitrogen at 25 ml/min.

Optionally, Thermal gravimetric analysis (TGA) was performed on a TA Instruments thermogravimetric analyzer at 10° C./min from ambient temperature to 350° C. in a platinum pan under dry nitrogen at 25 ml/min.

Moisture Sorption

Moisture sorption data was collected using a dynamic vapor sorption (DVS) analyzer. A sample size of approximately 5-10 mg was used in a quartz pan. Hygroscopicity was evaluated from 0 to 95% RH in increments of 5 or 10% RH. Data for adsorption and desorption cycles were collected. Equilibrium criteria were set at 0.002% weight change in 5 minute with a maximum equilibration time of 120 minutes.

Solubility

Water: An excess of solid was added to water to produce a suspension and dispersed for at least 24 hours at room temperature. Suspensions were filtered. Filtrate was analyzed by UPLC-UV and compared against a standard curve to determine the solution concentration of the crystal form. Solids were analyzed by XRPD to determine the crystal form.

Toluene and Propanol: An excess of solid was added to produce a suspension and dispersed for at least 24 hours at 25, 35 and 45° C. Suspensions were filtered. Filtrate was analyzed by UPLC-UV and compared against a standard curve to determine the solution concentration of the crystal form. Solids were analyzed by XRPD to determine the crystal form.

Co-Slurry

An excess of solid Form I, Form III and Form IV was added to water or 80% acetonitrile in water and dispersed for at least 24 hours at 25 or 50° C. Suspensions were filtered. Solids were analyzed by XRPD to determine the crystal form.

Solid Stability

Drug substance was stored at 25 C/60% RH, 40 C/75% RH, 40 C/ambient or 60 C/ambient conditions. Chemical stability was determined at each timepoint by dissolving the drug substance in 50% acetonitrile water for UPLC analysis. Physical stability was determined by analyzing the solid by XRPD, DSC and TGA.

Free base Crystalline Form I: Form I was initially prepared by precipitation from 30% hyroxypropyl-β-cyclodextrin in deionized ("DI") water during a formulation screen. Form I undergoes a solid-solid transition to Form II at ~150-152° C. Form I is non-hygroscopic and the solubility of Form I in water is 0.013 mg/mL. Form I was physically and chemically stable for 14 weeks when stored at 25° C./60% RH, 40° C./75% RH, 40° C./ambient or 60° C./ambient conditions.

The free base crystalline Form I was characterized by an XRPD pattern comprising peaks in Table 1.

TABLE 1

| Pos. [°2 Th.] | FWHM [°2 Th.] | d-spacing [Å] | Height [cts] | Rel. Int. [%] |
|---|---|---|---|---|
| 8.23 | 0.19 | 10.74 | 2514.11 | 16.09 |
| 9.78 | 0.23 | 9.05 | 2824.50 | 18.07 |
| 11.99 | 0.19 | 7.38 | 148.65 | 0.95 |
| 12.45 | 0.23 | 7.11 | 1090.19 | 6.98 |
| 13.24 | 0.19 | 6.69 | 145.27 | 0.93 |
| 15.70 | 0.19 | 5.64 | 1696.06 | 10.85 |
| 16.46 | 0.23 | 5.38 | 9676.43 | 61.91 |
| 16.94 | 0.23 | 5.24 | 15629.64 | 100.00 |
| 17.73 | 0.19 | 5.00 | 589.01 | 3.77 |
| 18.49 | 0.16 | 4.80 | 592.88 | 3.79 |
| 19.29 | 0.13 | 4.60 | 582.51 | 3.73 |
| 19.56 | 0.16 | 4.54 | 975.13 | 6.24 |
| 20.11 | 0.23 | 4.41 | 686.92 | 4.39 |
| 22.12 | 0.26 | 4.02 | 301.03 | 1.93 |
| 22.99 | 0.19 | 3.87 | 864.08 | 5.53 |
| 23.97 | 0.19 | 3.71 | 964.78 | 6.17 |
| 24.40 | 0.16 | 3.65 | 1492.59 | 9.55 |
| 25.03 | 0.19 | 3.56 | 3022.92 | 19.34 |
| 25.49 | 0.19 | 3.49 | 1716.68 | 10.98 |
| 27.23 | 0.16 | 3.27 | 728.39 | 4.66 |
| 29.53 | 0.19 | 3.03 | 994.57 | 6.36 |
| 30.68 | 0.16 | 2.91 | 412.95 | 2.64 |
| 32.03 | 0.19 | 2.79 | 1808.66 | 11.57 |
| 32.71 | 0.19 | 2.74 | 481.52 | 3.08 |
| 33.21 | 0.19 | 2.70 | 538.94 | 3.45 |
| 34.07 | 0.39 | 2.63 | 541.55 | 3.46 |
| 35.25 | 0.23 | 2.55 | 504.85 | 3.23 |
| 35.72 | 0.23 | 2.51 | 529.35 | 3.39 |
| 37.78 | 0.52 | 2.38 | 251.86 | 1.61 |
| 38.99 | 0.19 | 2.31 | 370.56 | 2.37 |
| 39.68 | 0.26 | 2.27 | 328.25 | 2.10 |
| 41.43 | 0.26 | 2.18 | 455.68 | 2.92 |
| 41.91 | 0.23 | 2.16 | 668.58 | 4.28 |
| 42.83 | 0.19 | 2.11 | 620.66 | 3.97 |
| 44.18 | 0.32 | 2.05 | 366.30 | 2.34 |

Free Base Crystalline Form II:

Form II was prepared by heating Form I to 150-152° C. The melting point of Form II is ~180-182° C. (see the DSC of Form I). Form II converts back to Form I at temperatures below 132° C.

The free base crystalline Form II was characterized by an XRPD pattern comprising peaks in Table 2.

TABLE 2

| Pos. [°2 Th.] | FWHM [°2 Th.] | d-spacing [Å] | Height [cts] | Rel. Int. [%] |
|---|---|---|---|---|
| 6.80 | 0.40 | 13.00 | 70.17 | 0.37 |
| 7.67 | 0.12 | 11.53 | 1931.78 | 10.23 |
| 8.13 | 0.10 | 10.88 | 2273.22 | 12.04 |
| 8.31 | 0.08 | 10.64 | 1005.25 | 5.32 |
| 9.63 | 0.12 | 9.19 | 1849.18 | 9.79 |
| 10.08 | 0.13 | 8.77 | 178.57 | 0.95 |
| 11.54 | 0.08 | 7.67 | 377.37 | 2.00 |
| 12.21 | 0.12 | 7.25 | 1126.77 | 5.97 |
| 15.36 | 0.12 | 5.77 | 6568.02 | 34.78 |
| 16.03 | 0.10 | 5.53 | 1124.36 | 5.95 |
| 16.33 | 0.13 | 5.43 | 6328.35 | 33.52 |
| 16.70 | 0.13 | 5.31 | 18881.83 | 100.00 |
| 17.48 | 0.10 | 5.07 | 711.33 | 3.77 |
| 18.01 | 0.10 | 4.92 | 2943.21 | 15.59 |
| 18.27 | 0.15 | 4.86 | 7661.64 | 40.58 |
| 18.58 | 0.15 | 4.78 | 8159.62 | 43.21 |
| 18.82 | 0.05 | 4.72 | 2482.36 | 13.15 |
| 19.29 | 0.12 | 4.60 | 2006.87 | 10.63 |
| 19.51 | 0.12 | 4.55 | 2532.32 | 13.41 |
| 19.95 | 0.15 | 4.45 | 2239.77 | 11.86 |
| 20.29 | 0.12 | 4.38 | 2013.11 | 10.66 |
| 21.03 | 0.10 | 4.22 | 1553.42 | 8.23 |
| 21.38 | 0.17 | 4.16 | 4139.64 | 21.92 |
| 21.90 | 0.17 | 4.06 | 1859.08 | 9.85 |
| 22.37 | 0.13 | 3.97 | 2079.53 | 11.01 |
| 23.28 | 0.17 | 3.82 | 9093.31 | 48.16 |
| 23.59 | 0.15 | 3.77 | 4435.41 | 23.49 |

TABLE 2-continued

| Pos. [°2 Th.] | FWHM [°2 Th.] | d-spacing [Å] | Height [cts] | Rel. Int. [%] |
|---|---|---|---|---|
| 24.18 | 0.12 | 3.68 | 1838.59 | 9.74 |
| 24.61 | 0.12 | 3.62 | 5314.89 | 28.15 |
| 25.17 | 0.15 | 3.54 | 2887.39 | 15.29 |
| 25.55 | 0.13 | 3.49 | 1465.85 | 7.76 |
| 25.96 | 0.20 | 3.43 | 1654.51 | 8.76 |
| 26.83 | 0.15 | 3.32 | 3724.07 | 19.72 |
| 27.09 | 0.17 | 3.29 | 6075.01 | 32.17 |
| 27.40 | 0.08 | 3.26 | 2947.73 | 15.61 |
| 27.94 | 0.10 | 3.19 | 1834.95 | 9.72 |
| 29.30 | 0.17 | 3.05 | 2613.79 | 13.84 |
| 29.91 | 0.13 | 2.99 | 1866.59 | 9.89 |
| 30.60 | 0.17 | 2.92 | 1863.53 | 9.87 |
| 31.06 | 0.17 | 2.88 | 1707.07 | 9.04 |
| 31.63 | 0.08 | 2.83 | 2365.90 | 12.53 |
| 33.54 | 0.13 | 2.67 | 2626.06 | 13.91 |
| 34.56 | 0.13 | 2.60 | 2479.73 | 13.13 |
| 35.16 | 0.13 | 2.55 | 2087.81 | 11.06 |
| 35.80 | 0.17 | 2.51 | 2471.92 | 13.09 |
| 36.45 | 0.13 | 2.47 | 2252.74 | 11.93 |
| 36.94 | 0.13 | 2.43 | 2715.72 | 14.38 |
| 38.15 | 0.13 | 2.36 | 2892.52 | 15.32 |
| 39.26 | 0.20 | 2.29 | 3029.55 | 16.04 |
| 41.04 | 0.40 | 2.20 | 2628.00 | 13.92 |
| 41.80 | 0.20 | 2.16 | 2686.52 | 14.23 |
| 43.40 | 0.23 | 2.09 | 4923.31 | 26.07 |
| 44.26 | 0.37 | 2.04 | 6793.09 | 35.98 |

Free Base Crystalline Form III:

Form III was prepared by precipitation from acetonitrile (100 mg/mL) with water (1:2) at 25° C. during a solvent solubility screen. The monohydrate dehydrates under vacuum at ambient temperature, at temperatures greater than 25° C. or at low humidity.

The free base crystalline Form III was characterized by an XRPD pattern comprising peaks in Table 3.

TABLE 3

| Pos. [°2 Th.] | FWHM [°2 Th.] | d-spacing [Å] | Height [cts] | Rel. Int. [%] |
|---|---|---|---|---|
| 7.31 | 0.16 | 12.10 | 813.30 | 14.92 |
| 7.94 | 0.16 | 11.13 | 883.71 | 16.21 |
| 8.32 | 0.16 | 10.63 | 723.05 | 13.27 |
| 10.77 | 0.16 | 8.21 | 3540.32 | 64.93 |
| 13.96 | 0.16 | 6.35 | 5452.58 | 100.00 |
| 15.12 | 0.13 | 5.86 | 326.55 | 5.99 |
| 15.87 | 0.16 | 5.59 | 579.15 | 10.62 |
| 16.60 | 0.19 | 5.34 | 2334.84 | 42.82 |
| 17.50 | 0.26 | 5.07 | 200.86 | 3.68 |
| 18.56 | 0.16 | 4.78 | 3195.21 | 58.60 |
| 18.84 | 0.10 | 4.71 | 2228.08 | 40.86 |
| 19.41 | 0.19 | 4.57 | 2229.23 | 40.88 |
| 20.10 | 0.13 | 4.42 | 858.07 | 15.74 |
| 20.57 | 0.23 | 4.32 | 1604.20 | 29.42 |
| 21.19 | 0.13 | 4.19 | 496.70 | 9.11 |
| 21.61 | 0.16 | 4.11 | 3107.55 | 56.99 |
| 21.92 | 0.10 | 4.06 | 1744.88 | 32.00 |
| 22.28 | 0.16 | 3.99 | 1957.62 | 35.90 |
| 22.74 | 0.13 | 3.91 | 655.06 | 12.01 |
| 23.34 | 0.19 | 3.81 | 1466.83 | 26.90 |
| 23.88 | 0.13 | 3.73 | 1001.74 | 18.37 |
| 24.23 | 0.16 | 3.67 | 2702.38 | 49.56 |
| 24.70 | 0.26 | 3.60 | 3982.07 | 73.03 |
| 25.69 | 0.36 | 3.47 | 1123.49 | 20.60 |
| 27.08 | 0.19 | 3.29 | 338.52 | 6.21 |
| 27.65 | 0.26 | 3.23 | 592.55 | 10.87 |
| 28.07 | 0.13 | 3.18 | 615.00 | 11.28 |
| 28.38 | 0.13 | 3.15 | 823.46 | 15.10 |
| 28.87 | 0.13 | 3.09 | 1770.44 | 32.47 |
| 29.65 | 0.16 | 3.01 | 503.05 | 9.23 |

Free Base Crystalline Form IV:

Form IV was initially prepared by dehydration of Form III by pulling air through the Form III solids on the filter for 30 min at ambient conditions. The melting point of Form IV is ~167° C. Form IV is non-hygroscopic and the solubility in water is 0.010 mg/mL. Form IV was physically and chemically stable for 13 weeks when stored at 25° C./60% RH, 40° C./75% RH, 40° C./ambient or 60° C./ambient conditions.

The free base crystalline Form IV was characterized by an XRPD pattern comprising peaks in Table 4.

TABLE 4

| Pos. [°2 Th.] | FWHM [°2 Th.] | d-spacing [Å] | Height [cts] | Rel. Int. [%] |
|---|---|---|---|---|
| 8.06 | 0.13 | 10.97 | 1567.47 | 50.56 |
| 11.29 | 0.13 | 7.84 | 3040.49 | 98.08 |
| 11.70 | 0.13 | 7.57 | 234.88 | 7.58 |
| 12.08 | 0.13 | 7.33 | 531.63 | 17.15 |
| 13.27 | 0.13 | 6.67 | 312.17 | 10.07 |
| 14.97 | 0.13 | 5.92 | 1660.61 | 53.57 |
| 16.92 | 0.10 | 5.24 | 421.26 | 13.59 |
| 17.19 | 0.13 | 5.16 | 1073.59 | 34.63 |
| 17.63 | 0.23 | 5.03 | 2813.16 | 90.75 |
| 18.39 | 0.13 | 4.82 | 2738.42 | 88.34 |
| 18.95 | 0.10 | 4.68 | 1472.04 | 47.48 |
| 19.17 | 0.10 | 4.63 | 1373.13 | 44.29 |
| 20.17 | 0.10 | 4.40 | 892.21 | 28.78 |
| 20.50 | 0.13 | 4.33 | 3100.01 | 100.00 |
| 22.37 | 0.13 | 3.97 | 831.98 | 26.84 |
| 22.86 | 0.13 | 3.89 | 551.57 | 17.79 |
| 23.88 | 0.16 | 3.73 | 404.57 | 13.05 |
| 24.87 | 0.13 | 3.58 | 1377.52 | 44.44 |
| 25.69 | 0.16 | 3.47 | 669.55 | 21.60 |
| 26.03 | 0.16 | 3.42 | 1045.50 | 33.73 |
| 26.62 | 0.19 | 3.35 | 1281.30 | 41.33 |
| 27.13 | 0.13 | 3.29 | 438.28 | 14.14 |
| 27.99 | 0.13 | 3.19 | 945.91 | 30.51 |
| 28.26 | 0.13 | 3.16 | 715.51 | 23.08 |
| 28.73 | 0.13 | 3.11 | 585.91 | 18.90 |
| 29.25 | 0.16 | 3.05 | 1007.67 | 32.51 |
| 29.74 | 0.16 | 3.00 | 273.29 | 8.82 |

The XRPD peaks unique to each of the free base crystalline forms I-IV disclosed herein are shown in Table 5.

TABLE 5

| Free Form Form | Peaks Unique to Each Form (KA1 °) | | | | |
|---|---|---|---|---|---|
| Form I | 9.78 | 12.45 | 15.70 | 16.46 | 16.94 |
| Form II | 7.67 | 11.54 | 18.27 | 23.28 | |
| Form III | 7.31 | 10.77 | 13.96 | | |
| Form IV | 8.06 | 11.29 | 14.97 | | |

Hydrochloride Salt Form:

Hydrochloride Salt Form was initially prepared by precipitation from MTBE with 37 wt % hydrochloric acid in water. The salt disproportionates to Free Form upon exposure to water during moisture sorption experiments (hygroscopic) or slurry in water.

The hydrochloride salt form was characterized by an XRPD pattern comprising peaks in Table 6.

TABLE 6

| Pos. [°2 Th.] | FWHM [°2 Th.] | d-spacing [Å] | Height [cts] | Rel. Int. [%] |
|---|---|---|---|---|
| 8.45 | 0.23 | 10.46 | 2119.63 | 49.89 |
| 8.74 | 0.13 | 10.12 | 629.01 | 14.80 |
| 9.39 | 0.19 | 9.42 | 106.24 | 2.50 |
| 11.92 | 0.19 | 7.43 | 398.60 | 9.38 |
| 15.13 | 0.16 | 5.85 | 301.79 | 7.10 |
| 16.08 | 0.19 | 5.51 | 492.73 | 11.60 |
| 16.93 | 0.23 | 5.24 | 3630.10 | 85.44 |
| 17.33 | 0.16 | 5.12 | 1772.88 | 41.73 |
| 17.76 | 0.19 | 4.99 | 1464.20 | 34.46 |
| 18.75 | 0.19 | 4.73 | 922.62 | 21.71 |

TABLE 6-continued

| Pos. [°2 Th.] | FWHM [°2 Th.] | d-spacing [Å] | Height [cts] | Rel. Int. [%] |
|---|---|---|---|---|
| 19.51 | 0.19 | 4.55 | 1176.47 | 27.69 |
| 19.81 | 0.10 | 4.48 | 616.64 | 14.51 |
| 20.53 | 0.23 | 4.33 | 1279.42 | 30.11 |
| 21.36 | 0.23 | 4.16 | 1297.74 | 30.54 |
| 22.28 | 0.19 | 3.99 | 271.79 | 6.40 |
| 22.95 | 0.23 | 3.87 | 1840.89 | 43.33 |
| 23.74 | 0.23 | 3.75 | 2478.58 | 58.33 |
| 24.59 | 0.39 | 3.62 | 2988.72 | 70.34 |
| 25.28 | 0.26 | 3.52 | 1009.44 | 23.76 |
| 25.89 | 0.19 | 3.44 | 1000.65 | 23.55 |
| 26.57 | 0.23 | 3.36 | 4248.95 | 100.00 |
| 26.94 | 0.13 | 3.31 | 1082.71 | 25.48 |
| 27.44 | 0.19 | 3.25 | 1054.98 | 24.83 |
| 28.58 | 0.19 | 3.12 | 482.67 | 11.36 |
| 29.41 | 0.19 | 3.04 | 1194.59 | 28.11 |

Dichloromethane Solvate:

Dichloromethane Solvate Form I was prepared by evaporation from dichloromethane (100 mg/mL) at ambient temperature. The solvate desolvates to Free Form I at ~75° C.

The dichloromethane solvate was characterized by an XRPD pattern comprising peaks in Table 7.

TABLE 7

| Pos. [°2 Th.] | FWHM [°2 Th.] | d-spacing [Å] | Height [cts] | Rel. Int. [%] |
|---|---|---|---|---|
| 6.76 | 0.16 | 13.07 | 720.61 | 11.92 |
| 8.25 | 0.16 | 10.71 | 861.09 | 14.24 |
| 9.43 | 0.19 | 9.38 | 164.11 | 2.71 |
| 11.46 | 0.19 | 7.72 | 2116.94 | 35.01 |
| 13.47 | 0.19 | 6.57 | 212.57 | 3.52 |
| 14.04 | 0.10 | 6.31 | 377.20 | 6.24 |
| 16.26 | 0.16 | 5.45 | 782.81 | 12.95 |
| 16.91 | 0.19 | 5.24 | 6047.20 | 100.00 |
| 18.82 | 0.19 | 4.72 | 937.49 | 15.50 |
| 19.50 | 0.13 | 4.55 | 936.06 | 15.48 |
| 19.90 | 0.16 | 4.46 | 1609.40 | 26.61 |
| 20.52 | 0.16 | 4.33 | 1974.39 | 32.65 |
| 20.79 | 0.10 | 4.27 | 1332.81 | 22.04 |
| 21.58 | 0.29 | 4.12 | 1516.98 | 25.09 |
| 22.53 | 0.19 | 3.95 | 527.26 | 8.72 |
| 23.10 | 0.16 | 3.85 | 2306.11 | 38.14 |
| 23.92 | 0.13 | 3.72 | 1360.97 | 22.51 |
| 24.58 | 0.16 | 3.62 | 1948.89 | 32.23 |
| 25.18 | 0.13 | 3.54 | 844.76 | 13.97 |
| 26.20 | 0.16 | 3.40 | 1047.32 | 17.32 |
| 26.95 | 0.13 | 3.31 | 844.84 | 13.97 |
| 27.18 | 0.13 | 3.28 | 837.05 | 13.84 |
| 27.62 | 0.13 | 3.23 | 721.27 | 11.93 |
| 28.26 | 0.13 | 3.16 | 766.28 | 12.67 |
| 29.35 | 0.19 | 3.04 | 1496.50 | 24.75 |

Nitromethane Solvate:

Nitromethane Solvate Form I was prepared by evaporation from nitromethane (44 mg/mL) under ambient conditions. The solvate desolvates to Free Form I at ~81-97° C.

The dichloromethane solvate was characterized by an XRPD pattern comprising peaks in Table 8.

TABLE 8

| Pos. [°2 Th.] | FWHM [°2 Th.] | d-spacing [Å] | Height [cts] | Rel. Int. [%] |
|---|---|---|---|---|
| 6.61 | 0.16 | 13.38 | 949.30 | 19.09 |
| 7.37 | 0.19 | 12.00 | 219.82 | 4.42 |
| 8.14 | 0.23 | 10.87 | 213.73 | 4.30 |
| 8.94 | 0.19 | 9.90 | 2315.01 | 46.56 |
| 10.18 | 0.19 | 8.69 | 1099.24 | 22.11 |
| 11.33 | 0.23 | 7.81 | 261.74 | 5.26 |
| 11.98 | 0.19 | 7.39 | 143.75 | 2.89 |
| 12.45 | 0.13 | 7.11 | 236.85 | 4.76 |

TABLE 8-continued

| Pos. [°2 Th.] | FWHM [°2 Th.] | d-spacing [Å] | Height [cts] | Rel. Int. [%] |
|---|---|---|---|---|
| 13.31 | 0.19 | 6.65 | 144.03 | 2.90 |
| 13.87 | 0.16 | 6.38 | 428.90 | 8.63 |
| 14.63 | 0.19 | 6.06 | 173.65 | 3.49 |
| 15.86 | 0.13 | 5.59 | 2109.15 | 42.42 |
| 17.12 | 0.19 | 5.18 | 4971.90 | 100.00 |
| 18.16 | 0.26 | 4.88 | 1301.24 | 26.17 |
| 19.01 | 0.19 | 4.67 | 846.61 | 17.03 |
| 19.51 | 0.16 | 4.55 | 2162.56 | 43.50 |
| 19.83 | 0.19 | 4.48 | 1882.29 | 37.86 |
| 20.54 | 0.23 | 4.32 | 1638.55 | 32.96 |
| 21.93 | 0.19 | 4.05 | 1343.45 | 27.02 |
| 22.68 | 0.10 | 3.92 | 764.69 | 15.38 |
| 23.06 | 0.23 | 3.86 | 1834.23 | 36.89 |
| 23.92 | 0.19 | 3.72 | 2273.36 | 45.72 |
| 24.41 | 0.19 | 3.65 | 1858.60 | 37.38 |
| 25.37 | 0.23 | 3.51 | 1052.59 | 21.17 |
| 26.61 | 0.29 | 3.35 | 883.52 | 17.77 |
| 28.32 | 0.29 | 3.15 | 728.80 | 14.66 |

Hexafluoro-2-Propanol Solvate:

Hexafluoro-2-propanol Solvate Form I was prepared by the solvent-drop crystallization method (sonication of ~5 mg with 50 μL of hexafluoro-2-propanol for 60 min). The solvate desolvates to Free Form I at ~83-100° C.

The hexafluoro-2-propanol solvate was characterized by an XRPD pattern comprising peaks in Table 9.

TABLE 9

| Pos. [°2 Th.] | FWHM [°2 Th.] | d-spacing [Å] | Height [cts] | Rel. Int. [%] |
|---|---|---|---|---|
| 9.49 | 0.20 | 9.32 | 105.76 | 25.75 |
| 11.20 | 0.20 | 7.90 | 110.51 | 26.90 |
| 16.17 | 0.20 | 5.48 | 240.31 | 58.50 |
| 16.70 | 0.20 | 5.31 | 410.77 | 100.00 |
| 18.20 | 0.20 | 4.88 | 172.73 | 42.05 |
| 20.18 | 0.34 | 4.40 | 77.32 | 18.82 |
| 21.39 | 0.30 | 4.15 | 50.73 | 12.35 |
| 23.03 | 0.20 | 3.86 | 127.08 | 30.94 |
| 23.74 | 0.25 | 3.75 | 113.20 | 27.56 |
| 25.46 | 0.79 | 3.50 | 49.71 | 12.10 |
| 27.00 | 0.30 | 3.30 | 50.17 | 12.21 |
| 29.24 | 0.15 | 3.05 | 56.78 | 13.82 |
| 33.76 | 0.30 | 2.65 | 37.09 | 9.03 |

Compound a and Propyl Gallate Cocrystal:

Propyl gallate cocrystal was prepared from liquid assisted grinding of Compound A (30 mg) with 1 mol eq of propyl gallate and 5 μL of solvent (EtOH) in a Fritsch planetary mill, with 2 small ball bearings, at 500 rpm for 2 h. The sample was then treated with toluene (500 μL) and matured by cycling the temperature through six, 4 h cycles from RT to 50° C., then held at 5° C. for 48 h. Isolated solids were identified as a propyl gallate cocrystal.

This cocrystal was also prepared from liquid assisted grinding Compound A (30 mg) with 1 mol eq of propyl gallate and 5 μL of solvent (EtOAc) in a Fritsch planetary mill, with 2 small ball bearings, at 500 rpm for 2 h. Isolated solids were identified as a propyl gallate cocrystal.

1H NMR confirms the chemical structure and the presence of ~2.0 mol equivalents propyl gallate and ~0.07 mol equivalents residual EtOAc.

Propyl gallate cocrystal NMR: $^1$H NMR (400 MHz, DMSO-$d_6$) δ ppm 0.33-0.41 (m, 2H) 0.42-0.50 (m, 1H) 0.54-0.62 (m, 1H) 0.70-0.82 (m, 1H) 0.91-0.99 (m, 3H) 1.07-1.13 (m, 1H) 1.15-1.27 (m, 1H) 1.61-1.80 (m, 4H) 1.97-2.00 (m, 1H) 2.53-2.64 (m, 1H) 3.33-3.43 (m, 4H) 3.71-3.77 (m, 3H) 3.99-4.06 (m, 1H) 4.08-4.15 (m, 2H) 4.48-4.57 (m, 1H) 4.67-4.73 (m, 1H) 4.91-4.99 (m, 1H)

6.92-6.97 (m, 2H) 7.43-7.50 (m, 1H) 7.55-7.63 (m, 1H) 7.69-7.74 (m, 1H) 7.74-7.81 (m, 1H) 8.29-8.33 (m, 1H) 8.47-8.51 (m, 1H) 8.71-8.80 (m, 1H) 8.85-8.90 (m, 1H) 9.11-9.16 (m, 1H) 9.18-9.24 (m, 1H).

The propyl gallate cocrystal was characterized by an XRPD pattern comprising peaks in Table 10.

TABLE 10

| Pos. [°2 Th.] | FWHM [°2 Th.] | d-spacing [Å] | Height [cts] | Rel. Int. [%] |
|---|---|---|---|---|
| 3.05 | 0.10 | 28.97 | 138.41 | 13.30 |
| 6.12 | 0.10 | 14.44 | 88.73 | 8.52 |
| 8.66 | 0.08 | 10.21 | 395.91 | 38.03 |
| 9.21 | 0.08 | 9.60 | 285.10 | 27.39 |
| 10.65 | 0.08 | 8.31 | 52.51 | 5.04 |
| 11.24 | 0.08 | 7.87 | 125.53 | 12.06 |
| 13.23 | 0.20 | 6.69 | 26.54 | 2.55 |
| 15.00 | 0.06 | 5.91 | 1041.03 | 100.00 |
| 17.16 | 0.15 | 5.17 | 50.86 | 4.89 |
| 17.72 | 0.14 | 5.01 | 577.05 | 55.43 |
| 18.32 | 0.05 | 4.84 | 204.49 | 19.64 |
| 18.82 | 0.09 | 4.72 | 405.73 | 38.97 |
| 19.36 | 0.09 | 4.58 | 249.50 | 23.97 |
| 20.32 | 0.14 | 4.37 | 395.72 | 38.01 |
| 20.49 | 0.12 | 4.33 | 339.45 | 32.61 |
| 21.73 | 0.12 | 4.09 | 164.40 | 15.79 |
| 22.57 | 0.08 | 3.94 | 324.89 | 31.21 |
| 22.98 | 0.15 | 3.87 | 107.36 | 10.31 |
| 23.39 | 0.18 | 3.80 | 160.61 | 15.43 |
| 23.86 | 0.15 | 3.73 | 90.48 | 8.69 |
| 25.01 | 0.13 | 3.56 | 126.37 | 12.14 |
| 25.51 | 0.18 | 3.49 | 187.06 | 17.97 |
| 26.30 | 0.10 | 3.39 | 139.71 | 13.42 |
| 26.52 | 0.10 | 3.36 | 167.23 | 16.06 |
| 28.31 | 0.13 | 3.15 | 150.52 | 14.46 |
| 28.66 | 0.18 | 3.11 | 73.65 | 7.07 |
| 29.68 | 0.15 | 3.01 | 28.04 | 2.69 |
| 30.54 | 0.41 | 2.93 | 19.74 | 1.90 |

Compound a and Glycerol Cocrystal:

Glyceral cocrystal was prepared from liquid assisted grinding of Compound A (30 mg) with 1 mol eq of propyl gallate and 5 µL of solvent (EtOAc) in a Fritsch planetary mill, with 2 small ball bearings, at 500 rpm for 2 h. The sample was then treated with acetone (500 µL) and matured by cycling the temperature through six, 4 h cycles from RT to 50° C., then held at 5° C. for 48 h. Isolated solids were identified as a glycerol cocrystal.

1H NMR confirms the chemical structure and the presence of ~2.6 mol equivilant glycerol and ~0.11 mol equivilant residual acetone. Stable to 40° C./75% RH storage 7 d by XRPD.

Glycerol cocrystal NMR: $^1$H NMR (400 MHz, DMSO-$d_6$) δ ppm 0.37 (br s, 2H) 0.46 (br t, J=8.72 Hz, 1H) 0.57 (br s, 1H) 0.77 (br d, J=8.84 Hz, 1H) 1.10 (br d, J=2.53 Hz, 1H) 1.73 (br s, 1H) 1.74-1.74 (m, 1H) 1.77 (d, J=3.54 Hz, 1H) 2.07 (s, 1H) 3.23-3.31 (m, 4H) 3.24-3.31 (m, 1H) 3.27-3.31 (m, 1H) 3.31-3.46 (m, 23H) 3.35-3.46 (m, 1H) 3.49-3.52 (m, 1H) 3.71-3.77 (m, 1H) 4.07 (t, J=8.34 Hz, 1H) 4.40 (t, J=5.68 Hz, 5H) 4.48 (d, J=4.80 Hz, 3H) 4.52 (t, J=7.96 Hz, 1H) 4.70 (dd, J=11.24, 2.65 Hz, 1H) 4.95 (dd, J=11.49, 3.66 Hz, 1H) 7.46 (dd, J=10.74, 5.68 Hz, 1H) 7.59 (dd, J=10.99, 5.43 Hz, 1H) 7.72 (dd, J=9.47, 5.94 Hz, 1H) 7.77 (dd, J=9.35, 5.81 Hz, 1H) 8.31 (t, J=2.15 Hz, 1H) 8.49 (t, J=2.15 Hz, 1H) 8.53 (d, J=7.83 Hz, 1H) 8.75 (d, J=7.58 Hz, 1H) 8.87 (d, J=2.02 Hz, 1H) 9.13 (d, J=2.02 Hz, 1H) 9.21 (d, J=2.27 Hz, 1H).

The Compound A and glycerol cocrystal was characterized by an XRPD pattern comprising peaks in Table 11.

TABLE 11

| Pos. [°2 Th.] | FWHM [°2 Th.] | d-spacing [Å] | Height [cts] | Rel. Int. [%] |
|---|---|---|---|---|
| 2.87 | 0.61 | 30.77 | 14.43 | 0.63 |
| 7.90 | 0.06 | 11.19 | 173.39 | 7.54 |
| 8.17 | 0.06 | 10.83 | 126.26 | 5.49 |
| 8.38 | 0.08 | 10.55 | 60.82 | 2.64 |
| 9.70 | 0.08 | 9.12 | 186.10 | 8.09 |
| 11.85 | 0.08 | 7.47 | 50.19 | 2.18 |
| 12.38 | 0.08 | 7.15 | 104.08 | 4.52 |
| 13.13 | 0.20 | 6.74 | 24.53 | 1.07 |
| 15.60 | 0.08 | 5.68 | 202.49 | 8.80 |
| 16.39 | 0.06 | 5.41 | 358.00 | 15.56 |
| 16.84 | 0.10 | 5.26 | 1007.09 | 43.77 |
| 18.25 | 0.08 | 4.86 | 164.46 | 7.15 |
| 18.48 | 0.10 | 4.80 | 1779.04 | 77.32 |
| 18.95 | 0.10 | 4.68 | 411.95 | 17.91 |
| 19.40 | 0.06 | 4.58 | 936.22 | 40.69 |
| 20.03 | 0.10 | 4.43 | 166.63 | 7.24 |
| 21.49 | 0.05 | 4.14 | 2300.74 | 100.00 |
| 22.51 | 0.13 | 3.95 | 196.74 | 8.55 |
| 22.87 | 0.13 | 3.89 | 142.01 | 6.17 |
| 23.87 | 0.13 | 3.73 | 170.06 | 7.39 |
| 24.53 | 0.13 | 3.63 | 224.80 | 9.77 |
| 24.92 | 0.08 | 3.57 | 193.80 | 8.42 |
| 25.44 | 0.26 | 3.50 | 66.39 | 2.89 |
| 27.10 | 0.13 | 3.29 | 170.48 | 7.41 |
| 27.61 | 0.18 | 3.23 | 79.43 | 3.45 |
| 28.88 | 0.20 | 3.09 | 42.07 | 1.83 |
| 30.62 | 0.20 | 2.92 | 29.68 | 1.29 |

Compound A and Propylene Glycol Cocrystal:

Propylene glycol cocrystal was prepared from liquid assisted grinding of Compound A (30 mg) with 1 mol eq of propylene glycol and 5 µL of solvent (EtOAc) in a Fritsch planetary mill, with 2 small ball bearings, at 500 rpm for 2 h. The sample was then treated with acetone (500 µL) and matured by cycling the temperature through six, 4 h cycles from RT to 50° C., then held at 5° C. for 48 h. Isolated solids were identified as a propylene glycol cocrystal.

1H NMR confirms the chemical structure and the presence of ~1.0 mol equivilant propylene glycol. Stable to 40° C./75% RH storage 7 d by XRPD.

Propylene glycol NMR: $^1$H NMR (400 MHz, DMSO-$d_6$) δ ppm 0.37 (br s, 2H) 0.42-0.51 (m, 1H) 0.53-0.62 (m, 1H) 0.77 (br d, J=8.84 Hz, 2H) 0.99 (d, J=6.32 Hz, 3H) 1.10 (br d, J=2.53 Hz, 1H) 1.20 (br d, J=8.08 Hz, 1H) 1.67-1.79 (m, 2H) 3.10-3.18 (m, 1H) 3.11-3.29 (m, 1H) 3.25 (dt, J=10.74, 5.49 Hz, 1H) 3.35-3.42 (m, 4H) 3.50-3.61 (m, 1H) 3.70-3.78 (m, 1H) 4.07 (br t, J=8.21 Hz, 1H) 4.41 (d, J=4.29 Hz, 1H) 4.47 (t, J=5.68 Hz, 1H) 4.52 (t, J=7.83 Hz, 1H) 4.70 (br dd, J=11.37, 2.53 Hz, 1H) 4.95 (dd, J=11.37, 3.54 Hz, 1 H) 7.46 (br dd, J=10.99, 5.18 Hz, 1H) 7.59 (dd, J=10.99, 5.43 Hz, 1H) 7.68-7.73 (m, 1H) 7.77 (dd, J=9.47, 5.94 Hz, 1H) 8.28-8.33 (m, 1H) 8.45-8.51 (m, 1H) 8.51-8.56 (m, 1H) 8.75 (br d, J=7.33 Hz, 1H) 8.87 (d, J=1.77 Hz, 1H) 9.13 (d, J=1.77 Hz, 1H) 9.21 (d, J=2.02 Hz, 1H).

The Compound A and propylene glycol cocrystal was characterized by an XRPD pattern comprising peaks in Table 12.

TABLE 12

| Pos. [°2 Th.] | FWHM [°2 Th.] | d-spacing [Å] | Height [cts] | Rel. Int. [%] |
|---|---|---|---|---|
| 7.87 | 0.06 | 11.23 | 160.28 | 5.25 |
| 8.16 | 0.08 | 10.84 | 74.47 | 2.44 |
| 9.69 | 0.06 | 9.13 | 124.64 | 4.08 |
| 11.84 | 0.08 | 7.47 | 41.96 | 1.37 |
| 12.36 | 0.05 | 7.16 | 77.17 | 2.53 |
| 13.08 | 0.15 | 6.77 | 21.61 | 0.71 |
| 15.61 | 0.08 | 5.68 | 176.30 | 5.77 |

TABLE 12-continued

| Pos. [°2 Th.] | FWHM [°2 Th.] | d-spacing [Å] | Height [cts] | Rel. Int. [%] |
|---|---|---|---|---|
| 16.36 | 0.09 | 5.42 | 201.92 | 6.61 |
| 16.82 | 0.08 | 5.27 | 540.59 | 17.70 |
| 18.26 | 0.06 | 4.86 | 321.63 | 10.53 |
| 18.39 | 0.06 | 4.82 | 269.95 | 8.84 |
| 18.93 | 0.09 | 4.69 | 1668.23 | 54.63 |
| 19.37 | 0.10 | 4.58 | 3053.51 | 100.00 |
| 20.02 | 0.08 | 4.44 | 106.48 | 3.49 |
| 20.39 | 0.04 | 4.36 | 246.13 | 8.06 |
| 21.12 | 0.09 | 4.21 | 184.55 | 6.04 |
| 21.52 | 0.08 | 4.13 | 388.81 | 12.73 |
| 21.83 | 0.08 | 4.07 | 113.27 | 3.71 |
| 22.47 | 0.13 | 3.96 | 268.23 | 8.78 |
| 22.85 | 0.09 | 3.89 | 135.31 | 4.43 |
| 23.39 | 0.15 | 3.80 | 44.11 | 1.44 |
| 23.84 | 0.13 | 3.73 | 115.84 | 3.79 |
| 24.46 | 0.09 | 3.64 | 291.01 | 9.53 |
| 25.05 | 0.08 | 3.55 | 97.85 | 3.20 |
| 25.36 | 0.10 | 3.51 | 37.13 | 1.22 |
| 26.66 | 0.13 | 3.34 | 45.55 | 1.49 |
| 27.07 | 0.13 | 3.29 | 107.42 | 3.52 |
| 27.60 | 0.13 | 3.23 | 66.70 | 2.18 |
| 28.85 | 0.15 | 3.09 | 44.28 | 1.45 |
| 30.56 | 0.10 | 2.93 | 46.14 | 1.51 |

Compound A and Maltol Cocrystal:

Maltol cocrystal was prepared from liquid assisted grinding of Compound A (30 mg) with 1 mol eq of maltol and 5 μL of solvent (EtOAc) in a Fritsch planetary mill, with 2 small ball bearings, at 500 rpm for 2 h. The sample was then treated with acetone (500 μL) and matured by cycling the temperature through six, 4 h cycles from RT to 50° C., then held at 5° C. for 48 h. Isolated solids were identified as a maltol cocrystal.

1H NMR confirms the chemical structure and the presence of ~0.8 mol equivalents maltol and ~0.14 mol equivalents residual acetone. Stable to 40° C./75% RH storage 7 d by XRPD.

Maltol Cocrystal NMR: $^1$H NMR (400 MHz, DMSO-$d_6$) δ ppm 0.37 (br s, 2H) 0.42-0.50 (m, 1H) 0.53-0.62 (m, 1H) 0.71-0.81 (m, 2H) 1.07-1.13 (m, 1H) 1.20 (br d, J=8.08 Hz, 1H) 1.67-1.79 (m, 2H) 2.07 (s, 1H) 2.24 (s, 2H) 3.36-3.44 (m, 5H) 3.71-3.78 (m, 1H) 4.07 (t, J=8.34 Hz, 1H) 4.52 (t, J=7.96 Hz, 1H) 4.70 (dd, J=11.37, 2.78 Hz, 1H) 4.95 (dd, J=11.37, 3.54 Hz, 1H) 6.33 (d, J=5.56 Hz, 1H) 7.46 (dd, J=11.12, 5.81 Hz, 1H) 7.59 (dd, J=10.86, 5.56 Hz, 1H) 7.72 (dd, J=9.47, 5.94 Hz, 1H) 7.77 (dd, J=9.35, 5.81 Hz, 1H) 8.03 (d, J=5.56 Hz, 1H) 8.31 (t, J=2.15 Hz, 1H) 8.49 (t, J=2.15 Hz, 1H) 8.53 (d, J=7.58 Hz, 1H) 8.75 (d, J=7.33 Hz, 1H) 8.84 (s, 1H) 8.87 (d, J=2.02 Hz, 1H) 9.13 (d, J=1.77 Hz, 1H) 9.21 (d, J=2.27 Hz, 1H).

1H NMR confirms the chemical structure and the presence of ~1.0 mol equivilant propylene glycol. Stable to 40° C./75% RH storage 7 d by XRPD.

The Compound A and maltol cocrystal was characterized by an XRPD pattern comprising peaks in Table 13.

TABLE 13

| Pos. [°2 Th.] | FWHM [°2 Th.] | d-spacing [Å] | Height [cts] | Rel. Int. [%] |
|---|---|---|---|---|
| 4.44 | 0.31 | 19.90 | 24.21 | 11.73 |
| 6.58 | 0.18 | 13.43 | 42.00 | 20.36 |
| 7.98 | 0.41 | 11.08 | 26.78 | 12.98 |
| 8.86 | 0.15 | 9.99 | 75.50 | 36.60 |
| 13.13 | 0.15 | 6.74 | 34.27 | 16.61 |
| 13.68 | 0.10 | 6.47 | 48.09 | 23.31 |
| 14.60 | 0.15 | 6.07 | 46.55 | 22.57 |
| 15.25 | 0.31 | 5.81 | 48.15 | 23.34 |
| 16.85 | 0.13 | 5.26 | 154.05 | 74.67 |

TABLE 13-continued

| Pos. [°2 Th.] | FWHM [°2 Th.] | d-spacing [Å] | Height [cts] | Rel. Int. [%] |
|---|---|---|---|---|
| 18.18 | 0.26 | 4.88 | 115.14 | 55.81 |
| 19.53 | 0.08 | 4.55 | 206.30 | 100.00 |
| 21.52 | 0.31 | 4.13 | 50.69 | 24.57 |
| 23.54 | 0.51 | 3.78 | 89.47 | 43.37 |
| 25.26 | 0.31 | 3.53 | 46.38 | 22.48 |
| 26.63 | 0.31 | 3.35 | 56.21 | 27.25 |

Compound a and Urea Cocrystal:

Urea cocrystal was prepared from liquid assisted grinding Compound A (30 mg) with 1 mol eq of urea and 5 μL of solvent (EtOH or EtOAc) in a Fritsch planetary mill, with 2 small ball bearings, at 500 rpm for 2 h. Isolated solids were identified as a urea cocrystal.

1H NMR confirms the chemical structure and the presence of ~1.0 mol equivilant urea. Stable to 25° C./97% RH and 40° C./75% RH storage 7 d by XRPD.

Urea Cocrystal NMR: $^1$H NMR (400 MHz, DMSO-$d_6$) δ ppm −0.21 (br dd, J=8.84, 4.55 Hz, 1H) −0.07-0.03 (m, 1H) 0.37 (br s, 1H) 0.46 (br t, J=8.59 Hz, 1H) 0.53-0.61 (m, 1H) 0.77 (td, J=8.97, 4.80 Hz, 1H) 1.10 (td, J=5.05, 2.78 Hz, 1H) 1.15-1.26 (m, 1H) 1.58-1.64 (m, 1H) 1.67-1.79 (m, 2H) 3.35-3.42 (m, 4H) 3.68-3.79 (m, 1H) 4.02-4.11 (m, 1H) 4.52 (t, J=7.96 Hz, 1H) 4.70 (br dd, J=11.24, 2.65 Hz, 1H) 4.95 (dd, J=11.37, 3.54 Hz, 1H) 5.40 (br s, 3H) 5.35-5.47 (m, 1H) 6.55 (s, 1H) 7.46 (dd, J=11.24, 5.68 Hz, 1H) 7.59 (dd, J=10.99, 5.43 Hz, 1H) 7.69-7.82 (m, 1H) 8.31 (t, J=2.15 Hz, 1H) 8.49 (t, J=2.02 Hz, 1H) 8.53 (d, J=7.58 Hz, 1H) 8.75 (d, J=7.33 Hz, 1H) 8.87 (d, J=2.02 Hz, 1H) 9.13 (d, J=2.02 Hz, 1H) 9.21 (d, J=2.27 Hz, 1H).

The Compound A and urea cocrystal was characterized by an XRPD pattern comprising peaks in Table 14.

TABLE 14

| Pos. [°2 Th.] | FWHM [°2 Th.] | d-spacing [Å] | Height [cts] | Rel. Int. [%] |
|---|---|---|---|---|
| 3.99 | 0.05 | 22.15 | 946.23 | 47.52 |
| 8.01 | 0.06 | 11.04 | 673.52 | 33.82 |
| 8.39 | 0.08 | 10.54 | 538.35 | 27.04 |
| 11.24 | 0.08 | 7.87 | 1991.25 | 100.00 |
| 11.63 | 0.06 | 7.61 | 128.89 | 6.47 |
| 12.03 | 0.06 | 7.36 | 182.97 | 9.19 |
| 12.22 | 0.08 | 7.24 | 65.14 | 3.27 |
| 13.24 | 0.08 | 6.69 | 175.95 | 8.84 |
| 14.96 | 0.10 | 5.92 | 701.61 | 35.23 |
| 15.21 | 0.06 | 5.83 | 343.50 | 17.25 |
| 15.98 | 0.13 | 5.55 | 162.31 | 8.15 |
| 16.93 | 0.05 | 5.24 | 240.73 | 12.09 |
| 17.16 | 0.14 | 5.17 | 371.57 | 18.66 |
| 17.47 | 0.06 | 5.08 | 764.91 | 38.41 |
| 17.62 | 0.09 | 5.03 | 1101.50 | 55.32 |
| 18.37 | 0.12 | 4.83 | 1422.78 | 71.45 |
| 18.94 | 0.10 | 4.69 | 461.78 | 23.19 |
| 19.13 | 0.09 | 4.64 | 575.50 | 28.90 |
| 19.75 | 0.08 | 4.50 | 137.57 | 6.91 |
| 20.13 | 0.09 | 4.41 | 198.36 | 9.96 |
| 20.51 | 0.13 | 4.33 | 741.55 | 37.24 |
| 20.86 | 0.08 | 4.26 | 168.67 | 8.47 |
| 21.50 | 0.10 | 4.13 | 136.81 | 6.87 |
| 22.37 | 0.13 | 3.97 | 238.21 | 11.96 |
| 22.62 | 0.10 | 3.93 | 188.58 | 9.47 |
| 22.83 | 0.08 | 3.90 | 190.97 | 9.59 |
| 23.41 | 0.10 | 3.80 | 126.41 | 6.35 |
| 23.80 | 0.13 | 3.74 | 108.28 | 5.44 |
| 24.24 | 0.13 | 3.67 | 135.64 | 6.81 |
| 24.65 | 0.09 | 3.61 | 702.18 | 35.26 |
| 24.86 | 0.10 | 3.58 | 609.98 | 30.63 |
| 25.36 | 0.13 | 3.51 | 155.46 | 7.81 |
| 25.70 | 0.06 | 3.47 | 439.89 | 22.09 |
| 25.97 | 0.14 | 3.43 | 425.91 | 21.39 |

TABLE 14-continued

| Pos. [°2 Th.] | FWHM [°2 Th.] | d-spacing [Å] | Height [cts] | Rel. Int. [%] |
|---|---|---|---|---|
| 26.35 | 0.08 | 3.38 | 214.61 | 10.78 |
| 26.62 | 0.18 | 3.35 | 490.09 | 24.61 |
| 27.12 | 0.13 | 3.29 | 90.14 | 4.53 |
| 28.01 | 0.13 | 3.19 | 352.78 | 17.72 |
| 28.26 | 0.13 | 3.16 | 236.03 | 11.85 |
| 28.77 | 0.20 | 3.10 | 196.12 | 9.85 |
| 29.25 | 0.15 | 3.05 | 318.69 | 16.00 |
| 29.75 | 0.15 | 3.00 | 51.41 | 2.58 |

Amorphous Form:

Compound A (300 mg) was dissolved in tBuOH:H2O (1:1, 30 vol) at 50° C. The clear solution was filtered to remove any undissolved particulates which could act as nucleation points. The filtered solution was immediately frozen in a dry-ice/acetone bath and placed on the freeze drier to lyophilize. The resulting solid was analyzed by XRPD.

1H NMR confirms structure with ~0.39 mol equivalents residual tBuOH. TGA indicates a 2.9% w/w between 50° C.-96° C. which corresponds to ~0.22 mol eq of residual tBuOH. Crystallizes upon static storage at 80° C./0% RH or 40° C./75% RH within 1 week.

Amorphous crystalline form NMR: $^1$H NMR (400 MHz, DMSO-$d_6$) δ ppm −0.31-0.06 (m, 1H) −0.28--0.14 (m, 1H) −0.12-0.04 (m, 1H) −0.10-0.04 (m, 1H) −0.09-0.04 (m, 1H) 0.37 (br s, 3H) 0.52-0.67 (m, 1H) 0.68-0.84 (m, 2H) 1.07-1.23 (m, 6H) 1.57-1.79 (m, 3H) 2.30-2.36 (m, 1H) 2.53-2.79 (m, 2H) 3.68-3.79 (m, 1H) 4.20 (s, 1H) 4.15-4.24 (m, 1H) 4.52 (t, J=7.96 Hz, 1H) 4.64-4.78 (m, 1H) 4.95 (dd, J=11.37, 3.54 Hz, 1H) 7.41-7.52 (m, 1H) 7.59 (dd, J=11.12, 5.56 Hz, 1H) 7.77 (dd, J=9.47, 5.94 Hz, 2H) 8.27-8.34 (m, 1H) 8.49 (t, J=2.15 Hz, 2H) 8.76 (d, J=7.33 Hz, 1H) 8.87 (d, J=1.77 Hz, 1H) 9.10-9.17 (m, 1H) 9.21 (d, J=2.27 Hz, 1H).

What is claimed:

1. A free base crystalline form of Compound A, selected from the following forms:
   (i) a free base anhydrous crystalline Form I of Compound A, characterized by an X-ray powder diffraction (XRPD) pattern comprising peaks at 9.78, 12.45, 15.70, 16.46, and 16.94±0.2° 2θ using Cu Kα radiation;
   (ii) a free base anhydrous crystalline Form II of Compound A, characterized by an X-ray powder diffraction (XRPD) pattern comprising peaks at 7.67, 11.54, 18.27, and 23.28±0.2° 2θ using Cu Kα radiation; and
   (iii) a free base monohydrate crystalline Form III of Compound A, characterized by an X-ray powder diffraction (XRPD) pattern comprising peaks at 7.31, 10.77, and 13.96±0.2° 2θ using Cu Kα radiation,
   wherein Compound A is:

("Compound A")

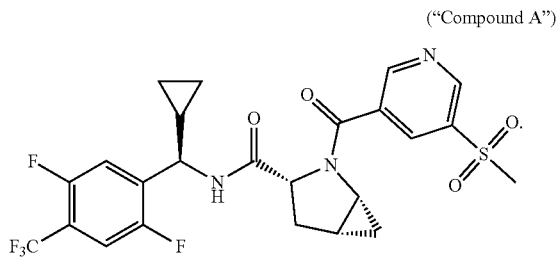 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]

2. The free base crystalline form of claim 1, wherein the free base crystalline form is a free base anhydrous crystalline Form I of Compound A, characterized by an X-ray powder diffraction (XRPD) pattern comprising peaks at 9.78, 12.45, 15.70, 16.46, and 16.94±0.2° 2θ using Cu Kα radiation.

3. The free base crystalline form of claim 2, further characterized by one or more of the following:
   (i) XRPD pattern peaks at 8.23, 24.40, 25.03, 25.49, and 32.03±0.2° 2θ using Cu Kα radiation;
   (ii) XRPD pattern peaks at 19.56, 20.11, 22.99, 23.97, 29.53, 41.91, and 42.83±0.2° 2θ using Cu Kα radiation;
   (iii) an XRPD pattern substantially as shown in FIG. 1;
   (iv) an endothermic transition at 147° C. to 157° C., as measured by differential scanning calorimetry;
   (v) an endothermic transition at 152° C.±3° C., as measured by differential scanning calorimetry;
   (vi) a dynamic vapor sorption ("DVS") substantially as shown in FIG. 4; and
   (vii) a thermogravimetric analysis ("TGA") substantially as shown in FIG. 3.

4. The free base crystalline form of claim 1, wherein the free base crystalline form is a free base anhydrous crystalline Form II of Compound A, characterized by an X-ray powder diffraction (XRPD) pattern comprising peaks at 7.67, 11.54, 18.27, and 23.28±0.2° 2θ using Cu Kα radiation.

5. The free base crystalline form of claim 4, further characterized by one or more of the following:
   (i) XRPD pattern peaks at 15.36, 16.33, 18.58, 21.38, 23.59, 24.61, 27.09, 43.40, and 44.26±0.2° 2θ using Cu Kα radiation;
   (ii) XRPD pattern peaks at 18.01, 25.17, 38.15, and 39.26±0.2° 2θ using Cu Kα radiation;
   (iii) an XRPD pattern substantially as shown in FIG. 5;
   (iv) an endothermic transition at 175° C. to 185° C., as measured by differential scanning calorimetry; and
   (v) an endothermic transition at 181° C.±3° C., as measured by differential scanning calorimetry.

6. The free base crystalline form of claim 1, where the free base crystalline form is a free base monohydrate crystalline Form III of Compound A, characterized by an X-ray powder diffraction (XRPD) pattern comprising peaks at 7.31, 10.77, and 13.96±0.2° 2θ using Cu Kα radiation.

7. The free base crystalline form of claim 6, further characterized by one or more of the following:
   (i) XRPD pattern peaks at 16.60, 18.56, 18.84, 19.41, 20.57, 21.61, 21.92, 22.28, 23.34, 24.23, 24.70, 25.69, and 28.87±0.2° 2θ using Cu Kα radiation;
   (ii) XRPD pattern peaks at 7.94, 20.10, 23.88, and 28.38±0.2° 2θ using Cu Kα radiation;
   (iii) an XRPD pattern substantially as shown in FIG. 6;
   (iv) an endothermic transition at 127° ° C. to 137° C., as measured by differential scanning calorimetry;
   (v) an endothermic transition at 132° C.±3° C., as measured by differential scanning calorimetry;
   (vi) a dynamic vapor sorption ("DVS") substantially as shown in FIG. 9; and
   (vii) a thermogravimetric analysis ("TGA") substantially as shown in FIG. 8.

8. A free base anhydrous crystalline form of Compound A ("Form IV"), characterized by an X-ray powder diffraction (XRPD) pattern comprising peaks at 8.06, 11.29, and 14.97±0.2° 2θ using Cu Kα radiation, wherein Compound A is:

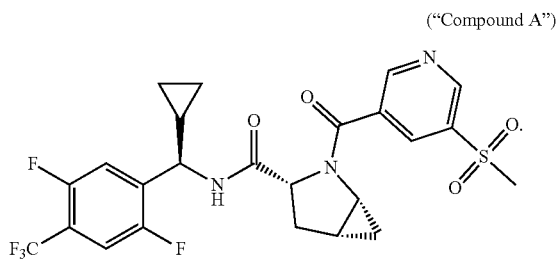 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]
("Compound A")

9. The crystalline form of claim 8, further characterized by XRPD pattern peaks at 17.19, 17.63, 18.39, 18.95, 19.17, 20.50, 24.87, 26.03, 26.62, 27.99, and 29.25±0.2° 2θ using Cu Kα radiation.

10. The crystalline form of claim 9, further characterized by XRPD pattern peaks at 12.08, 20.17, 22.37, 22.86, 25.69, 28.26, and 28.73±0.2° 2θ using Cu Kα radiation.

11. The crystalline form of claim 8, having an XRPD pattern substantially as shown in FIG. 10.

12. The crystalline form of claim 8, having an endothermic transition at 160° C. to 175° C. as measured by differential scanning calorimetry.

13. The crystalline form of claim 12, wherein the endothermic transition is at 167° C.±3° C.

14. The crystalline form of claim 8, having a dynamic vapor sorption ("DVS") substantially as shown in FIG. 13.

15. The crystalline form of claim 8, having a thermogravimetric analysis ("TGA") substantially as shown in FIG. 12.

16. A crystalline form of Compound A hydrochloride salt, characterized by an X-ray powder diffraction (XRPD) pattern comprising peaks at 8.45, 16.93, 23.74, 24.59, and 26.57±0.2° 2θ using Cu Kα radiation,
wherein Compound A is:

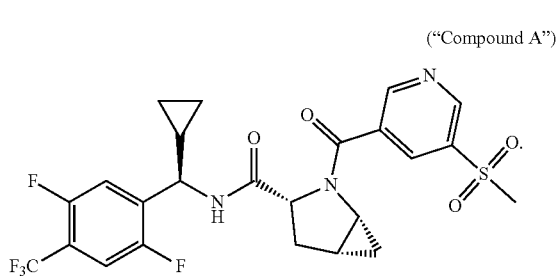 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]
("Compound A")

17. The crystalline form of claim 16, further characterized by one or more of the following:
(i) XRPD pattern peaks at 17.33, 17.76, 18.75, 19.51, 19.81, 20.53, 21.36, 22.95, 25.28, 25.89, 26.94, 27.44, and 29.41±0.2° 2θ using Cu Kα radiation;
(ii) XRPD pattern peaks at 8.74, 16.08, 19.81, and 28.58±0.2° 2θ using Cu Kα radiation;
(iii) XRPD pattern substantially as shown in FIG. 16;
(iii) an endothermic transition at 125° C. to 140° C., as measured by differential scanning calorimetry;
(iv) an endothermic transition at 134° C.±3° C., as measured by differential scanning calorimetry;
(v) a thermogravimetric analysis ("TGA") substantially as shown in FIG. 18; and
(vi) a dynamic vapor sorption ("DVS") substantially as shown in FIG. 19.

18. A crystalline form of Compound A and dichloromethane, characterized by an X-ray powder diffraction (XRPD) pattern comprising peaks at 11.46, 16.91, 23.10, and 24.58±0.2° 2θ using Cu Kα radiation,
wherein Compound A is:

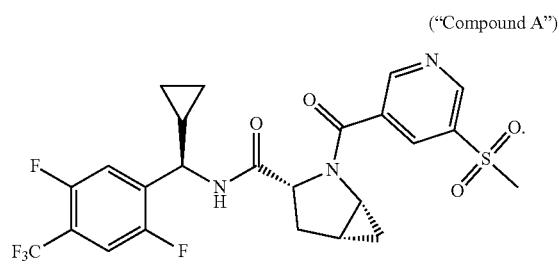 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]
("Compound A")

19. The crystalline form of claim 18, further characterized by one or more of the following:
(i) XRPD pattern peaks at 8.25, 16.26, 18.82, 19.50, 19.90, 20.52, 20.79, 21.58, 23.92, and 29.35±0.2° 2θ using Cu Kα radiation;
(ii) XRPD pattern peaks at 6.76, 25.18, 26.20, 26.95, 27.18, 27.62, and 28.26±0.2° 2θ using Cu Kα radiation;
(iii) an XRPD pattern substantially as shown in FIG. 20;
(iv) an endothermic transition at 70° C. to 80° C., as measured by differential scanning calorimetry;
(v) an endothermic transition at 76° C.±3° C., as measured by differential scanning calorimetry; and
(vi) a thermogravimetric analysis ("TGA") substantially as shown in FIG. 22.

20. A crystalline form of Compound A and nitromethane, characterized by an X-ray powder diffraction (XRPD) pattern comprising peaks at 8.94, 15.86, 17.12, 19.51, 19.83, and 24.41±0.2° 2θ using Cu Kα radiation,
wherein Compound A is:

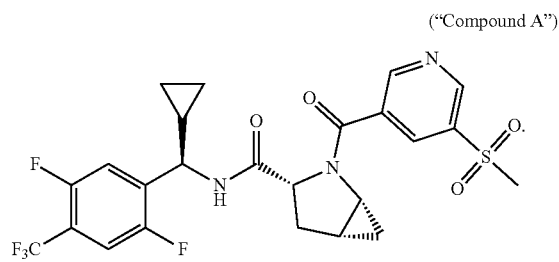 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]
("Compound A")

21. The crystalline form of claim 20, further characterized by one or more of the following:
(i) XRPD pattern peaks at 10.18, 18.16, 20.54, 21.93, 23.06, 23.92, and 25.37±0.2° 2θ using Cu Kα radiation;
(ii) XRPD pattern peaks at 19.01, 22.68, 26.61, and 28.32±0.2° 2θ using Cu Kα radiation;
(iii) an XRPD pattern substantially as shown in FIG. 23;
(iv) an endothermic transition at 81° ° C. to 97° C., as measured by differential scanning calorimetry
(v) an endothermic transition at 89° C.±3° C., as measured by differential scanning calorimetry; and
(vi) a thermogravimetric analysis ("TGA") substantially as shown in FIG. 25.

22. A crystalline form of Compound A and hexafluoro-2-propanol, characterized by an X-ray powder diffraction (XRPD) pattern comprising peaks at 16.17, 16.70, 18.20, and 23.03±0.2° 2θ using Cu Kα radiation,
wherein Compound A is:

("Compound A")

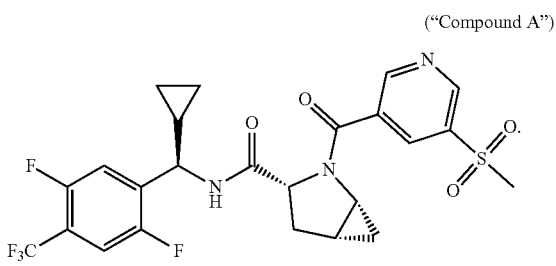 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]

23. The crystalline form of claim 22, further characterized by one or more of the following:
(i) XRPD pattern peaks at 9.49, 11.20, 20.18, 21.39 23.74, 25.46, 27.00, 29.24, and 33.76±0.2° 2θ using Cu Kα radiation;
(ii) an XRPD pattern substantially as shown in FIG. 26;
(iii) an endothermic transition at 85° C. to 95° C., as measured by differential scanning calorimetry;
(iv) an endothermic transition at 90° C.±3° C., as measured by differential scanning calorimetry; and
(v) a thermogravimetric analysis ("TGA") substantially as shown in FIG. 28.

24. A cocrystal comprising Compound A and a coformer, wherein Compound A is:

("Compound A")

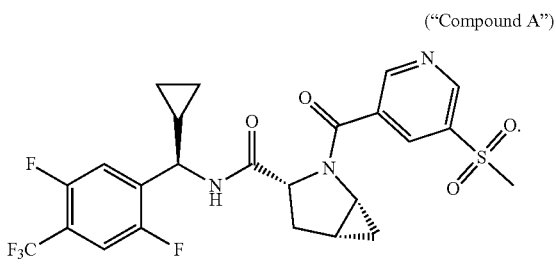 [SMILES: CS(=O)(=O)c1cncc(C(=O)N2[C@@H](C(=O)N[C@@H](c3cc(F)c(C(F)(F)F)cc3F)C3CC3)C[C@H]3C[C@H]32)c1]

25. The cocrystal of claim 24, wherein the coformer comprises benzoic acid, oxalic acid, malonic acid, succinic acid, maleic acid, fumaric acid, glutaric acid, adipic acid, pimelic acid, 3,5-dihydroxybenzoic acid, triflouroacetic acid, 2,5-dihydroxybenzoic acid, 2,4-dihydroxybenzoic acid, m-nitrobenzoic acid, 5-chlorosalicylic acid, saccharin, citric acid, tartaric acid, 2,3-dihydroxybenzoic acid, 3,4-dihydroxybenzoic acid, barbital, 4-hydroxybenzoic acid, 1-hydroxy-2-naphthoic acid, malic acid, 3-hydroxybenzoic acid, 6-hydroxy-2-naphthoic acid, methylgallate, salicyclic acid, 2-hydroxybenzoic acid, formic acid, 3-hydroxy-2-naphthoic acid, sulfacetamide, acetic acid, sulfaproxyline, sulfuric acid, sulfamic acid, ethylenediamine, octadecylamine, glucono-delta lactone, allocitric acid, sucralose, indole, 1-hydroxyethyldene-1,1-diphosphonic acid, skatole, 5-chlorosalicylic acid, urea, 5-nitroisophthalic acid, trimesic acid, gentisic acid, ketoglutaric acid, adamantine tricarboxylic acid, t-butylhydroquinone, isocirtric acid, trifluoroethanol, camphoric acid, 4-aminobenzoic acid, 2,6-pyridinedicarboxylic acid, aspirin, butyric acid, formamide, nicotinamide, nitromethane, 1,4-benzoquinone, glycolic acid, terephtalaldehide, dioxane, N-methylpyrrolidone, dimethylsulfoxide, dimethylacetamide, acetone, dimethylformamide, furfural, 4,4'-bipyridine, or a mixture thereof.

26. The cocrystal of claim 25, wherein the coformer comprises propyl gallate, glycerol, propylene glycol, maltol, urea, or a mixture thereof.

27. The cocrystal of claim 24, wherein the coformer comprises propyl gallate.

28. The cocrystal of claim 27, characterized by one or more of the following:
(i) an X-ray powder diffraction (XRPD) pattern comprising peaks at 8.66, 15.00, 17.72, 18.82, and 20.32±0.2° 2θ using Cu Kα radiation;
(ii) XRPD pattern peaks at 9.21, 19.36, 20.49, and 22.57±0.2° 2θ using Cu Kα radiation;
(iii) XRPD pattern peaks at 3.05, 11.24, 18.32, 21.73, 22.98, 23.39, 25.01, 25.51, 26.30, 26.52, and 28.31±0.2° 2θ using Cu Kα radiation;
(iv) an XRPD pattern substantially as shown in FIG. 29;
(v) an endothermic transition at 116° C. to 126° C., as measured by differential scanning calorimetry;
(vi) an endothermic transition at 121° C.±3° C., as measured by differential scanning calorimetry; and
(v) a thermogravimetric analysis ("TGA") substantially as shown in FIG. 31.

29. The cocrystal of claim 24, wherein the coformer comprises glycerol.

30. The cocrystal of claim 29, characterized by one or more of the following:
(i) an X-ray powder diffraction (XRPD) pattern comprising peaks at 16.84, 18.48, 19.40, and 21.49±0.2° 2θ using Cu Kα radiation;
(ii) XRPD pattern peaks at 9.70, 15.60, 16.39, 18.95, 22.51, 24.53, and 24.92±0.2° 2θ using Cu Kα radiation;
(iii) XRPD pattern peaks at 8.17, 12.38, 22.87, and 27.61±0.2° 2θ using Cu Kα radiation;
(iv) an XRPD pattern substantially as shown in FIG. 32;
(v) an endothermic transition at 140° C. to 151° C. and 152° C. to 165° C., as measured by differential scanning calorimetry;
(vi) an endothermic transition at 148° C.±3° C. and 156° C.±3° C., as measured by differential scanning calorimetry; and
(vii) a thermogravimetric analysis ("TGA") substantially as shown in FIG. 34.

31. The cocrystal of claim 24, wherein the coformer comprises propylene glycol.

32. The cocrystal of claim 31, characterized by one or more of the following:
(i) an X-ray powder diffraction (XRPD) pattern comprising peaks at 16.82, 18.26, 18.93, 19.37, and 21.52±0.2° 2θ using Cu Kα radiation;
(ii) XRPD pattern peaks at 7.87, 15.61, 16.36, 18.39, 20.39, 21.12, 22.47, and 24.46±0.2° 2θ using Cu Kα radiation;
(iii) XRPD pattern peaks at 9.69, 20.02, 21.83, 22.85, 23.84, 25.05, and 27.07±0.2° 2θ using Cu Kα radiation;
(iv) having an XRPD pattern substantially as shown in FIG. 35;
(v) a broad dissociation endothermic transition at 80° C. to 135° C., as measured by differential scanning calorimetry;
(vi) an endothermic transition at 89° ° C. to 124° C.±3° C., as measured by differential scanning calorimetry; and
(vii) a thermogravimetric analysis ("TGA") substantially as shown in FIG. 37.

33. The cocrystal of claim 24, wherein the coformer comprises maltol.

34. The cocrystal of claim 33, characterized by one or more of the following:
- (i) an X-ray powder diffraction (XRPD) pattern comprising peaks at 16.85, 18.18, 19.53, and 23.54±0.2° 2θ using Cu Kα radiation;
- (ii) XRPD pattern peaks at 6.58, 8.86, 13.68, 14.60, 15.25, 21.52, 25.26, and 26.63±0.2° 2θ using Cu Kα radiation;
- (iii) XRPD pattern peaks at 4.44, 7.98, and 13.13±0.2° 2θ using Cu Kα radiation;
- (iv) an XRPD pattern substantially as shown in FIG. 38;
- (v) a broad dissociation endothermic transition at 125° C. to 135° C., as measured by differential scanning calorimetry;
- (vi) an endothermic transition at 130° C.±3° C., as measured by differential scanning calorimetry; and
- (vii) a thermogravimetric analysis ("TGA") substantially as shown in FIG. 40.

35. The cocrystal of claim 24, wherein the coformer comprises urea.

36. The cocrystal of claim 35, characterized by one or more of the following:
- (i) an X-ray powder diffraction (XRPD) pattern comprising peaks at 3.99, 11.24, 17.62, and 18.37±0.2° 2θ using Cu Kα radiation;
- (ii) XRPD pattern peaks at 8.01, 8.39, 14.96, 17.47, 18.94, 19.13, 20.51, 24.65, 24.86, 25.70, 25.97, and 26.62±0.2° 2θ using Cu Kα radiation;
- (iii) XRPD pattern peaks at 15.21, 16.93, 17.16, 22.37, 26.35, 28.01, 28.26, 28.77, and 29.25±0.2° 2θ using Cu Kα radiation;
- (iv) an XRPD pattern substantially as shown in FIG. 41;
- (v) a dissociation endothermic transition at 160° C. to 170° C. and 171° C. to 180° C., as measured by differential scanning calorimetry;
- (vi) an endothermic transition at 167° C.±3° C. and 174° C.±3° C., as measured by differential scanning calorimetry; and
- (vii) a thermogravimetric analysis ("TGA") substantially as shown in FIG. 43.

37. A pharmaceutical composition comprising the crystalline form of claim 8 and a pharmaceutically acceptable carrier.

38. A method of treating heart failure in a subject in need thereof comprising administering to the subject the crystalline form of claim 8 in an amount effective to treat heart failure.

39. A method of treating heart failure in a subject in need thereof comprising administering to the subject the composition of claim 37 in an amount effective to treat heart failure.

* * * * *